(12) United States Patent
Knight et al.

(10) Patent No.: US 8,642,604 B2
(45) Date of Patent: *Feb. 4, 2014

(54) SUBSTITUTED PYRAZOLO[3,2-D]PYRIMIDINES AS ANTI-CANCER AGENTS

(75) Inventors: Zachary A. Knight, San Francisco, CA (US); Beth Apsel, San Francisco, CA (US); Kevan M. Shokat, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 674 days.

This patent is subject to a terminal disclaimer.

(21) Appl. No.: 12/509,281

(22) Filed: Jul. 24, 2009

(65) Prior Publication Data

US 2010/0009963 A1 Jan. 14, 2010

Related U.S. Application Data

(63) Continuation of application No. 11/732,856, filed on Apr. 4, 2007, now Pat. No. 7,585,868.

(60) Provisional application No. 60/744,269, filed on Apr. 4, 2006, provisional application No. 60/744,270, filed on Apr. 4, 2006.

(51) Int. Cl.
*A61K 31/519* (2006.01)
*A61P 35/00* (2006.01)
*C07D 487/04* (2006.01)

(52) U.S. Cl.
USPC ...... 514/262.1; 544/280; 544/262; 514/265.1

(58) Field of Classification Search
USPC ........................................ 514/262.1
See application file for complete search history.

(56) References Cited

U.S. PATENT DOCUMENTS

| | | |
|---|---|---|
| 4,704,381 A | 11/1987 | Schaumann et al. |
| 5,240,941 A | 8/1993 | Bruneau |
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |

(Continued)

FOREIGN PATENT DOCUMENTS

| | | |
|---|---|---|
| CA | 1338379 | 6/1996 |
| CN | 101602768 | 12/2009 |

(Continued)

OTHER PUBLICATIONS

Abdel-Mohsen, S.A., "Synthesis, reactions and antimicrobial activity of 2-amino-4-(8-quinolinol-5-yl)-1-(p-tolyl)-pyrrole-3-carbonitrile", Bull. Korean Chem. Soc. 2005 26(5):719-728.

(Continued)

Primary Examiner — Susanna Moore
(74) Attorney, Agent, or Firm — Kilpatrick Townsend & Stockton LLP

(57) ABSTRACT

The present invention provides novel compounds that are antagonists of PI3 kinase, PI3 kinase and tyrosine kinase, PI3 kinase and mTOR, or PI33 kinase, mTOR and tyrosine kinase.

23 Claims, 11 Drawing Sheets

(56) References Cited

U.S. PATENT DOCUMENTS

| | | |
|---|---|---|
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat et al. |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | Desimone et al. |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Bhat et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |

(56) References Cited

U.S. PATENT DOCUMENTS

| | | |
|---|---|---|
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |

FOREIGN PATENT DOCUMENTS

| | | | |
|---|---|---|---|
| EP | 0773023 | A1 | 5/1997 |
| EP | 1020445 | B1 | 8/2008 |
| GB | 812366 | | 4/1959 |
| GB | 937725 | | 9/1963 |
| JP | 61109797 | | 5/1986 |
| JP | 5256693 | | 10/1993 |
| JP | 8295667 | A | 12/1996 |
| JP | 9143163 | | 6/1997 |
| JP | 10206995 | A | 8/1998 |
| JP | 2000072773 | A | 3/2000 |
| JP | 2002037787 | A | 2/2002 |
| JP | 2002131859 | A2 | 5/2002 |
| JP | 2003073357 | A2 | 3/2003 |
| JP | 2004161716 | A | 6/2004 |
| WO | WO83/01446 | A1 | 4/1983 |
| WO | WO91/17161 | A1 | 11/1991 |
| WO | WO92/14733 | A1 | 9/1992 |
| WO | WO93/16091 | A1 | 8/1993 |
| WO | WO93/16092 | A1 | 8/1993 |
| WO | WO93/18035 | A1 | 9/1993 |
| WO | WO93/22443 | A1 | 11/1993 |
| WO | WO 94/13677 | A1 | 6/1994 |
| WO | WO94/17803 | A1 | 8/1994 |
| WO | WO95/12588 | A1 | 5/1995 |
| WO | WO95/29673 | A1 | 11/1995 |
| WO | WO95/32984 | A1 | 12/1995 |
| WO | WO96/40706 | A1 | 12/1996 |
| WO | WO97/28133 | A1 | 8/1997 |
| WO | WO97/28161 | A1 | 8/1997 |
| WO | WO98/41525 | A1 | 9/1998 |
| WO | WO98/52611 | A1 | 11/1998 |
| WO | WO98/57952 | A1 | 12/1998 |
| WO | WO00/17202 | A1 | 3/2000 |
| WO | WO01/02369 | A2 | 1/2001 |
| WO | WO01/16114 | A2 | 3/2001 |
| WO | WO01/19829 | A2 | 3/2001 |
| WO | WO01/25238 | A2 | 4/2001 |
| WO | WO01/31063 | A1 | 5/2001 |
| WO | WO01/38584 | A2 | 5/2001 |
| WO | WO01/16114 | A3 | 8/2001 |
| WO | WO01/55140 | A1 | 8/2001 |
| WO | WO01/56988 | A1 | 8/2001 |
| WO | WO01/19829 | A3 | 9/2001 |
| WO | WO01/25238 | A3 | 10/2001 |
| WO | WO01/38584 | A3 | 10/2001 |
| WO | WO01/81346 | A2 | 11/2001 |
| WO | WO02/06192 | A1 | 1/2002 |
| WO | WO01/81346 | A3 | 3/2002 |
| WO | WO01/02369 | A3 | 4/2002 |
| WO | WO02/30944 | A2 | 4/2002 |
| WO | WO02/057425 | A2 | 7/2002 |
| WO | WO02/076986 | A1 | 10/2002 |
| WO | WO02/080926 | A1 | 10/2002 |
| WO | WO02/083143 | A1 | 10/2002 |
| WO | WO02/088025 | A1 | 11/2002 |
| WO | WO02/090334 | A1 | 11/2002 |
| WO | WO02/30944 | A3 | 1/2003 |
| WO | WO03/000187 | A2 | 1/2003 |
| WO | WO03/016275 | A1 | 2/2003 |
| WO | WO03/020880 | A2 | 3/2003 |
| WO | WO03/024969 | A1 | 3/2003 |
| WO | WO03/035075 | A1 | 5/2003 |
| WO | WO03/059884 | A1 | 7/2003 |
| WO | WO03/020880 | A3 | 10/2003 |
| WO | WO03/082341 | A1 | 10/2003 |
| WO | WO03/106426 | A1 | 12/2003 |
| WO | WO2004/006906 | A2 | 1/2004 |
| WO | WO2004/006906 | A3 | 3/2004 |
| WO | WO2004/018058 | A2 | 3/2004 |
| WO | WO2004/031177 | A1 | 4/2004 |
| WO | WO2004/039774 | A2 | 5/2004 |
| WO | WO2004/018058 | A3 | 7/2004 |
| WO | WO2004/039774 | A3 | 7/2004 |
| WO | WO03/000187 | A3 | 8/2004 |
| WO | WO2004/087053 | A2 | 10/2004 |
| WO | WO2004/111014 | A1 | 12/2004 |
| WO | WO2005/002585 | A1 | 1/2005 |
| WO | WO2005/007085 | A | 1/2005 |
| WO | WO2005/012323 | A2 | 2/2005 |
| WO | WO2005/016348 | A1 | 2/2005 |
| WO | WO2005/016349 | A1 | 2/2005 |
| WO | WO2005/016528 | A2 | 2/2005 |
| WO | WO2005/021533 | A1 | 3/2005 |

(56) References Cited

FOREIGN PATENT DOCUMENTS

| | | |
|---|---|---|
| WO | WO02/57425 A3 | 4/2005 |
| WO | WO2005/012323 A3 | 5/2005 |
| WO | WO2005/016528 A3 | 5/2005 |
| WO | WO2005/044181 A2 | 5/2005 |
| WO | WO 2005/047289 A1 | 5/2005 |
| WO | WO2005/061460 A1 | 7/2005 |
| WO | WO2005/063258 A1 | 7/2005 |
| WO | WO2005/067901 A2 | 7/2005 |
| WO | WO2005/074603 A2 | 8/2005 |
| WO | WO2005/007085 A3 | 9/2005 |
| WO | WO2005/097800 A1 | 10/2005 |
| WO | WO2005/105760 A1 | 11/2005 |
| WO | WO2005/067901 A3 | 12/2005 |
| WO | WO2005/112935 A1 | 12/2005 |
| WO | WO2005/113556 A1 | 12/2005 |
| WO | WO2005/117889 A1 | 12/2005 |
| WO | WO2005/120511 A1 | 12/2005 |
| WO | WO2005/044181 A3 | 3/2006 |
| WO | WO2006/030032 A1 | 3/2006 |
| WO | WO2006/038865 A1 | 4/2006 |
| WO | WO2006/050501 A2 | 5/2006 |
| WO | WO 2006/050946 A1 | 5/2006 |
| WO | WO2006/068760 A2 | 6/2006 |
| WO | WO2004/087053 A3 | 8/2006 |
| WO | WO2006/089106 A2 | 8/2006 |
| WO | WO2006/108107 A1 | 10/2006 |
| WO | WO2006/112666 A1 | 10/2006 |
| WO | 2006/114180 A1 | 11/2006 |
| WO | WO2005/074603 A3 | 11/2006 |
| WO | WO2006/114064 A2 | 11/2006 |
| WO | WO2006/114065 | 11/2006 |
| WO | WO2006/068760 A3 | 12/2006 |
| WO | WO2006/089106 A3 | 12/2006 |
| WO | WO2007/002293 A2 | 1/2007 |
| WO | WO2007/006547 A1 | 1/2007 |
| WO | WO2007/020046 A1 | 2/2007 |
| WO | WO2007/002293 A3 | 3/2007 |
| WO | WO2007/025090 A2 | 3/2007 |
| WO | WO2006/050501 A3 | 5/2007 |
| WO | WO2007/061737 A2 | 5/2007 |
| WO | WO2006/114064 A3 | 6/2007 |
| WO | WO2006/114065 A3 | 6/2007 |
| WO | WO2007/025090 A3 | 6/2007 |
| WO | WO2007/075554 A2 | 7/2007 |
| WO | WO2007/079164 A2 | 7/2007 |
| WO | 2007/095223 A2 | 8/2007 |
| WO | 2007/106503 A2 | 9/2007 |
| WO | WO2007/075554 A3 | 9/2007 |
| WO | WO2007/079164 A3 | 9/2007 |
| WO | WO2007/103308 A2 | 9/2007 |
| WO | WO2007/112005 A2 | 10/2007 |
| WO | WO2007/114926 A2 | 10/2007 |
| WO | WO2007/121453 A2 | 10/2007 |
| WO | WO2007/121920 A2 | 11/2007 |
| WO | WO2007/121924 A2 | 11/2007 |
| WO | WO2007/124854 A1 | 11/2007 |
| WO | WO2007/125310 A2 | 11/2007 |
| WO | WO2007/125315 A2 | 11/2007 |
| WO | WO2007/126841 A2 | 11/2007 |
| WO | WO2007/134828 A1 | 11/2007 |
| WO | WO2007/135380 A2 | 11/2007 |
| WO | WO2007/135398 A1 | 11/2007 |
| WO | WO2007/061737 A3 | 12/2007 |
| WO | WO2007/125315 A3 | 12/2007 |
| WO | WO2007/121920 A3 | 1/2008 |
| WO | WO2007/103308 A3 | 2/2008 |
| WO | WO2007/112005 A3 | 2/2008 |
| WO | WO2007/125310 A3 | 3/2008 |
| WO | WO2008/025755 A1 | 3/2008 |
| WO | WO2008/047821 A1 | 4/2008 |
| WO | WO2008/063625 A2 | 5/2008 |
| WO | WO2008/064018 A1 | 5/2008 |
| WO | WO2007/121453 A3 | 7/2008 |
| WO | WO2007/135380 A3 | 7/2008 |
| WO | WO2008/063625 A3 | 7/2008 |
| WO | WO2008/079028 A1 | 7/2008 |
| WO | WO2008/082487 A2 | 7/2008 |
| WO | WO2008/094737 A2 | 8/2008 |
| WO | WO2007/121924 A3 | 9/2008 |
| WO | WO2008/112715 A2 | 9/2008 |
| WO | WO2007/114926 A3 | 10/2008 |
| WO | WO2008/118454 A2 | 10/2008 |
| WO | WO2008/118455 A1 | 10/2008 |
| WO | WO2008/118468 A1 | 10/2008 |
| WO | WO2008/125014 A1 | 10/2008 |
| WO | WO2008/125207 A1 | 10/2008 |
| WO | WO2008/127226 A2 | 10/2008 |
| WO | WO2007/126841 A3 | 11/2008 |
| WO | WO2008/112715 A3 | 11/2008 |
| WO | WO2008/118454 A3 | 11/2008 |
| WO | WO2008/136457 A1 | 11/2008 |
| WO | WO2008/082487 A3 | 12/2008 |
| WO | WO2008/127226 A3 | 12/2008 |
| WO | WO2009/000412 A1 | 12/2008 |
| WO | WO2009/004621 A1 | 1/2009 |
| WO | WO2009/010925 A2 | 2/2009 |
| WO | WO2009/023718 A2 | 2/2009 |
| WO | WO2008/094737 A3 | 3/2009 |
| WO | WO2009/023718 A3 | 4/2009 |
| WO | WO2009/044707 A1 | 4/2009 |
| WO | WO 2009/050506 A2 | 4/2009 |
| WO | WO2009/064802 A2 | 5/2009 |
| WO | WO2009/010925 A3 | 7/2009 |
| WO | WO2009/064802 A3 | 7/2009 |
| WO | WO2009/088986 A1 | 7/2009 |
| WO | WO2009/088990 A1 | 7/2009 |
| WO | WO2009/100406 A2 | 8/2009 |
| WO | WO2009/117157 A1 | 9/2009 |
| WO | WO2009/050506 A3 | 11/2009 |
| WO | WO2009/100406 A3 | 11/2009 |
| WO | WO2010/009207 A1 | 1/2010 |
| WO | WO2010/019210 A2 | 2/2010 |
| WO | WO2010/036380 A1 | 4/2010 |
| WO | WO2010/039534 A2 | 4/2010 |
| WO | WO2010/019210 A3 | 5/2010 |
| WO | 2010039534 A3 | 8/2010 |

OTHER PUBLICATIONS

Beeram, M. et al., "Akt-induced endocrine therapy resistance is reversed by inhibition of mTOR signaling", Annals of Oncology 18:1323-1328, 2007.
European Examination Report dated Sep. 14, 2011 for EP Application No. 07873406.8, 4 pages.
Feldman, M.E. et al., "Active site inhibitors of mTOR target rapamycin-resistant outputs of mTORC1 and mTORC2", PLOS Biology 7(2):371-383, Feb. 2009.
International Preliminary Report on Patentability and Written Opinion dated Apr. 19, 2011 for International Application No. PCT/US2009/060985, 6 pages.
International Preliminary Report on Patentability and Written Opinion dated Jan. 1, 2011 for International Application No. PCT/US2009/049969, 7 pages.
International Preliminary Report on Patentability and Written Opinion dated May 22, 2007 for International Application No. PCT/US2005/042524, 12 pages.
International Preliminary Report on Patentability and Written Opinion dated Nov. 4, 2008 for International Application No. PCT/US2007/008355, 7 pages.
International Preliminary Report on Patentability and Written Opinion dated Oct. 8, 2008 for International Application No. PCT/US2007/008395, 6 pages.
International Search Report dated Jun. 28, 2010 for International Application No. PCT/US2009/060985, 5 pages.
International Search Report dated Mar. 15, 2010 for International Application No. PCT/US2009/049969, 4 pages.
Kim, M. et al., "Activation and function of the mTORC1 pathway in mast cells", The Journal of Immunology 180:4586-4595, Apr. 2008.
Kreutzberger, A. et al., "5-substituierte 4-aminopyrimidine durch aminomethinylierung von acetonitrilen", Justus Liebigs Annalen der

(56) References Cited

OTHER PUBLICATIONS

Chemie 4:537-544, 1977 (not provided in English as received by USPTO Examiner Susanna Moore).
Supplementary European Search Report dated Sep. 20, 2011 for EP Application No. 07754845.1, 4 pages.
Takeuchi, H. et al., "Synergistic augmentation of reapamycin-induced autophagy in malignant glioma cells by phosphatidylinositol 3-kinase/protein kinase B inhibitors", Cancer Research 65(8):3336-3346, Apr. 15, 2005.
U.S. Appl. No. 13/016,957, filed Jan. 28, 2011, Tanaka et al.
U.S. Appl. No. 13/112,611, filed May 20, 2011, Ren et al.
U.S. Appl. No. 13/289,540, filed Nov. 4, 2011, Ren et al.
Ames et al., "Heterocyclic Synthesis from o-Halogen-acids. Part II. Thienopyridinones and Thienopyranones from 3-bromothiophene -2- and 4-Bromothiophene-3-Carboxylic Acids", Journal of the Chemical Society, Perkin Transactions 1, Jan. 14:1390-1395 (1975).
BASOTEST®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011, 10 pages.
Cámpora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.
Cámpora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.
Chaisuparat, et al. Dual Inhibition of PI3K(alpha) and mTOR as an Alternative Treatment for Kaposi's Sarcoma. Cancer Research. 2008;68:8361.
Chappelow, et al. Neovascular Age-Related Macular Degeneration: Potential Therapies. Drugs. 2008;68(8):1029-1036.
Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.
Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.
Donati. Emerging Therapies for Neovascular Age-Related Macular Degeneration: State of the Art. Ophthalmologica. 2007;221:366-377.
European search report and search opinion dated Oct. 26, 2011 for Application No. 9700424.6, 5 pages.
European Search Report dated Mar. 1, 2010 for EP Application No. 07873406.8, 5 pages.
Extended European Search Report from corresponding European Application No. 09700784.3 dated Oct. 28, 2011, 6 pages.
Graupera, et al. Angiogenesis selectively requires the p110 isoform of PI3K to control endothelial cell migration. Nature. 2008;453:662-666.
Hellwinkel, et al. Heterocyclensynthesen mit MF/Al2O3-Basensystemen: 2-Arylbenzofurane and 2,3-Diarylisochinolin-1(2H)-one. Synthesis. 1995;1995(9):1135-41.
International Preliminary Report on Patentability from International Application No. PCT/US2009/000042 issued Jul. 6, 2010, 9 pages.
International search report and written opinion dated Aug. 22, 2011 for PCT/US2011/037412, 2 pages.
International search report and written opinion dated Nov. 20, 2009 for PCT/US2009/005380, 9 pages.
International search report dated Nov. 2, 2010 for PCT Application No. PCT/US10/02020, 8 pages.
International search report dated Mar. 11, 2009 for PCT Application No. PCT/US2009/00038, 1 page.
International search report dated Mar. 23, 2009 for PCT Application No. PCT/US2009/00042, 2 pages.
Kajita, et al. Nickel-catalyzed decarbonylative addition of phthalimides to alkynes. J Am Chem Soc. May 14, 2008;130(19):6058-9.

Kost et al., "Recyclization of 3-Alkyl- and 1,3-Dialkylisoquinolinium Salts to Naphthylamines", Chemistry of Heterocyclic Compounds, Jan., 16(9):965-970 (1981).
Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan. 8:857-862 (1978).
Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.
Lee, et al. All roads lead to mTOR: integrating inflammation and tumor angiogenesis.. Cell Cycle. 2007;6(24):3011-3014.
Majumder, et al. mTOR inhibition reverses Akt-dependent prostate intraepithelial neoplasia through regulation of apoptotic and HIF-1-dependent pathways. Nature Medicine. 2004;10:594-601.
Mellinghoff, et al. TORward AKTually useful mouse models. Nature Medicine. 2004;10:579-580.
Modi, et at. Isoquinolones: Part IV—Synthesis of 3-Methyl, 3-Formyl & Other 3-Substituted N-Arylisoquinolones, Indian J. Chem. 1979; 18B:304-306.
Nemazanyi, et al. 3-Amino-4-aryl-1(2H)-isoquinolones. Chemistry of Heterocyclic Compounds. Mar. 1991;27(3):307-8.
Oda, et al. PIK3CA Cooperates with Other Phosphatidylinositol 3'-Kinase Pathway Mutations to Effect Oncogenic Transformation. Cancer Research. 2008;68:8127.
Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.
Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Patel, et al. Immunopathological aspects of age-related macular degeneration. Seminars in Immunopathology. 2008;30(2):97-110.
Stanoeva et al. Homophthalic anhydrides and their application to the synthesis of heterocyclic compounds (review). Chemistry of Heterocyclic Compounds. Dec. 1984;20(12);1305-15.
Supplementary European Examination Report dated Sep. 20, 2011 for EP Application No. 07754845.1, 4 pages.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole-4-carboxylic acid hydrazides under the influence of CuCl: formatin of a diazepinone and dehydrodimerization into the corresponding bis(pyrazolo [4,3-d] [1,2] diazepinone)", Tetrahedron Letters, Jan., 46(26): 4457-4459 (2005).
Yaguchi, et al. Antitumor activity of ZSTK474, a new phosphatidylinositol 3-kinase inhibitor. J. Natl. Cancer. Inst. 2006; 98(8): 545-556. Abstract only.
"Report of the Expert Committee on the Diagnosis and Classification of Diabetes Mellitus", *Diabetes Care* (1992) 2(Suppl 1):S5-S19.
Andrews, R.C., et al. "Effects of the 11β-Hydroxysteroid Dehydrogenase Inhibitor Carbenoxolone on Insulin Sensitivity in Men with Type 2 Diabetes", *J. Clin. Endocrinol. Metab.* (2003) 88(1):285-291.
Arnold, et al. "Pyrrolo[2,3-*d*]pyrimidines containing an extended 5-substituent as potent and selective inhibitors of Ick I", *Bioorg. & Med. Chem. Lett* (2000) 10:2167-70.
Banker, G.S., et al. *Modern Pharmaceutics*, 3ed, Marcel Dekker, New York, 1996, pp. 451-596.
Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", *J. Med. Chem.* (2002) 45(18):3813-3815.
Barnes, P.J., et al. "Efficacy and Safety of Inhaled Corticosteroids in Asthma", *Am. Rev. Respir. Dis.* (1993) 148:S1-26.
Bell, G., et al. "Glucokinase Mutations Insulin Secretion, and Diabetes Mellitus", *Annu. Rev. Physiol.*, (1996) 58:171-186.

(56) References Cited

OTHER PUBLICATIONS

Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.

Bohren, K.M., et al. "Expression, Crystallization and Preliminary Crystallographic Analysis of Human Carbonyl Reductase", *J. Mol. Biol.* (1994) 224:659-664.

Cox, B., et al. "Human Colorectal Cancer Cells Efficiently Conjugate the Cyclopentenone Prostaglandin, Prostaglandin $J_2$ to Glutathione", *Biochim. Biophys. Acta* (2002) 1584:37-45.

Diederich, S., et al. "In the Search for Specific Inhibitors of Human 11β-Hydroxysteroid-Dehydrogenases (11β-HSDs): Chenodeoxycholic Acid Selectively Inhibits 11β-HSD-I", *Eur. J. Endocrinol.* (2000) 142:200-207.

Ding, S., et al. "A Combinatorial Scaffold Approach Toward Kinase-Directed Heterocycle Libraries", *J. Am. Chem. Soc.* (2002) 124(8):1594-1596.

Ding, S., et al. "A Concise and Traceless Linker Strategy Toward Combinatorial Libraries of 2,6,9-Substituted Purines", *J. Org. Chem.* (2001) 66:8273-8276.

Ding, S., et al. "Resin-Capture and Release Strategy Toward Combinatorial Libraries of 2,6,9-Substituted Purines", *J. Comb. Chem.* (2002) 4:183-186.

Fajans, S., et al. "Maturity Onset Diabetes of the Young (MODY)", *Diabet. Med.* (1996) 13:S90-S95.

Feinstein, M.B., et al. "Regulation of the Action of Hydrocotisone in Airway Epithelial Cells by 11β-Hydroxysteroid Dehydrogenase", *Am. J. Respir. Cell. Mol. Biol.* (1999) 21:403-408.

Fingl, E., et al. "General Principles", *The Pharmacological Basis of Therapeutics*, Fifth Edition (1975), Ch. 1, 1-46.

Forrest, G.L., et al. "Carbonyl Reductase", *Chem. Biol. Interact.* (2000) 129:21-40.

Forrest, G.L., et al. "Induction of a Human Carbonyl Reductase Gene Located on Chromosome 21", *Biochim. Biophys. Acta.* (1990) 1048:149-155.

Franzen, R. "The Suzuki, the Heck, and the Stille reaction—three versative methods for the introduction of new C—C bonds on solid support", *Can J. Chem.* (2000) 78:957-962.

Funder, J.W., et al. "Mineralocorticoid Action: Target Tissue Specificity Is Enzyme, Not Receptor, Mediated", *Science* (1998) 242:583-585.

Garber, M.E., et al. "Diversity of Gene Expression in Adenocarcinoma of the Lung", *Proc. Nat. Acad. Sci. USA* (2001) 98(24):13784-13789.

Gonzalez, B., et al. "Protection against Daunorubicin Cytotoxicity by Expression of a Cloned Human Carbonyl Reductase cDNA in K562 Leukemia Cells", *Cancer Res.* (1995) 55:4646-4650.

Haase, A., et al. "Detection of Viral Nucleic Acids by in Situ Hybridization", *Methods in Virology* (1984) VII:189-226.

Hanefeld, U., et al. "One-pot Synthesis of Tetrasubstituted Pyrazoles Proof of Regiochemistry", *J. Chem. Soc. Perkin Trans.* (1996) 1:1545-1552.

Ishiyama, T., et al. "A Stoichiometric Aromatic C—H Borylation Catalyzed by Iridium(I)/2,2'-Bipyridine Complexes at Room Temperature", *Angew. Chem. Int. Ed.* (2002) 41(16):3056-3058.

Ishiyama, T., et al. "Mild Iridium-Catalyzed Borylation of Arenes. High Turnover Numbers, Room Temperature Reactions, and Isolation of a Potential Intermediate", *J. Am. Chem. Soc.* (2002) 124(3):390-391.

Kallberg, Y., et al. "Short-Chain Dehydrogenase/Reductase (SDR) Relationships: a Large Family with Eight Clusters Common to Human, Animal, and Plant Genomes", *Protein Sci.* (2002) 11:636-641.

Kallberg, Y., et al. "Short-Chain Dehydrogenases/Reductases (SDRs)", *Eur. J. Biochem.* (2002) 269:4409-4417.

Knight, et al. "A Pharmacological Map of the PI3-K Family Defines a Role for p110α in Insulin Signaling", *Cell* (2006) 125:733-747.

Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.

Kwok, B.H., et al. "The Anti-Inflammatory Natural Product Parthenolide from the Medicinal Herb Feverfew Directly Binds to and Inhibits IkB Kinase", *Chem. Biol.* (2001) 8:759-766.

Mayer, T.U., et al. "Small Molecule Inhibitor of Mitotic Spindle Bipolarity Identified in a Pheontype-Based Screen", *Science* (1999) 286:971-974.

Miyaura, N., et al. "Palladium-Catalyzed Cross-Coupling Reactions of Organoboron Compounds," *Chem. Rev.* (1995) 95(7):2457-2483.

Moon, H.S., et al. "A Novel Microtubule Destabilizing Entity from Orthogonal Synthesis of Triazine Library and Zebrafish Embryo Screening", *J. Am. Chem. Soc.* (2002) 124:11608-11609.

Nakanishi, M., et al. "Cloning and Sequence Analysis of a cDNA Encoding Tetrameric Carbonyl Reductase of Pig Lung", *Biochem. Biophys. Acta* (1993) 194(3):1311-1316.

Niswender, C.M., et al. "Protein Engineering of Protein Kinase A Catalytic Subunits Results in the Acquisition of Novel Inhibitor Sensitivity", *The Journal of Biological Chemistry* (2002) 277(32):28916-28922.

Nobel, C.S.I., et al. "Purification of Full-Length Recombinant Human and Rat Type 1 11β-hydroxysteroid Dehydrogenases with Retained Oxidoreductase Activities", *Protein Expr. Purif.* (2002) 26:349-356.

Oppermann, U.C., et al. "Forms and Functions of Human SDR Enzymes", *Chem. Biol. Interact.* (2001) 130-132(1-3):699-705.

Persson, C.G. "Glucocorticoids for Asthma—Early Contributions", *Pulm. Pharmacol.* (1989) 2:163-166.

Pudlo, J.S., et al. "Synthesis, Antiproliferative, and Antiviral Activity of Certain 4-Substituted and 4,5 Disubstituted 7-[1,3-Dihydroxy-2-propoxy)methyl]pyrrolo[2,3-d]pyrimidines", *J. Med. Chem.* (1990) 33:1984-1992.

Robertson, R.P. "Eicosandoids and Human Disease", *Harrison's Principles of Internal Medicine*, Isselbacher K.J., et al. (eds.), McGraw-Hill, New York City (1994) 1:431-435.

Romero, D.G., et al. "Cloning and Expression of the Bovine 11β-hydroxysteroid Dehydrogenase Type-2", *J. Steroid Biochm. Mol. Biol.* (2000) 72:231-237.

Singer, R.H., et al. "Optimization of in situ Hybridization Using Isotopic and Non-Isotopic Detection Methods", *Biotechniques* (1986) 4(3):230-250.

Soldan, M., et al. "Induction of Daunorubicin Carbonyl Reducing Enzymes by Daunorubicin in Sensitive and Resistant Pancreas Carcinoma Cells", *Biochem. Pharmacol.* (1996) 51:117-123.

Tanaka, M., et al. "An Unbiased Cell Morphology-Based Screen for New, Biologically Active Small Molecules", *PLoS Biology* (2005) 3(5):0764-0776.

Ugarkar, B.G., et al. "Adenosine Kinase Inhibitors. 2. Synthesis, Enzyme Inhibition, and Antiseizure Activity of Diaryltubercidin Analogues", *J. Med. Chem.* (2000) 43:2894-2905.

White, P.C., et al. "11β-Hydroxysteroid Dehydrogenase and the Syndrome of Apparent Mineralocorticoid Excess", *Endocr. Rev.* (1997) 18(1):135-156.

Widler, L., et al. "7-Alkyl- and 7-Cycloalkyl-5-aryl-pyrrolo[2,3-d]pyrimidines-Potent Inhibitors of the Tyrosine Kinase c-Src," *Bioorganic & Medicinal Chemistry Letters* (2001) 11(6):849-852.

Wolff, M. E. *Burger's Medicinal Chemistry*, 5ed, Part 1, John Wiley & Sons, 1995, pp. 975-977.

International Search Report dated Aug. 27, 2008 for International Application No. PCT/US07/08395, 4 pages.

Supplementary European Search Report dated Feb. 16, 2010 for EP Application No. 07754845, 4 pages.

International Search Report dated Sep. 25, 2008 for International Application No. PCT/US07/08355, 1 page.

International Search Report dated Oct. 2, 2006 for International Application No. PCT/US05/042524, 7 pages.

(56) References Cited

OTHER PUBLICATIONS

Bhat, G. A., et al., "Pyrazolopyrimidine nucleosides. 12. Synthesis and biological activity of certain pyrazolo[3,4-d]pyrimidine nucleosides related to adenosine," J. Med. Chem. vol. 24, No. 10, (1981), pp. 1165-1172.

Pietrie et al., "Novel biotinylated adenylate analogue derived from pyrazolo[3,4-d]pyrimidine for labeling DNA probes," Bioconj. Chem. vol. 2, No. 6, (1991), pp. 441-446.

Examination Report for GB Application No. GB0819947.3 dated Oct. 27, 2010, 2 pages.

Supplementary European Search Report dated Feb. 24, 2010 for EP Application No. 07754845, 4 pages.

International Search Report Dated Apr. 5, 2006 for international Application No. PCT/FR2005/051073, 3 pages.

European Search Report Dated Feb. 4, 2011 for EP Application No. 05857011.0, 5 pages.

| | IC$_{50}$ (µM) | | | |
|---|---|---|---|---|
| | p110α | p110β | p110δ | p110γ |
| PIK-293 | 100 | 25 | 0.24 | 10 |
| PIK-294 | 10 | 0.49 | 0.010 | 0.16 |
| Fold increase in potency | 10 | 50 | 24 | 62 |

PIK-293  (X = N, Y = C)
IC87114  (X = C, Y = N)

Figure 5.

|  | PIK23 | TGX115 | AMA37 | PIK39 | IC87114 | TGX286 | PIK75 | PIK90 | PIK93 | PIK108 | PI-103 | PIK124 | KU-55399 |
|---|---|---|---|---|---|---|---|---|---|---|---|---|---|
| PI3Ks | | | | | | | | | | | | | |
| p110α | >200 | 61 | 32 | >200 | >200 | 4.5 | 0.0058 | 0.011 | 0.039 | 2.6 | 0.008 | 0.023 | 3.3 |
| p110β | 42 | 0.13 | 3.7 | 11 | 16 | 0.12 | 1.3 | 0.35 | 0.59 | 0.057 | 0.088 | 1.1 | 1.2 |
| p110δ | 0.097 | 0.63 | 22 | 0.18 | 0.13 | 1 | 0.51 | 0.058 | 0.12 | 0.26 | 0.048 | 0.34 | 0.72 |
| p110γ | 50 | 100 | 100 | 17 | 61 | 10 | 0.076 | 0.018 | 0.016 | 4.1 | 0.15 | 0.054 | 9.9 |
| PI3KC2α | >100 | >100 | >100 | >100 | >100 | >100 | ~10 | 0.047 | ~16 | ~100 | ~1 | 0.14 | ND |
| PI3KC2β | 100 | 50 | >100 | 100 | >100 | ~100 | ~1 | 0.064 | 0.14 | ~20 | 0.026 | 0.37 | ND |
| PI3KC2γ | >100 | 100 | 50 | 100 | >100 | ND | ND | ND | ND | ND | ND | ND | ND |
| hsVPS34 | ~50 | 5.2 | >100 | >100 | >100 | 3.1 | 2.6 | 0.83 | 0.32 | ~5 | 2.3 | 10 | ~10 |
| PI4Ks | | | | | | | | | | | | | |
| PI4KIIα | >100 | >100 | >100 | >100 | >100 | >100 | >100 | >100 | >100 | >100 | >100 | >100 | >100 |
| PI4KIIIα | >100 | >100 | >100 | >100 | >100 | >100 | >100 | 0.83 | 1.1 | ~50 | >100 | >100 | >100 |
| PI4KIIIβ | >100 | >100 | >100 | >100 | >100 | >100 | ~50 | 3.1 | 0.019 | >100 | ~50 | >100 | >100 |
| PIKKs | | | | | | | | | | | | | |
| ATR | >100 | >100 | >100 | >100 | >100 | >100 | 21 | 15 | 17 | >100 | 0.85 | 2 | 20 |
| ATM | >100 | 20 | ND | >100 | >100 | >100 | 2.3 | 0.61 | 0.49 | 35 | 0.92 | 3.9 | 0.005 |
| DNA-PK | >100 | 1.2 | 0.27 | >100 | >100 | ~50 | 0.002 | 0.013 | 0.064 | 0.12 | 0.002 | 1.5 | 10 |
| mTORC1 | >100 | >100 | >100 | >100 | >100 | >100 | ~1 | 1.05 | 1.38 | ~10 | 0.02 | 9 | ~20 |
| mTORC2 | >101 | >100 | >100 | >100 | >100 | ND | ~10 | ND | ND | ND | 0.083 | ND | >100 |
| PIPKs | | | | | | | | | | | | | |
| PI4P5KIα | >100 | >100 | >100 | >100 | >100 | >100 | >100 | >100 | >100 | >100 | >100 | >100 | >100 |
| PI4P5KIβ | >100 | >100 | >100 | >100 | >100 | >100 | >100 | >100 | >100 | >100 | >100 | >100 | >100 |
| PI5P4KIIβ | >100 | >100 | >100 | >100 | >100 | >100 | >100 | >100 | >100 | >100 | >100 | >100 | ND |

Figure 6.

| | TGX115 | AMA37 | PIK39 | IC87114 | TGX286 | PIK75 | PIK90 | PIK93 | PI103 | PIK124 | KU55933 |
|---|---|---|---|---|---|---|---|---|---|---|---|
| Abl | 121.2 | 128.5 | 99.9 | 103.6 | 100.0 | 97.9 | 103.4 | 99.6 | 100.8 | 109.1 | 100.3 |
| Abl (T315I) | 141.2 | 127.4 | 110.5 | 99.4 | 108.5 | 121.6 | 111.3 | 126.0 | 108.1 | 87.5 | 105.3 |
| Akt1 | 126.6 | 125.7 | 136.4 | 122.2 | 114.0 | (10) | 140.2 | 112.6 | 108.5 | 94.8 | 114.0 |
| Akt1 (ΔPH) | 91.4 | 77.3 | 81.0 | 89.6 | 94.7 | (10) | 122.4 | 122.2 | 123.1 | 93.3 | 116.5 |
| Akt2 | 98.8 | 115.0 | 110.5 | 116.5 | 109.7 | 80.7 | 119.8 | 117.4 | 114.7 | 114.7 | 98.2 |
| Akt2 (ΔPH) | 104.4 | 94.4 | 111.3 | 117.8 | 117.3 | 95.0 | 108.5 | 110.7 | 112.6 | 98.7 | 100.2 |
| Akt3 | 97.6 | 106.6 | 94.2 | 111.0 | 102.9 | (2.9) | 113.3 | 96.4 | 103.5 | 93.0 | 95.1 |
| CamKII | 111.4 | 121.9 | 122.1 | 115.4 | 118.8 | 119.8 | 116.1 | 120.4 | 127.6 | 135.5 | 121.8 |
| CDK1/cyc.B | 103.0 | 114.0 | 115.5 | 116.0 | 120.3 | 61.6 | 126.6 | 124.5 | 142.3 | 110.7 | 101.2 |
| CDK2/cyc.A | 105.3 | 99.7 | 105.6 | 102.4 | 103.1 | (1.2) | 100.9 | 98.1 | 98.5 | 104.9 | 97.4 |
| Chk1 | 119.9 | 104.0 | 105.2 | 103.0 | 104.1 | 98.4 | 102.9 | 99.7 | 92.3 | 107.9 | 81.4 |
| CK1 | 99.7 | 99.2 | 100.1 | 98.1 | 91.3 | (3.0) | 97.8 | 100.2 | 84.8 | 104.6 | 94.1 |
| CK2 | 103.3 | 106.6 | 99.6 | 111.7 | 111.2 | 82.2 | 103.1 | 113.2 | 108.1 | 78.5 | 105.4 |
| Erk1 | 96.7 | 99.3 | 97.6 | 93.7 | 99.0 | 77.9 | 98.8 | 98.6 | 92.0 | 97.8 | 104.6 |
| Erk2 | 107.7 | 102.5 | 109.2 | 104.7 | 106.9 | 94.3 | 102.0 | 103.2 | 98.8 | 98.0 | 102.1 |
| FAK | 105.5 | 105.5 | 106.4 | 110.1 | 102.8 | (10) | 100.0 | 101.8 | 101.8 | 102.8 | 107.3 |
| Fyn | 145.7 | 131.3 | 115.7 | 105.3 | 111.3 | (10) | 126.1 | 127.2 | 114.2 | 113.4 | 116.0 |
| GRK2 | 113.5 | 117.3 | 112.6 | 118.7 | 118.1 | 115.6 | 120.2 | 110.9 | 110.3 | 87.8 | 108.6 |
| GSK3β | 114.0 | 107.3 | 101.5 | 104.7 | 96.1 | (4.4) | 85.6 | 104.0 | 105.5 | 97.6 | 102.0 |
| Hck | 104.9 | 102.2 | 101.1 | 93.0 | 84.9 | (10) | 94.7 | 94.9 | 94.9 | 87.2 | 104.1 |
| Insulin R. | 108.4 | 113.4 | 113.6 | 115.7 | 112.1 | 99.5 | 102.8 | 109.8 | 106.0 | 109.9 | 109.7 |
| JNK1α1 | 99.9 | 95.5 | 92.1 | 88.5 | 93.8 | 97.8 | 94.2 | 87.2 | 83.6 | 96.9 | 99.6 |
| JNK2α1 | 104.8 | 104.8 | 116.7 | 107.1 | 88.1 | 88.1 | 90.5 | 88.1 | 81.0 | 85.7 | 85.7 |
| JNK2α2 | 95.4 | 101.6 | 90.8 | 87.7 | 89.3 | 86.2 | 83.1 | 98.5 | 76.9 | 89.3 | 95.4 |
| IRAK4 | 112.7 | 98.9 | 100.1 | 93.1 | 95.0 | (0.9) | 94.9 | 95.9 | 105.6 | 175.4 | 74.2 |
| NEK2 | 125.2 | 99.1 | 98.6 | 114.3 | 126.4 | 106.9 | 103.4 | 110.1 | 120.0 | 118.5 | 106.5 |
| PKA | 105.4 | 94.0 | 108.1 | 108.6 | 107.3 | (10) | 103.1 | 105.6 | 102.5 | 104.3 | 104.1 |
| PKCδ | 103.9 | 104.9 | 103.9 | 104.6 | 104.9 | 114.3 | 100.7 | 103.7 | 101.2 | 105.5 | 103.7 |
| PKCε | 108.9 | 111.9 | 111.9 | 114.1 | 111.5 | (10) | 105.2 | 103.4 | 103.4 | 106.0 | 104.8 |
| PDK1 | 111.2 | 101.9 | 97.4 | 113.4 | 114.4 | 111.0 | 110.4 | 118.7 | 107.5 | 109.4 | 130.7 |
| PLK1 | 122.7 | 118.9 | 117.4 | 109.6 | 107.6 | 93.7 | 107.6 | 111.1 | 106.2 | 96.0 | 84.9 |
| p38 | 101.2 | 102.8 | 106.5 | 104.1 | 100.9 | 100.3 | 98.5 | 102.9 | 99.8 | 102.6 | 101.4 |
| Src | 111.7 | 109.0 | 109.6 | 113.3 | 96.4 | (10) | 103.7 | 116.1 | 100.6 | 102.7 | 114.7 |
| Src (T338I) | 112.8 | 101.3 | 97.9 | 95.7 | 96.4 | 80.4 | 109.5 | 111.5 | 113.4 | 112.5 | 113.0 |
| WNK1 | 107.5 | 108.0 | 109.6 | 109.0 | 119.3 | 101.1 | 108.6 | 110.0 | 104.1 | 108.3 | 104.7 |
| Zap70 | 123.8 | 121.1 | 130.4 | 110.5 | 130.0 | 179.5 | 115.8 | 115.4 | 117.7 | 100.4 | 99.3 |

Figure 7.

```
   1 MPPGVDCPME FWTKEENQSV VVDFLLPTGV YLNFPVSRNA NLSTIKQLLW HRAQYEPLFH
  61 MLSGPEAYVF TCINQTAEQQ ELEDEQRRLC DVQPFLPVLR LVAREGDRVK KLINSQISLL
 121 IGKGLHEFDS LCDPEVNDFR AKMCQFCEEA AARRQQLGWE AWLQYSFPLQ LEPSAQTWGP
 181 GTLRLPNRAL LVNVKFEGSE ESFTFQVSTK DVPLALMACA LRKKATVFRQ PLVEQPEDYT
 241 LQVNGRHEYL YGNYPLCQFQ YICSCLHSGL TPHLTMVHSS SILAMRDEQS NPAPQVQKPR
 301 AKPPPIPAKK PSSVSLWSLE QPFRIELIQG SKVNADERMK LVVQAGLFHG NEMLCKTVSS
 361 SEVSVCSEPV WKQRLEFDIN ICDLPRMARL CFALYAVIEK AKKARSTKKK SKKADCPIAW
 421 ANLMLFDYKD QLKTGERCLY MWPSVPDEKG ELLNPTGTVR SNPNTDSAAA LLICLPEVAP
 481 HPVYYPALEK ILELGRHSEC VHVTEEEQLQ LREILERRGS GELYEHEKDL VWKLRHEVQE
 541 HFPEALARLL LVTKWNKHED VAQMLYLLCS WPELPVLSAL ELLDFSFPDC HVGSFAIKSL
 601 RKLTDDELFQ YLLQLVQVLK YESYLDCELT KFLLDRALAN RKIGHFLFWH LRSEMHVPSV
 661 ALRFGLILEA YCRGSTHHMK VLMKQGEALS KLKALNDFVK LSSQKTPKPQ TKELMHLCMR
 721 QEAYLEALSH LQSPLDPSTL LAEVCVEQCT FMDSKMKPLW IMYSNEEAGS GGSVGIIFKN
 781 GDDLRQDMLT LQMIQLMDVL WKQEGLDLRM TPYGCLPTGD RTGLIEVVLR SDTIANIQLN
 841 KSNMAATAAF NKDALLNWLK SKNPGEALDR AIEEFTLSCA GYCVATYVLG IGDRHSDNIM
 901 IRESGQLFHI DFGHFLGNFK TKFGINRERV PFILTYDFVH VIQQGKTNNS EKFERFRGYC
 961 ERAYTILRRH GLLFLHLFAL MRAAGLPELS CSKDIQYLKD SLALGKTEEE ALKHFRVKFN
1021 EALRESWKTK VNWLAHNVSK DNRQ
           (SEQ ID NO:3)
```

Figure 8.

```
   1    melenykqpv vlredncrrr rrmkprsaaa slssmelipi efvlptsqrk ckspetallh
  61    vaghgnveqm kaqvwlrale tsvaadfyhr lgphhfllly qkkgqwyeiy dkyqvvqtld
 121    clrywkathr spgqihlvqr hppseesqaf qrqltaligy dvtdvsnvhd deleftrrgl
 181    vtprmaevas rdpklyamhp wvtskplpey lwkkianncl fivihrstts qtikvspddt
 241    pgailqsfft kmakkkslmd ipesqseqdf vlrvcgrdey lvgetpiknf qwvrhclkng
 301    eeihvvldtp pdpaldevrk eewplvddct gvtgyheqlt ihgkdhesvf tvslwdcdrk
 361    frvkirgidi pvlprntdlt vfveaniqhg qqvlcqrrts pkpfteevlw nvwlefsiki
 421    kdlpkgalln lqiycgkapa lsskasaesp sseskgkvql lyyvnlllid hrfllrrgey
 481    vlhmwqisgk gedqgsfnad kltsatnpdk ensmsisill dnychpialp khqptpdpeg
 541    drvraempnq lrkqleaiia tdplnpltae dkellwhfry eslkhpkayp klfssvkwgq
 601    qeivaktyql larrevwdqs aldvgltmql ldcnfsdenv raiavqkles ledddvlhyl
 661    lqlvqavkfe pyhdsalarf llkrglrnkr ighflfwflr seiaqsrhyq qrfavileay
 721    lrgcgtamlh dftqqvqvie mlqkvtldik slsaekydvs sqvisqlkqk lenlqnsqlp
 781    esfrvpydpg lkagalaiek ckvmaskkkp lwlefkcadp talsnetigi ifkhgddlrq
 841    dmlilqilri mesiwetesl dlcllpygci stgdkigmie ivkdattiak iqqstvgntg
 901    afkdevlnhw lkekspteek fqaaverfvy scagycvatf vlgigdrhnd nimitetgnl
 961    fhidfghilg nyksflgink ervpfvltpd flfvmgtsgk ktsphfqkfq dicvkaylal
1021    rhhtnlliil fsmmlmtgmp qltskediey irdaltvgkn eedakkyfld qievcrdkgw
1081    tvqfnwflhl vlgikqgekh sa
           (SEQ ID NO:4)
```

Figure 9.

```
   1   MPPRPSSGEL WGIHLMPPRI LVECLLPNGM IVTLECLREA TLITIKHELF KEARKYPLHQ
  61   LLQDESSYIF VSVTQEAERE EFFDETRRLC DLRLFQPFLK VIEPVGNREE KILNREIGFA
 121   IGMPVCEFDM VKDPEVQDFR RNILNVCKEA VDLRDLNSPH SRAMYVYPPN VESSPELPKH
 181   IYNKLDKGQI IVVIWVIVSP NNDKQKYTLK INHDCVPEQV IAEAIRKKTR SMLLSSEQLK
 241   LCVLEYQGKY ILKVCGCDEY FLEKYPLSQY KYIRSCIMLG RMPNLMLMAK ESLYSQLPMD
 301   CFTMPSYSRR ISTATPYMNG ETSTKSLWVI NSALRIKILC ATYVNVNIRD IDKIYVRTGI
 361   YHGGEPLCDN VNTQRVPCSN PRWNEWLNYD IYIPDLPRAA RLCLSICSVK GRKGAKEEHC
 421   PLAWGNINLF DYTDTLVSGK MALNLWPVPH GLEDLLNPIG VTGSNPNKET PCLELEFDWF
 481   SSVVKFPDMS VIEEHANWSV SREAGFSYSH AGLSNRLARD NELRENDKEQ LKAISTRDPL
 541   SEITEQEKDF LWSHRHYCVT IPEILPKLLL SVKWNSRDEV AQMYCLVKDW PPIKPEQAME
 601   LLDCNYPDPM VRGFAVRCLE KYLTDDKLSQ YLIQLVQVLK YEQYLDNLLV RFLLKKALTN
 661   QRIGHFFFWH LKSEMHNKTV SQRFGLLLES YCRACGMYLK HLNRQVEAME KLINLTDILK
 721   QEKKDETQKV QMKFLVEQMR RPDFMDALQG FLSPLNPAHQ LGNLRLEECR IMSSAKRPLW
 781   LNWENPDIMS ELLFQNNEII FKNGDDLRQD MLTLQIIRIM ENIWQNQGLD LRMLPYGCLS
 841   IGDCVGLIEV VRNSHTIMQI QCKGGLKGAL QFNSHTLHQW LKDKNKGEIY DAAIDLFTRS
 901   CAGYCVATFI LGIGDRHNSN IMVKDDGQLF HIDFGHFLDH KKKKFGYKRE RVPFVLTQDF
 961   LIVISKGAQE CTKTREFERF QEMCYKAYLA IRQHANLFIN LFSMMLGSGM PELQSFDDIA
1021   YIRKTLALDK TEQEALEYFM KQMNDAHHGG WTTKMDWIFH TIKQHALN (SEQ ID NO:5)
```

Figure 10.

```
   1   MCFSFIMPPA MADILDIWAV DSQIASDGSI PVDFLLPTGI YIQLEVPREA TISYIKQMLW
  61   KQVHNYPMFN LLMDIDSYMF ACVNQTAVYE ELEDETRRLC DVRPFLPVLK LVTRSCDPGE
 121   KLDSKIGVLI GKGLHEFDSL KDPEVNEFRR KMRKFSEEKI LSLVGLSWMD WLKQTYPPEH
 181   EPSIPENLED KLYGGKLIVA VHFENCQDVF SFQVSPNMNP IKVNELAIQK RLTIHGKEDE
 241   VSPYDYVLQV SGRVEYVFGD HPLIQFQYIR NCVMNRALPH FILVECCKIK KMYEQEMIAI
 301   EAAINRNSSN LPLPLPPKKT RIISHVWENN NPFQIVLVKG NKLNTEETVK VHVRAGLFHG
 361   TELLCKTIVS SEVSGKNDHI WNEPLEFDIN ICDLPRMARL CFAVYAVLDK VKTKKSTKTI
 421   NPSKYQTIRK AGKVHYPVAW VNTMVFDFKG QLRTGDIILH SWSSFPDELE EMLNPMGTVQ
 481   TNPYTENATA LHVKFPENKK QPYYYPPFDK IIEKAAEIAS SDSANVSSRG GKKFLPVLKE
 541   ILDRDPLSQL CENEMDLIWT LRQDCREIFP QSLPKLLLSI KWNKLEDVAQ LQALLQIWPK
 601   LPPREALELL DFNYPDQYVR EYAVGCLRQM SDEELSQYLL QLVQVLKYEP FLDCALSRFL
 661   LERALGNRRI GQFLFWHLRS EVHIPAVSVQ FGVILEAYCR GSVGHMKVLS KQVEALNKLK
 721   TLNSLIKLNA VKLNRAKGKE AMHTCLKQSA YREALSDLQS PLNPCVILSE LYVEKCKYMD
 781   SKMKPLWLVY NNKVFGEDSV GVIFKNGDDL RQDMLTLQML RLMDLLWKEA GLDLRMLPYG
 841   CLATGDRSGL IEVVSTSETI ADIQLNSSNV AAAAAFNKDA LLNWLKEYNS GDDLDRAIEE
 901   FTLSCAGYCV ASYVLGIGDR HSDNIMVKKT GQLFHIDFGH ILGNFKSKFG IKRERVPFIL
 961   TYDFIHVIQQ GKTGNTEKFG RFRQCCEDAY LILRRHGNLF ITLFALMLTA GLPELTSVKD
1021   IQYLKDSLAL GKSEEEALKQ FKQKFDEALR ESWTTKVNWM AHTVRKDYRS (SEQ ID NO:6)
```

US 8,642,604 B2

SUBSTITUTED PYRAZOLO[3,2-D]PYRIMIDINES AS ANTI-CANCER AGENTS

CROSS-REFERENCES TO RELATED APPLICATIONS

This application is a continuation of U.S. patent application Ser. No. 11/732,856, filed Apr. 4, 2007, which issued as U.S. Pat. No. 7,585,868 on Sep. 8, 2009, which in turn claims the benefit of U.S. Provisional Patent Application No. 60/744,269, filed Apr. 4, 2006, and U.S. Provisional Patent Application No. 60/744,270, filed Apr. 4, 2006, all of which are incorporated herein by reference in their entirety for all purposes.

STATEMENT AS TO RIGHTS TO INVENTIONS MADE UNDER FEDERALLY SPONSORED RESEARCH AND DEVELOPMENT

The present invention was supported by a grant from the National Institutes of Health (AI44009). The Government has certain rights to the invention.

BACKGROUND OF THE INVENTION

Phosphoinositide 3-kinases (PI3-Ks) catalyze the synthesis of the phosphatidylinositol (PI) second messengers PI(3)P, PI(3,4)P2, and PI(3,4,5)P3 (PIP3) (Fruman et al., 1998). In the appropriate cellular context, these three lipids control diverse physiological processes including cell growth, survival, differentiation and chemotaxis (Katso et al., 2001). The PI3-K family comprises 15 kinases with distinct substrate specificities, expression patterns, and modes of regulation (Katso et al., 2001). The class I PI3-Ks (p110α, p110β, p110δ, and p110γ) are activated by tyrosine kinases or G-protein coupled receptors to generate PIP3, which engages downstream effectors such as the Akt/PDK1 pathway, the Tec family kinases, and the Rho family GTPases. The class II and III PI3-Ks play a key role in intracellular trafficking through the synthesis of PI(3)P and PI(3,4)P2. The PIKKs are protein kinases that control cell growth (mTORC1) or monitor genomic integrity (ATM, ATR, DNA-PK, and hSmg-1).

The importance of these enzymes in diverse pathophysiology has made the PI3-K family the focus of intense interest as a new class of drug targets (Ward et al., 2003). This interest has been fueled by the recent discovery that p110α is frequently mutated in primary tumors (Samuels et al., 2004) and evidence that the lipid phosphatase PTEN, an inhibitor of PI3-K signaling, is a commonly inactivated tumor suppressor (Cantley and Neel, 1999). Efforts are underway to develop small molecule PI3-K inhibitors for the treatment of inflammation and autoimmune disease (p110δ, p110γ, and mTOR), thrombosis (p110β), viral infection (the PIKKs) and cancer (p110α, mTOR, and others). Recently, the first selective inhibitors of these enzymes have been reported (Camps et al., 2005; Condliffe et al., 2005; Jackson et al., 2005; Knight et al., 2004; Lau et al., 2005; Sadhu et al., 2003).

Protein tyrosine kinases, protein serine/threonine kinases, and lipid kinases are distinct classes of proteins that play critical roles in regulation and proliferation of cellular activity. Small molecules that inhibit these protein classes have the potential to disrupt dysfunctional/pathological pathways at two distinct points. For example, signaling through tyrosine kinase receptors is known to be disregulated in several types of cancer. This signaling pathway involves downstream proteins such as PI3 Kinase. Signaling through the serine/threonine protein kinase mTOR (also known as the mammalian target of rapamycin) is known to regulate cell growth, cell proliferation, cell motility, cell survival, protein synthesis, and transcription. Disruption of the mTOR pathway is implicated as a contributing factor to various human disease processes, especially various types of cancer. An inhibitor that blocks activity of protein tyrosine kinase and PI3 Kinase, mTOR and PI3Kinase, or mTOR, protein tyrosine kinase and PI3 Kinase, has the potential to stop the aberrant signaling at two or three different levels. Double or triple inhibition by a small molecule may magnify drug potency, increasing the compound's therapeutic potential.

The present invention meets these and other needs in the art by providing a new class of PI3 kinase antagonists, PI3 kinase and tryosine kinase antagonists, PI3Kinase and mTOR antagonists, and PI3Kinase, mTOR and tryosine kinase antagonists.

BRIEF SUMMARY OF THE INVENTION

It has been discovered that certain compounds described herein are potent antagonists of PI3 kinase, PI3 kinase and tryosine kinase, PI3Kinase and mTOR, or PI3Kinase, mTOR and tryosine kinase.

In one aspect, the present invention provides novel kinase antagonists that are PI3-Kinase affinity pocket binding antagonists (e.g. a PI3-Kinase affinity pocket binding pyrazolopyrimidine antagonist or a PI3-Kinase affinity pocket binding pyrrolopyrimidine antagonist). The PI3-Kinase affinity pocket binding antagonist is a compound containing a PI3-Kinase affinity pocket binding moiety. The PI3-Kinase affinity pocket binding pyrazolopyrimidine antagonists of the present invention are substituted pyrazolopyrimidine compounds containing a PI3-Kinase affinity pocket binding moiety. Likewise, the PI3-Kinase affinity pocket binding pyrrolopyrimidine antagonists of the present invention are substituted pyrrolopyrimidine compounds containing a PI3-Kinase affinity pocket binding moiety.

In another aspect, the present invention provides the novel kinase antagonists of Formula (I), defined below.

In another aspect, the present invention provides methods of decreasing the catalytic activity of a PI3 Kinase (e.g. a p110δ kinase). The method includes the step of contacting said PI3 kinase with an activity decreasing amount of a compound of the present invention (i.e. a PI3-Kinase affinity pocket binding antagonists, or an antagonist of Formula I).

In another aspect, the present invention provides a method of treating a condition mediated by PI3 kinase activity, PI3 Kinase activity and tyrosine Kinase Activity, PI3 Kinase activity and mTOR activity, or PI3 Kinase activity, tyrosine kinase activity, and mTOR activity in a subject in need of such treatment. The method includes administering to the subject a therapeutically effective amount of a compound of the present invention (i.e. a PI3-Kinase affinity pocket binding antagonists, or an antagonist of Formula I).

BRIEF DESCRIPTION OF THE DRAWINGS

FIG. 5. IC50 values (μM) for selected PI3-K inhibitors against lipid kinases.

FIG. 6. Inhibition of protein kinases by PI3-K inhibitors. Values represent % activity remaining in the presence of 10 μM inhibitor. Values are average of triplicate measurements. IC50 values are in parenthesis where appropriate (μM).

FIG. 7 sets forth the sequence of a human p110δ kinase (SEQ ID NO:3).

FIG. 8 sets forth the sequence of a human p110γ kinase (SEQ ID NO:4).

FIG. 9 sets forth the sequence of a human p110α kinase (SEQ ID NO:5).

FIG. 10 sets forth the sequence of a human p110β kinase (SEQ ID NO:6).

DETAILED DESCRIPTION OF THE INVENTION

I. Definitions

Figure 1:
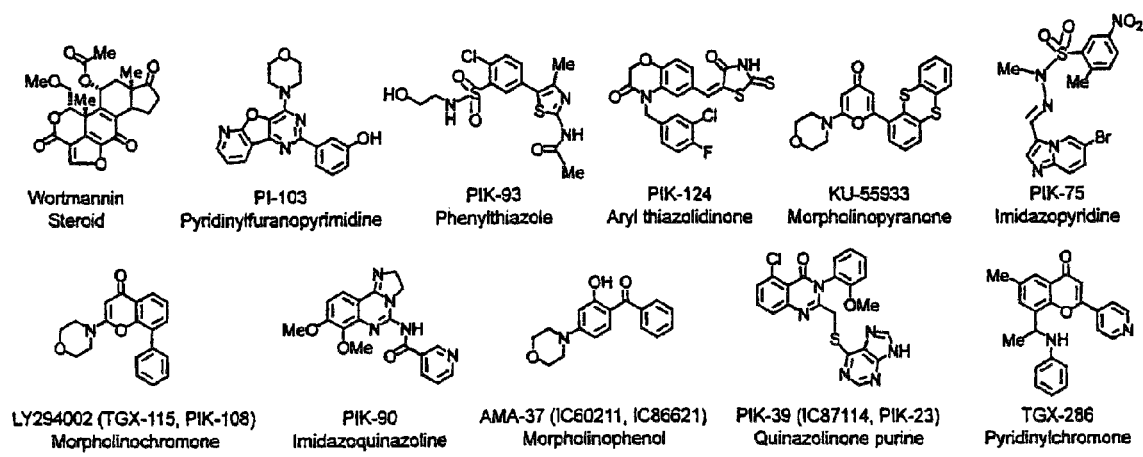
FIG. 1 illustrates structures of representative compounds from eleven chemotypes of PI3-K inhibitors.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2$O— is equivalent to —O$CH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —$CH_2CH_2CH_2CH_2$—, —$CH_2$CH=CHCH$_2$—, —$CH_2$C≡C$CH_2$—, —$CH_2CH_2$CH($CH_2CH_2CH_3$)$CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together (e.g. naphthyl) or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 6-isoquinolyl, 2-quinoxalinyl, 5-quinoxalinyl, 3-quinolyl, and 6-quinolyl. Thus, the term "heteroaryl" include fused ring structures in which at least one ring includes at least two double bonds. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" referrers to a carbon or heteroatom.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen radical. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer.

An "effective amount" is an amount sufficient to contribute to the treatment, prevention, or reduction of a symptom or symptoms of a disease. An "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, or reducing the likelihood of the onset (or reoccurrence) of a disease or its symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an osteoclast or leukocyte relative to the absence of the antagonist.

As used herein, the "antagonist" or "the compound of the present invention" refers to a compound of Formula (I), or a PI3-Kinase affinity pocket binding antagonist (e.g. a PI3-Kinase affinity pocket binding pyrazolopyrimidine antagonists, or a PI3-Kinase affinity pocket binding pyrrolopyrimidine antagonist). A "compound of Formula (I)" includes the compounds of Formulae (I)-(X) as described below.

II. Kinase Antagonists

In one aspect, the present invention provides novel kinase antagonists. The kinase antagonists may be a PI3-Kinase affinity pocket binding antagonist (e.g. a PI3-Kinase affinity pocket binding pyrazolopyrimidine antagonist, or PI3-Kinase affinity pocket binding pyrrolopyrimidine antagonist) or a compound of Formula (I). The PI3-Kinase affinity pocket binding antagonists of the present invention are compounds containing a PI3-Kinase affinity pocket binding moiety. The PI3-Kinase affinity pocket binding pyrazolopyrimidine antagonists of the present invention are substituted pyrazolopyrimidine compounds containing a PI3-Kinase affinity pocket binding moiety. Likewise, the PI3-Kinase affinity pocket binding pyrrolopyrimidine antagonists of the present invention are substituted pyrrolopyrimidine compounds containing a PI3-Kinase affinity pocket binding moiety.

The PI3-Kinase affinity pocket binding moiety is a substituent which, upon contacting a p110α, p110β, p110γ, or p110δ kinase, fills space within the corresponding PI3-Kinase affinity pocket. In some embodiments, the PI3-Kinase affinity pocket binding moiety displaces at least one water molecule within the PI3-Kinase affinity pocket. The PI3-Kinase affinity pocket binding moiety may also interact with one or more amino acids that from part of the PI3-Kinase affinity pocket. A description of the PI3-Kinase affinity pocket and methods of determining whether a substituent fills space within the PI3-Kinase affinity pocket are set forth below.

In some embodiments, the kinase antagonist of the present invention has the formula:

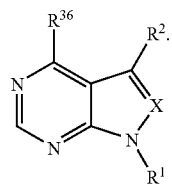

(I)

In Formula (I), $R^1$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X is =N— or =C(H)—. $R^{36}$ is halogen, —$NR^{37}R^{38}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{37}$ and $R^{38}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{37}$ and $R^{38}$ are independently hydrogen, or unsubstituted alkyl. $R^2$ may be a PI3-Kinase affinity pocket binding moiety.

In some embodiments, $R^{36}$ is —$NH_2$. Thus, the kinase antagonist may have the formula:

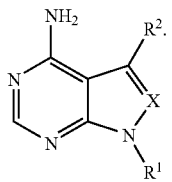

(II)

In some embodiments, $R^1$, $R^2$, and X are as defined above in Formula (I). In certain embodiments, X is =N—.

In some embodiments of Formulae (I) and (II), $R^1$ is hydrogen, $R^3$-substituted or unsubstituted alkyl, $R^3$-substituted or unsubstituted heteroalkyl, $R^3$-substituted or unsubstituted cycloalkyl, $R^3$-substituted or unsubstituted heterocycloalkyl, $R^3$-substituted or unsubstituted aryl, or $R^3$-substituted or unsubstituted heteroaryl. $R^2$ is halogen, $R^4$-substituted aryl, or substituted or unsubstituted heteroaryl;

$R^3$ is halogen, —CN, —$OR^5$, —$S(O)_nR^6$, —$NR^7R^8$, —$C(O)R^9$, =N—$NH_2$, —$NR^{10}$—$C(O)R^{11}$, —$NR^{12}$—C(O)—$OR^{13}$, —$C(O)NR^{14}R^{15}$, —$NR^{16}S(O)_2R^{17}$, —$S(O)_2NR^{18}$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl. Then symbol n is an integer from 0 to 2.

$R^4$ is halogen, —CN, —$OR^{20}$—$S(O)_qR^{21}$, —$NR^{22}R^{23}$, $C(O)R^{24}$, =N—$NH_2$, —$NR^{25}$—$C(O)R^{26}$, —$R^{27}$—C(O)—$OR^{28}$, —$C(O)NR^{29}R^{30}$, —$NR^{31}S(O)_2R^{32}$, —$S(O)_2NR^{33}$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. The symbol q represents an integer from 0 to 2.

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$ are independently hydrogen, $R^{35}$-substituted or unsubstituted alkyl, $R^{35}$-substituted or unsubstituted heteroalkyl, unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. $R^{19}$, $R^{34}$ and $R^{35}$ are independently hydrogen, halogen, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$ are independently hydrogen, unsubstituted alkyl, unsubstituted heteroalkyl, unsubstituted cycloalkyl, unsubstituted heterocycloalkyl, unsubstituted aryl, or unsubstituted heteroaryl. $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$ may independently be hydrogen, unsubstituted alkyl, or unsubstituted heteroalkyl.

$R^1$ may be $R^3$-substituted or unsubstituted alkyl, $R^3$-substituted or unsubstituted cycloalkyl, or $R^3$-substituted or unsubstituted aryl. $R^1$ may also be $R^3$-substituted or unsubstituted alkyl, or $R^3$-substituted or unsubstituted cycloalkyl. In some embodiments, $R^1$ is $R^3$-substituted or unsubstituted $C_1$-$C_4$ alkyl, or $R^3$-substituted or unsubstituted $C_3$-$C_6$ cycloalkyl. In other embodiments, $R^1$ is $R^3$-substituted or unsubstituted $C_1$-$C_4$ alkyl, or $R^3$-substituted or unsubstituted cyclopentyl. $R^1$ may also be methyl or unsubstituted $C_3$-$C_6$ branched alkyl (e.g. isopropyl, isobutyl, etc.).

In certain embodiments, $R^3$ is $R^{19}$-substituted or unsubstituted alkyl, $R^{19}$-substituted or unsubstituted cycloalkyl, or $R^{19}$-substituted or unsubstituted aryl. $R^3$ may also be $R^{19}$-substituted or unsubstituted alkyl, $R^{19}$-substituted or unsubstituted cycloalkyl, or $R^{19}$-substituted or unsubstituted aryl. In some embodiments, $R^3$ is $R^{19}$-substituted or unsubstituted alkyl, or $R^{19}$-substituted or unsubstituted cycloalkyl.

$R^{19}$ may be unsubstituted alkyl or unsubstituted cycloalkyl. In come embodiments, $R^{19}$ is unsubstituted $C_1$-$C_4$ alkyl or unsubstituted cyclopentyl.

In some embodiments, $R^2$ is $R^4$-substituted aryl, or $R^4$-substituted or unsubstituted heteroaryl. $R^2$ may be $R^4$-substituted phenyl, $R^4$-substituted or unsubstituted naphthyl, $R^4$-substituted or unsubstituted pyridinyl, $R^4$-substituted or unsubstituted pyrimidinyl, $R^4$-substituted or unsubstituted thiophenyl, $R^4$-substituted or unsubstituted furanyl, $R^4$-substituted or unsubstituted indolyl, $R^4$-substituted or unsubstituted benzoxadiazolyl, $R^4$-substituted or unsubstituted benzodioxolyl, $R^4$-substituted or unsubstituted benzodioxanyl, $R^4$-substituted or unsubstituted thianaphthanyl, $R^4$-substituted or unsubstituted pyrrolopyridinyl, $R^4$-substituted or unsubstituted indazolyl, $R^4$-substituted or unsubstituted tetrahydronaphthalenyl, $R^4$-substituted or unsubstituted quinolinyl, $R^4$-substituted or unsubstituted quinoxalinyl, $R^4$-substituted or unsubstituted pyridopyrazinyl, $R^4$-substituted or unsubstituted quinazolinonyl, $R^4$-substituted or unsubstituted chromenonyl, $R^4$-substituted or unsubstituted benzoisoxazolyl, $R^4$-substituted or unsubstituted imidazopyridinyl, $R^4$-substituted or unsubstituted benzofuranyl, $R^4$-substituted or unsubstituted dihydro-benzofuranyl, $R^4$-substituted or unsubstituted dihydro-benzodioxinyl, $R^4$-substituted or unsubstituted benzoimidazolonyl, or $R^4$-substituted or unsubstituted benzothiophenyl.

In certain embodiments, $R^2$ is $R^4$-substituted phenyl, $R^4$-substituted or unsubstituted pyrrolepyridinyl, $R^4$-substituted or unsubstituted quinolinyl, $R^4$-substituted or unsubstituted indazolyl, $R^4$-substituted or unsubstituted quinolinyl indolyl, or $R^4$-substituted or unsubstituted naphthyl. $R^4$ may be halogen, —CN, —$OR^{20}$, or —$NR^{22}R^{23}$. $R^4$ may also simply be halogen, or —$OR^{20}$.

In certain embodiments, $R^2$ is has the formula:

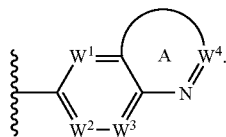

(III)

In Formula (III), $W^1$, $W^2$, $W^3$, and $W^4$ are independently =CH—, =$CR^4$—, or =N-. Each $R^4$ is as defined above in the description of Formulae (I) and (II). Ring A is a substituted or unsubstituted heteroaryl or substituted or unsubstituted heterocycloalkyl. In some embodiments, ring A is a 6 to 7 membered heterocycloalkyl or 6 to 7 membered heteroaryl. Thus, in some embodiments, ring A is partially or fully unsaturated 6- or 7-membered ring.

$R^{20}$ may be hydrogen or unsubstituted $C_1$-$C_{10}$ alkyl. In some embodiments, $R^{20}$ is hydrogen or unsubstituted $C_1$-$C_4$ alkyl. $R^{20}$ may also simply be hydrogen or methyl.

In some embodiments, $R^2$ has the formula:

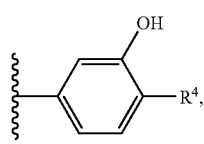

(IV)

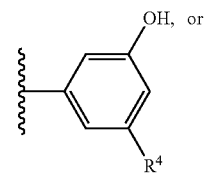

(V)

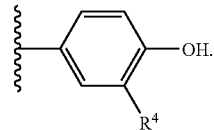

(VI)

In Formulae (IV), (V) and (VI), $R^4$ is absent, halogen, unsubstituted $C_1$-$C_4$ alkyl, or —$OR^{20}$. The halogen may be F, Cl, or Br. In some embodiments, the halogen is F or Cl. In other embodiments, the halogen is F. $R^{20}$ may be hydrogen or unsubstituted $C_1$-$C_4$ alkyl.

In some embodiments, $R^2$ is 6-hydroxynaphthyl, unsubstituted 7-azaindole, unsubstituted indolyl, unsubstituted indazolyl, or unsubstituted quinolinyl.

In some embodiments, $R^2$ has the formula:

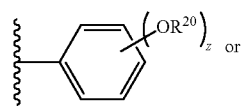

(VII)

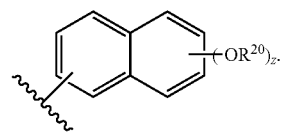

(VIII)

In Formulae (VII) and (VIII), $R^{20}$ is as defined above. It is noted that, in accordance with the description of $R^{20}$ above, each $R^{20}$ is optionally different. The symbol z is an integer from 1 to 5 (e.g. 1 or 2). In some embodiments, $R^{20}$ is hydrogen or unsubstituted $C_1$-$C_{10}$ alkyl (e.g. $C_1$-$C_5$ alkyl such as methyl or ethyl).

In some embodiments, $R^2$ has the formula:

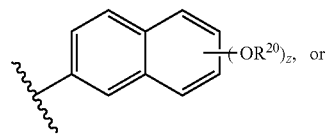

(IX)

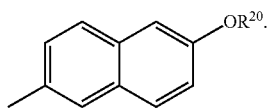

(X)

In Formulae (IX) and (X), above, $R^{20}$ is as defined above, for example, in the description of Formulae (I), (II), (VI), and (VII) above.

In some embodiments, each substituted group described above for the compounds of the present invention is substituted with at least one substituent group. More specifically, in some embodiments, each substituted alkyl, substituted heteroalkyl, substituted cycloalkyl, substituted heterocycloalkyl, substituted aryl, substituted heteroaryl, aryl($C_1$-$C_6$) alkyl, and heteroaryl($C_1$-$C_6$)alkyl described above is substituted with at least one substituent group. In other embodiments, at least one or all of these groups are substituted with at least one size-limited substituent group. Alternatively, at least one or all of these groups are substituted with at least one lower substituent group.

In other embodiments of the compounds described above, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In another embodiment, the compounds of Formula (I) include any or all of the compounds listed in Table 1 below.

III. The PI3-Kinase Affinity Pocket

Figure 2A:
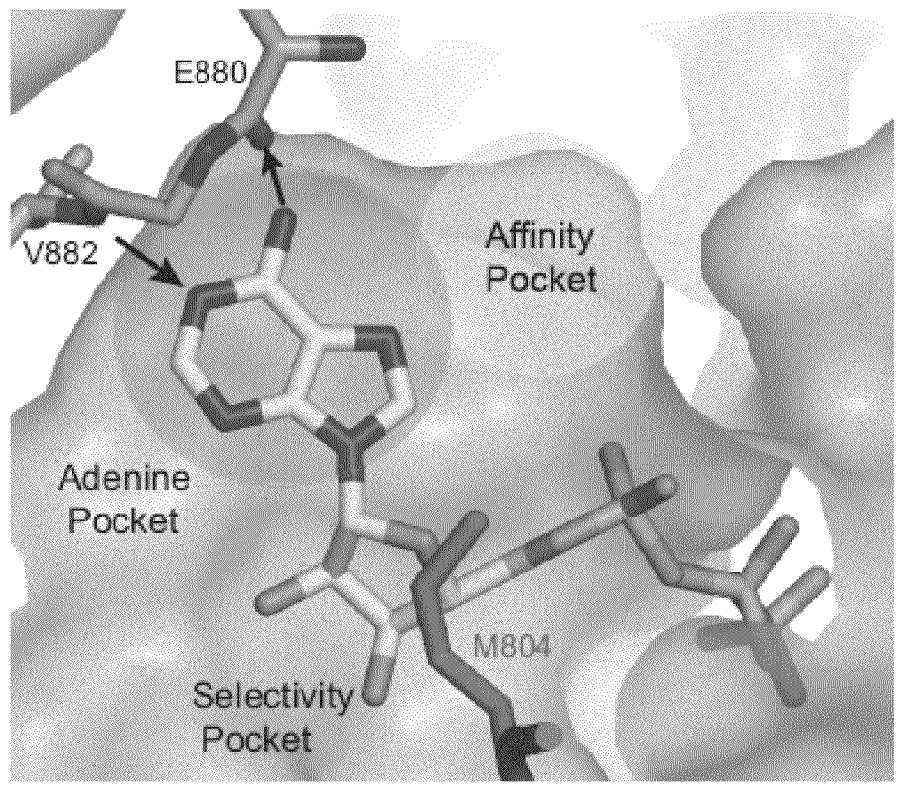
FIG. 2 illustrates structures of isoform-selective PI3-K inhibitors. A. Structure of ATP in the active site of p110γ, highlighting different regions of the ATP binding pocket. B. An alignment of all reported PI3-K inhibitor co-crystal structures. Met 804 adopts an up conformation in all structures except PIK-39. C. Structures or models of isoform-selective PI3-K inhibitors bound to p110γ. D. Structures or models of multi-targeted PI3-K inhibitors bound to p110γ.
Figure 2B:
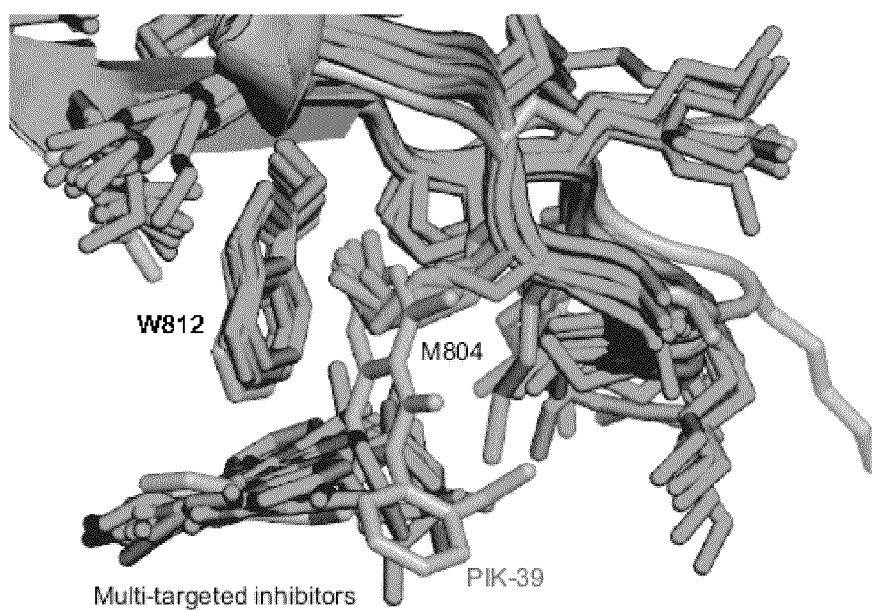
Figure 2C:
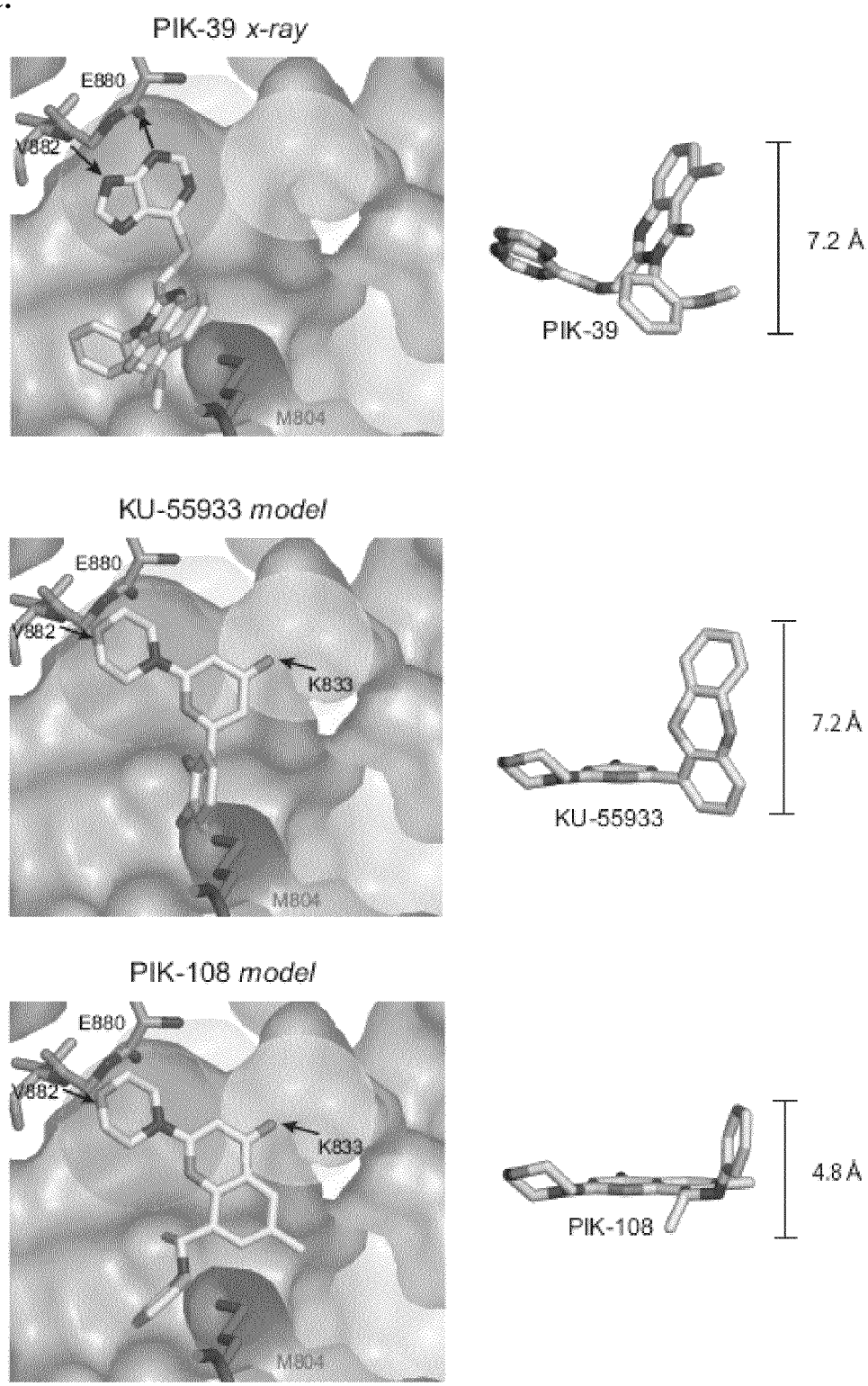
Figure 2D:
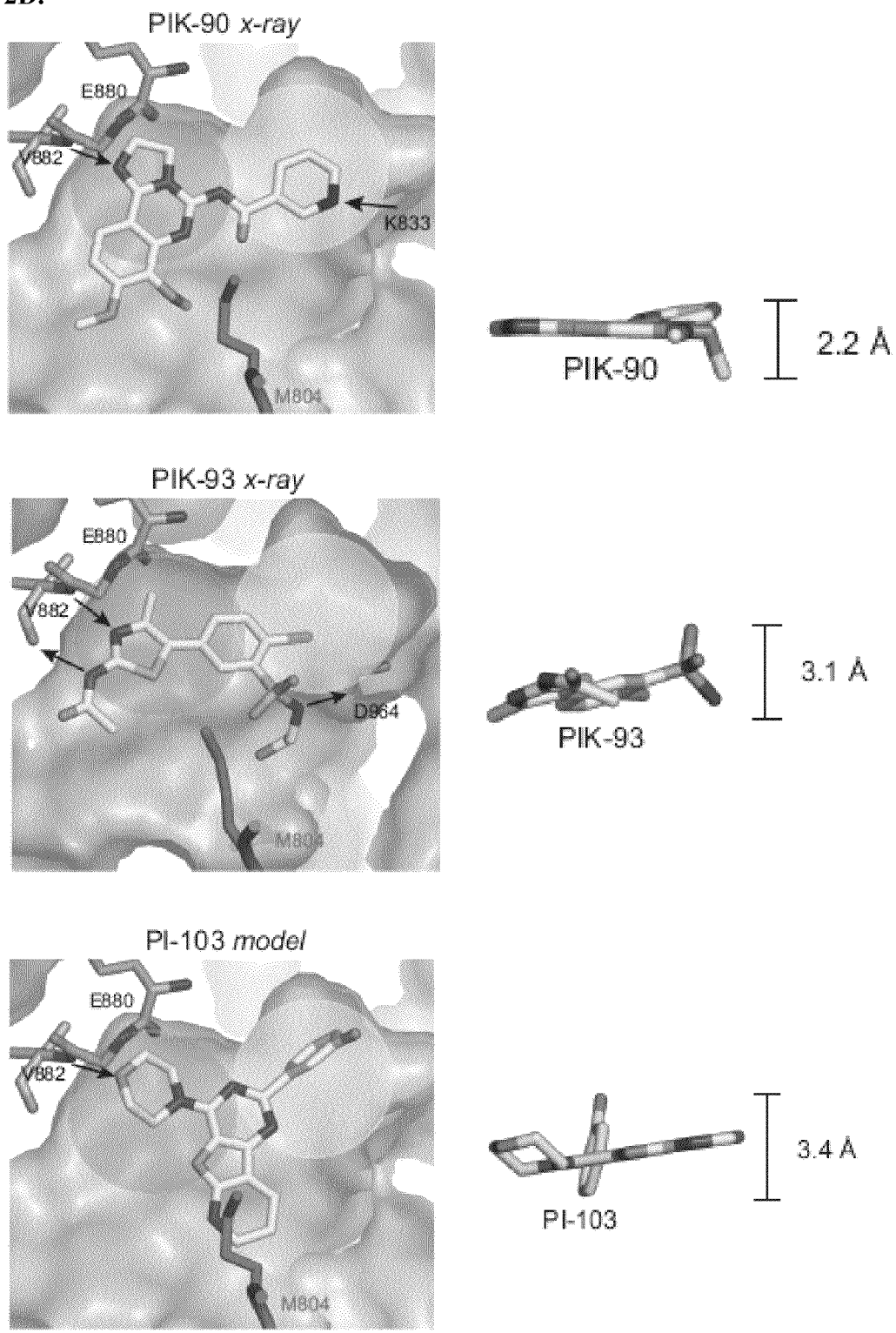

The term "PI3-Kinase affinity pocket," as used herein, refers to a cavity within p110α, p110β, p110γ, and p110δ corresponding to the lightly shaded region shown in FIGS. 2A, 2C, and 2D labeled "Affinity Pocket." FIGS. 2A, 2C, and 2D illustrate a computer model of the p110γ crystal structure. In p110γ, the surface of the PI3-Kinase affinity pocket is bound, at least in part, by the side chain of K833, D964, I879, and D841 (p110γ numbering, see FIG. 8). The surface of the corresponding cavity in p110δ is bound, at least in part, by the side chain of K779, D911, I825, and D787 (p110δ numbering, see FIG. 7). The corresponding cavity within p110α is bound, at least in part, by the side chains of K802, D933, I848, and D810 (p110α numbering, see FIG. 9). The corresponding cavity within p110β is bound, at least in part, by the side chains of K805, D937, I851, and D813 (p110β numbering, see FIG. 10). The PI3-Kinase affinity pocket is not accessed by ATP.

The PI3-Kinase affinity pocket of p110δ may be referred to herein as the p110δ affinity pocket. Likewise, the PI3-Kinase affinity pocket of p110γ may be referred to herein as the p110γ affinity pocket. The PI3-Kinase affinity pocket includes lysine 779, which, according to computer models, forms a hydrogen bond with the pyridine nitrogen of PIK-90 and the phenol oxygen of PI 103 (FIG. 2D), both of which are inhibitors of p110δ. Based on these computer modeling results, a novel antagonist was designed based on the chemical structure of PIK-39 and IC87114, as detailed below.

Figure 3A:
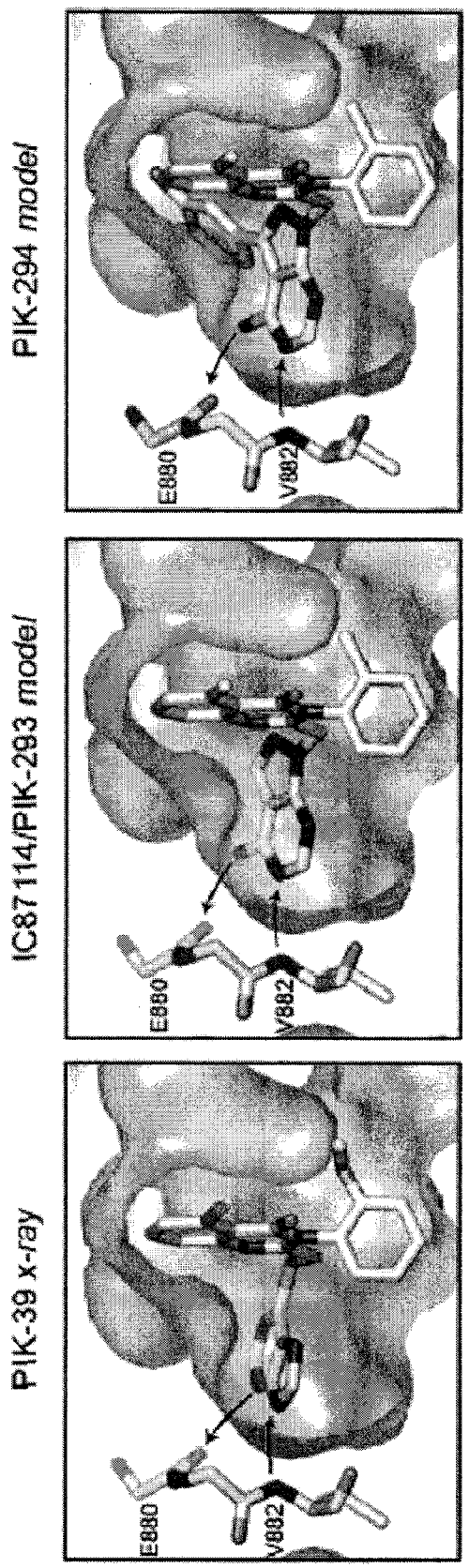
FIG. 3 illustrates the probing of selectivity and an the PI3-Kinase affinity pocket. A. The structure of PIK-39 bound to p110γ suggests a model for the binding of IC87114. PIK-293 and PIK-294 are pyrazolopyrimidine analogs of IC87114. PIK-294 projects a m-phenol into the affinity pocket, and this compound is more potent against the class I PI3-Ks. B. (Left) Ratio of IC50 values between mutant and wild-type for p110δ inhibitors and p110α/multi-targeted inhibitors. (Center) Dose response curves for binding of two p110δ inhibitors to wild-type, M7521, and M752V p110δ (Right) Models suggesting the impact of the M7521 and M752V mutations in p110δ on the binding of the different classes of inhibitors.
Figure 3A:
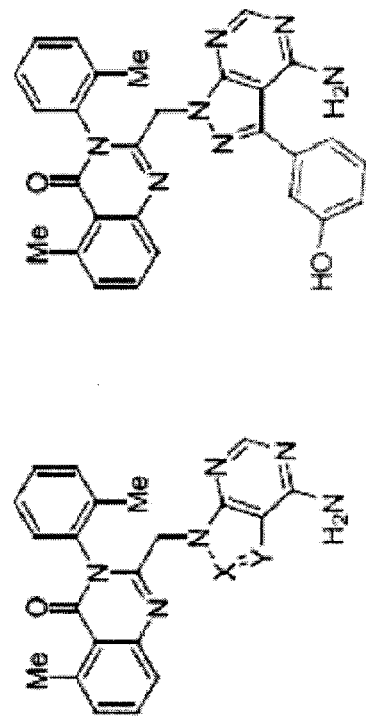

As shown in FIG. 2C, PIK-39 does not contain a PI3-Kinase binding pocket moiety. And as shown in FIG. 3A, IC87114 maintains contacts to E880 and V882 in the ATP binding region of p110δ, but is also missing a PI3-Kinase binding pocket moiety. By inserting m-phenol (a PI3-Kinase binding pocket moiety) at the C3 of the pyrazolopyrimidine of IC87114, the PI3-Kinase affinity pocket is accessed (FIG. 3A) resulting in a 60-fold increase in p110δ inhibition potency.

As described above, a PI3-Kinase binding pocket moiety is a substituent which, upon contacting upon contacting p110α, p110β, p110γ, or p110δ, fills space within the corresponding PI3-Kinase binding pocket. For example, a PI3-Kinase affinity pocket binding moiety is a substituent which, upon contacting upon contacting p110δ, fills space within the p110α affinity pocket. Likewise, a p110α affinity pocket binding moiety is a substituent which, upon contacting upon contacting p110α, fills space within the p110α affinity pocket.

In some embodiments, the PI3-Kinase binding pocket moiety additionally interacts (e.g. bonds) with an amino acid that forms part of the PI3-Kinase binding pocket. In some related embodiments, the interaction is a hydrogen bond, van der Waals interaction, ionic bond, covalent bond (e.g. disulfide bond) or hydrophobic interaction.

IV. Determining Space Filling Within the PI3-Kinase Affinity Pocket

To determine whether the PI3-Kinase affinity pocket binding moiety fills space within the PI3-Kinase affinity pocket, computer modeling techniques are employed. A query PI3-Kinase affinity pocket binding antagonist (i.e. a test compound) is fit into a computer image of p110γ. The p110γ computer image is derived from the solved co-crystal structure of human p110γ bound to PIK-39. The PyMOL Molecular Graphics System may be employed to generate the image. An example is presented in FIG. 3A, wherein IC87114 and PIK-294 are built into the computer image of p110γ kinase, derived from the p110γ-PIK-39 co-crystal. See Knight, et al., Cell 125: 733-745 (2006).

The computer models are typically analyzed to prevent any gross steric clashes and to satisfy key hydrogen bonds between the query PI3-Kinase affinity pocket binding antagonist and the p110γ protein (e.g. V882 and M804). In some embodiments, energy minimization calculations are performed to optimize binding energy. Using these techniques, one skilled in the art can easily determine whether a query PI3-Kinase affinity pocket binding antagonist includes a PI3-Kinase affinity pocket binding moiety that fills space within the PI3-Kinase affinity pocket.

In some embodiments, the query PI3-Kinase affinity pocket binding antagonist is analyzed to determine whether at least one bond (e.g. a hydrogen bond) is formed between the query PI3-Kinase affinity pocket binding antagonist and an amino acid that form part of the PI3-Kinase affinity pocket. Using a computer modeling technique as described above, the distance between one or more amino acids that form part of the PI3-Kinase affinity pocket and a potential contact point on the PI3-Kinase affinity pocket binding moiety is determined. Based on this distance, one skilled in the art may determine whether at least one bond is formed between one or more amino acids that form part of the PI3-Kinase affinity pocket and a PI3-Kinase affinity pocket binding moiety.

V. General Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Scheme I

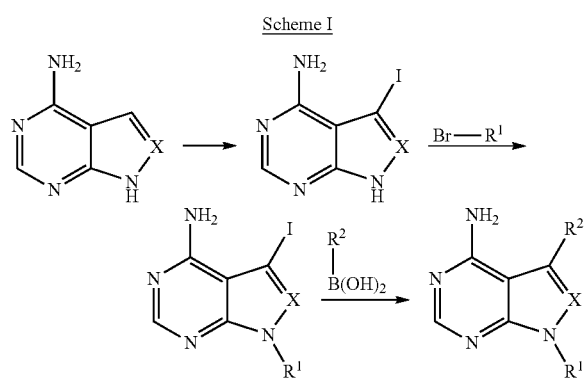

In Scheme I above, iodination of the pyrazolo- or pyrrolo-pyrimidine is accomplished using an appropriate iodination reagent, such as n-iodo-succinamide. Elaboration of the 1-position may be accomplished via halogen displacement of a brominated substituent (e.g. a substituted or unsubstituted alkylbromide). Palladium-catalyzed cross coupling between organoboronic acid and the iodo halide (i.e. Suzuki coupling), is then used to elaborate the 3-position. Recent catalyst and method developments have broadened the possible Suzuki coupling applications enormously, so that the scope of the reaction partners is not restricted to aryls. Potassium trifluoroborates and organoboranes or boronate esters may be used in place of boronic acids. Some pseudohalides (for example triflates) may also be used as coupling partners. Further information regarding Suzuki coupling may be found, for example in Kudo et al., *Angew. Chem. Int. Ed.* 45: 1282-1284 (2006); Kirchhoff et al., *J. Am. Chem. Soc.*, 124: 13662-13663 (2002); Wu et al., *J. Org. Chem.*, 68: 670-673 (2003); and Molander et al., *J. Org. Chem.*, 67:8424-8429 (2002).

VI. Methods

In another aspect, the present invention provides methods of decreasing the catalytic activity of a PI3 Kinase (e.g. a p110α kinase). The method includes the step of contacting the PI3 kinase with an activity decreasing amount of a compound of the present invention (i.e. a PI3-Kinase affinity pocket binding antagonist or the compound of Formula (I)). In some embodiments, the antagonist is capable of decreasing the catalytic activity of a tyrosine kinase. In some embodiments, the antagonist is a PI3-Kinase affinity pocket binding pyrazolopyrimidine antagonists, or PI3-Kinase affinity pocket binding pyrrolopyrimidine antagonists.

In some embodiments, the antagonist is specific to p110α relative to the antagonist action against p110δ, p110β, and/or p110γ. In some embodiments, the IC50 for p110α is at least 1.5, 2.0, 3.0, 4.0, 5.0, 10, 20, 30, 40, 50, 60, 70, 80, 90, 100, 200, 500, or 1000 fold lower than the IC50 against p110α, p110β, and/or p110γ. In other embodiments, the IC50 of the antagonist against the p110α is less than 100 μM, 50 μM, 40 μM, 30 μM, 20 μM, 10 μM, 5 μM, 1 μM, 0.5 μM, 0.1 μM, 50 nM, 10 nM, 1 nM. 0.5 nM, 0.1 nM, 50 pM, 10 pM, or 1 pM.

In some embodiments, the antagonist is specific to p110α relative to the antagonist action against insulin receptor tyrosine kinase. In some embodiments, the IC50 for p110α is at least 1.5, 2.0, 3.0, 4.0, 5.0, 10, 20, 30, 40, 50, 60, 70, 80, 90, 100, 200, 500, or 1000 fold lower than the IC50 against insulin receptor tyrosine kinase. In other embodiments, the IC50 of the antagonist against the p110α is less than 100 μM, 50 μM, 40 μM, 30 μM, 20 μM, 10 μM, 5 μM, 1 μM, 0.5 μM, 0.1 μM, 50 nM, 10 nM, 1 nM. 0.5 nM, 0.1 nM, 50 pM, 10 pM, or 1 pM.

In some embodiments, the antagonist decreases, or is capable of decreasing, the catalytic activity of a tyrosine kinase. In some embodiments, the IC50 of the antagonist against the tyrosine kinase is less than 100 μM, 50 μM, 40 μM, 30 μM, 20 μM, 10 μM, 5 μM, 1 μM, 0.5 μM, 0.1 μM, 50 nM, 10 nM, 1 nM. 0.5 nM, 0.1 nM, 50 pM, 10 pM, or 1 pM. Some tyrosine kinases include, for example, DNA-dependent protein kinase DNA-dependent protein kinase (pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23 820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3.

In some embodiments, the antagonist decreases, or is capable of decreasing, the catalytic activity of mTOR (PPAN AAI17167). In some embodiments, the IC50 of the antagonist against mTOR is less than 100 μM, 50 μM, 40 μM, 30 μM, 20 μM, 10 μM, 5 μM, 1 μM, 0.5 μM, 0.1 μM, 50 nM, 10 nM, 1 nM. 0.5 nM, 0.1 nM, 50 pM, 10 pM, or 1 pM.

In some embodiments, the antagonist decreases, or is capable of decreasing, the catalytic activity of mTOR and p110α at an IC50 of less than 100 μM, 50 μM, 40 μM, 30 μM, 20 μM, 10 μM, 5 μM, 1 μM, 0.5 μM, 0.1 μM, 50 nM, 10 nM, 1 nM. 0.5 nM, 0.1 nM, 50 pM, 10 pM, or 1 pM. In other embodiments, the antagonist decreases, or is capable of decreasing, the catalytic activity of a tyrosine kinase and p110α at an IC50 of less than 100 μM, 50 μM, 40 μM, 30 μM, 20 μM, 10 μM, 5 μM, 1 μM, 0.5 μM, 0.1 μM, 50 nM, 10 nM, 1 nM, 0.5 nM, 0.1 nM, 50 pM, 10 pM, or 1 pM. In other embodiments, the antagonist decreases, or is capable of decreasing, the catalytic activity of a tyrosine kinase, mTOR, and p110α at an IC50 of less than 100 μM, 50 μM, 40 μM, 30 μM, 20 μM, 10 μM, 5 μM, 1 μM, 0.5 μM, 0.1 μM, 50 nM, 10 nM, 1 nM. 0.5 nM, 0.1 nM, 50 pM, 10 pM, or 1 pM.

In another aspect, the present invention provides a method of treating a disease or condition mediated by PI3 kinase activity, PI3 Kinase activity and Tyrosine Kinase Activity, PI3 Kinase activity and mTOR Activity, or PI3 Kinase activity, mTOR activity, and Tyrosine Kinase Activity in a subject in need of such treatment. The method includes administering to the subject a therapeutically effective amount of an antagonist. The antagonist is a PI3-Kinase affinity pocket binding antagonist or the compound of Formula (I). In some embodiments the antagonist is a PI3-Kinase affinity pocket binding pyrazolopyrimidine antagonists, or PI3-Kinase affinity pocket binding pyrrolopyrimidine antagonists.

The disease may also be a bone-resorption disorder, chronic myelogenous leukemia, abnormal inflammation, autoimmune disease, thrombosis, or asthma. The disease may also be a type of cancer or cancer metastasis, including, for example, leukemia, carcinomas and sarcomas, such as cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer. In some embodiments, the disease is selected from disease is liver cancer, colon cancer, breast cancer, melanoma, acute myelogenous leukemia, chronic myelogenous leukemia, or non-small-cell lung cancer.

In another aspect, the present invention provides methods of disrupting the function of a leukocyte or disrupting a function of an osteoclast. The method includes contacting the leukocyte or the osteoclast with a function disrupting amount of the antagonist. The antagonist is a PI3-Kinase affinity pocket binding antagonist or the compound of Formula (I). In some embodiments the antagonist is a PI3-Kinase affinity pocket binding pyrazolopyrimidine antagonist, or PI3-Kinase affinity pocket binding pyrrolopyrimidine antagonist.

VII. Pharmaceutical Formulations

In another aspect, the present invention provides a pharmaceutical composition including an antagonist in admixture with a pharmaceutically acceptable excipient. One of skill in the art will recognize that the pharmaceutical compositions include the pharmaceutically acceptable salts of the PI3-Kinase antagonists of the present invention described above.

In therapeutic and/or diagnostic applications, the compounds of the invention can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g. patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the composition. Alternatively, these agents may be part of a single dosage form, mixed together with the inhibitor in a single composition.

The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. For example, the PI3-Kinase antagonists of the present invention described above are equally applicable to the methods of treatment and methods of inhibiting kinases described herein. References cited throughout this application are examples of the level of skill in the art and are hereby incorporated by reference herein in their entirety for all purposes, whether previously specifically incorporated or not.

VIII. Examples

The following examples are meant to illustrate certain embodiments of the invention, and not to limit the scope of the invention.

General Methods. All chemicals, reagents and solvents used were purchased commercially and used as received. dH2O refers to deioinized water. Evaporation of solvents was carried out on a rotary evaporator under reduced pressure. Compounds were purified by High Pressure Liquid Chromatography (HPLC) eluting with $dH_2O$-MeCN-trifluroacetic acid, 50:50:0.1, unless otherwise indicated. Analysis of products was carried out on a Liquid Chromatography Mass Spectrometer (LCMS) using MeCN-0.1% formic acid (varying ratios) as eluent.

A. Selected Reaction Procedures.

Synthesis of 1H-pyrazolo[3,4-d]pyrimidin-4-amine (BA18). A solution of 250 mL of formamide and 3-amino-4-pyrazolecarbonitrile (25 g, 0.231 mol) was heated to 180° C. overnight under an argon atmosphere. Reaction was cooled and 400 mL of $dH_2O$ were added. The resulting solid was filtered and rinsed with cold $dH_2O$. White solid precipitate was collected and dried in vacuo overnight to yield BA18 (39 g, 100% yield). ESI-MS $(M+H)^+$ m/z calcd 136.1, found 136.1.

Synthesis of 3-iodo-1H-pyrazolo[3,4-d]pyrimidin-4-amine (BA19). A solution of 3H-pyrazolo[3,4-d]pyrimidin-4-amine (10 g, 0.074 mol) and n-iodo-succinamide (25 g, 0.111 mol) in DMF (80 mL) was heated to 80° C. overnight under an argon atmosphere. The resulting solid was filtered and rinsed with cold EtOH. Product was dried in vacuo overnight to yield BA19 (24 g, 100% yield). ESI-MS $(M+H)^-$ m/z calcd 262.0, found 262.0

Synthesis of 3-iodo-1-isopropyl-1H-pyrazolo[3,4-d]pyrimidin-4-amine (BA12). A solution of 3-iodo-1H-pyrazolo[3,4-d]pyrimidin-4-amine (2 g, 0.0077 mol) and $K_2CO_3$ (4.2 g, 0.031 mol) in DMF (50 mL) was brought to 80° C. under an argon atmosphere. Isopropylbromide (1.0 g, 0.0084 mol) was added with a syringe. Reaction was refluxed under argon atmosphere for 2 hours. Solid $K_2CO_3$ was removed by filtration. Solvent was partially removed in vacuo. Sodium citrate (50 mL) was added and reaction was extracted with EtOAc. Organic phases concentrated in vacuo and purified using silica gel column chromatography [MeOH—$CH_2Cl_2$, 5:95] yielding BA12 (1.68 g, 72% yield). ESI-MS $(M+H)^+$ m/z calcd 304.0, found 304.1.

General Suzuki coupling. Preparation of final products (see Table 1 for final product names and structures).

3-iodo-1-isopropyl-1H-pyrazolo[3,4-d]pyrimidin-4-amine (40 mg, 0.13 mmol, 1 equivalent) was dissolved in DME (12 ml). Boronic acid (1.1 equivalent) was dissolved in EtOH (3.3 ml) and added to reaction mixture. Pd(PPh3)4 (30 mg, 0.026 mmol, 0.2 equivalents) and saturated Na2CO3 (1.9 ml) were added to the reaction mixture and heated to 80° C. under argon and refluxed for 8 hours. After cooling, the reaction was extracted with saturated NaCl and CH2Cl2. Organic phases were combined and solvent was removed. Resulting solid (or oil) was dissolved in dH2O-MeCN-trifluroacetic acid, 50:50:0.1 and purified by HPLC. Purified product (varying yields) was confirmed by LCMS.

Synthesis of 4-(4-Amino-1-isopropyl-1H-pyrazolo[3,4-d]pyrimidin-3-yl)-benzenesulfonamide (BA14). A solution of benzenesulfonamide-4-boronic acid pinacol ester (23 mg, 0.08 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA14 (2.2 mg, 10% yield). ESI-MS (M+H)$^+$ m/z calcd 333.1, found 333.1.

Synthesis of 1-isopropyl-3-(3-methoxy-4-methylphenyl)-1H-pyrazolo[3,4-d]pyrimidin-4-amine (BA15). A solution of 2 methoxy-4-(4,4,5,5-tetramethyl-1,3-2-dioxaborolan-2-yl)phenol (19 mg, 0.08 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA15 (4.3 mg, 20% yield). ESI-MS (M+H)$^+$ m/z calcd 300.1, found 300.2.

Synthesis of 6-(4-amino-1-isopropyl-1H-pyrazolo[3,4-d]pyrimidin-3-yl)naphthalen-2-ol (BA17). A solution of 6-hydroxynaphthalen-2-yl-2-boronic acid (15 mg, 0.08 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA15 (4.8 mg, 23% yield). ESI-MS (M+H)$^-$ m/z calcd 320.1, found 320.1.

Synthesis of tert-butyl 4-(4-amino-1-isopropyl-1H-pyrazolo[3,4-d]pyrimidin-3-yl)-2-methoxyphenylcarbamate (BA20). A solution of 4 4-N-Boc-amino-3-methoxy-benzeneboronic acid (48 mg, 0.18 mmol) in EtOH (3.3 mL) was added to a solution of 3-iodo-1-isopropyl-1H-pyrazolo[3,4-d]pyrimidin-4-amine (50 mg, 0.18 mmol) in DME (12 mL). Pd(PPh$_3$)$_4$ (40 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA20. ESI-MS (M+H)$^+$ m/z calcd 399.2, found 399.1.

Synthesis of 3-(4-amino-3-methoxyphenyl)-1-isopropyl-1H-pyrazolo[3,4-d]pyrimidin-4-amine (BA20d). A solution of tert-butyl 4-(4-amino-1-isopropyl-1H-pyrazolo[3,4-d]pyrimidin-3-yl)-2-methoxyphenylcarbamate (BA20) (20 mg, 0.05 mmol) in CH$_2$Cl$_2$, TFA, S(CH$_2$)$_2$, H$_2$O (45:45:5:5) (1 mL) was stirred at room temperature for 15 minutes. NaHCO$_3$ (2 mL) was added till reaction was alkaline. Reaction was extracted with H$_2$O and CH$_2$Cl$_2$. Organic phases were combined, concentrated in vacuo and purified by RP-HPLC (MeCN:H$_2$O:0.1% TFA) to yield BA20d.

Synthesis of 5-(4-amino-1-isopropyl-1H-pyrazolo[3,4-d]pyrimidin-3-yl)pyridine-2-carbonitrile (BA21). A solution of 2-cyanopyridine 5-boronic acid pinocol ester (18 mg, 0.08 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA21 (2.5 mg, 14% yield). ESI-MS (M+H)$^+$ m/z calcd 280.1, found 280.1.

Synthesis of 3-(3-(benzyloxy)-5-fluorophenyl)-1-isopropyl-1H-pyrazolo[3,4-d]pyrimidin-4-amine. A solution of (3-Benzyloxy-5-fluorophenyl)boronic acid (29 mg, 5.80 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA22 (15.6 mg, 60% yield). ESI-MS (M+H)$^+$ m/z calcd 378.1, found 378.0.

Synthesis of 3-(4-amino-1-isopropyl-1H-pyrazolo[3,4-d]pyrimidin-3-yl)-5-fluorophenol (BA22). A solution of -(3-(benzyloxy)-5-fluorophenyl)-1-isopropyl-1H-pyrazolo[3,4-d]pyrimidin-4-amine (15 mg, 0.04 mmol) in MeOH (0.9 mL) was flushed with argon. Pd on activated carbon (10 mL) was carefully added while keeping reaction under an argon atmosphere. Reaction was flushed with H$_2$ gas and left under H$_2$ atmosphere overnight at room temperature. The reaction was filtered through celite and rinsed with MeOH to yield BA22 (15 mg, 100% yield). ESI-MS (M+H)$^+$ m/z calcd 288.1, found 288.1.

Synthesis of 1-isopropyl-3-(3,4-dimethoxyphenyl)-1H-pyrazolo[3,4-d]pyrimidin-4-amine (BA23). A solution of 3,4-Dimethoxyphenylboronic acid (24 mg, 0.13 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA23 (13.1 mg, 60% yield). ESI-MS (M+H)$^+$ m/z calcd 314.0, found 314.1.

Synthesis of (3-(4-amino-1-isopropyl-1H-pyrazolo[3,4-d]pyrimidin-3-yl)phenyl)methanol (BA26). A solution of (3-Hydroxymethylphenyl)boronic acid (24 mg, 0.13 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA26 (8.4 mg, 42% yield). ESI-MS (M+H)$^+$ m/z calcd 283.1, found 284.2.

Synthesis of 3-(4-amino-1-isopropyl-1H-pyrazolo[3,4-d]pyrimidin-3-yl)-N-(4,5-dihydrothiazol-2-yl)benzamide (BA30). A solution of [3-((4,5-dihydrothiazol-2-yl)carbamoyl)phenyl]boronic acid (19 mg, 0.08 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA30 (17.8 mg, 67% yield).

Synthesis of 1-(4-(4-amino-1-isopropyl-1H-pyrazolo[3,4-d]pyrimidin-3-yl)phenyl)ethanone (BA31). A solution of 4-Acetylphenylboronic acid (12.7 mg, 0.08 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA31 (12.9 mg, 62% yield).

Synthesis of (3-(4-amino-1-isopropyl-1H-pyrazolo[3,4-d]pyrimidin-3-yl)phenyl)methanol (BA32). A solution of (4-Aminocarbonyl-3-chlorophenyl)boronic acid (16 mg, 0.08 mmol) in EtOH (3.3 mL) was added to a solution of 3-iodo-1-isopropyl-1H-pyrazolo[3,4-d]pyrimidin-4-amine (20 mg, 0.07 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA32 (9.7 mg, 42% yield). ESI-MS (M+H)$^+$ m/z calcd 331.1, found 331.1.

Synthesis of 5-(4-amino-1-isopropyl-1H-pyrazolo[3,4-d]pyrimidin-3-yl)-3-methylthiophene-2-carbaldehyde (BA34). A solution of 5-Formyl-3-methylthiophene-2-boronic acid (26 mg, 0.14 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA34 (14.7 mg, 38% yield). ESI-MS (M+H)$^+$ m/z calcd 302.1, found 302.0.

Synthesis of 5-(4-amino-1-isopropyl-1H-pyrazolo[3,4-d]pyrimidin-3-yl)furan-3-carbaldehyde (BA35). A solution of 4-Formylfuran-2-boronic acid (20 mg, 0.14 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA35 (13.5 mg, 39% yield). ESI-MS (M+H)$^+$ m/z calcd 272.1, found 272.1.

Synthesis of N-[3-(4-Amino-1-isopropyl-1H-pyrazolo[3,4-d]pyrimidin-3-yl)-phenyl]-methanesulfonamide (BA38). A solution of 3-Methanesulfonylaminophenylboronic acid (32 mg, 0.15 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (16 mg, 0.014 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA38 (24.3 mg, 54% yield). ESI-MS (M+H)$^+$ m/z calcd 347.1, found 347.0.

Synthesis of 3-(4-amino-1-isopropyl-1H-pyrazolo[3,4-d]pyrimidin-3-yl)benzonitrile (BA39). A solution of 3-Cyanophenylboronic acid (23 mg, 0.15 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA39 (14.9 mg, 41% yield). ESI-MS (M+H)$^+$ m/z calcd 279.1, found 279.0.

Synthesis of N-[4-(4-Amino-1-isopropyl-1H-pyrazolo[3,4-d]pyrimidin-3-yl)-phenyl]methanesulfonamide (BA40). A solution of 4-methanesulfonylaminophenylboronic acid (24 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA40 (0.9 mg, 3% yield). ESI-MS (M+H)$^+$ m/z calcd 347.1, found 347.0.

Synthesis of 3-(4-Amino-1-isopropyl-1H-pyrazolo[3,4-d]pyrimidin-3-yl)benzenesulfonamide (BA41). A solution of benzenesulfonamide-3-boronic acid pinacol ester (31 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA41 (9.2 mg, 28% yield). ESI-MS (M+H)$^+$ m/z calcd 333.1, found 333.0.

Synthesis of 2-(4-amino-1-isopropyl-1H-pyrazolo[3,4-d]pyrimidin-3-yl)benzo[b]thiophene-5-carbaldehyde (BA42). A solution of 5-Formylbenzo[b]thiophene-2-boronic acid pinacol ester (31 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA42 (15.2 mg, 45% yield). ESI-MS (M+H)$^+$ m/z calcd 338.1, found 338.0.

Synthesis of 5-(4-amino-1-isopropyl-1H-pyrazolo[3,4-d]pyrimidin-3-yl)-1H-indole-3-carbaldehyde (BA43). A solution of N-Boc-3-formyl-5-indoleboronic acid pinacol ester (40 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA). The TFA from purification hydrolyzed the Boc to yield BA43. ESI-MS (M+H)$^+$ m/z calcd 321.1, found 321.0.

Synthesis of 3-(benzo[c][1,2,5]oxadiazol-6-yl)-1-isopropyl-1H-pyrazolo[3,4-d]pyrimidin-4-amine (BA44). A solution of Benzo[c][1,2,5]oxadiazole-5-boronic acid (18 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA44. ESI-MS (M+H)$^+$ m/z calcd 296.1, found 296.1.

Synthesis of 2-(4-(4-amino-1-isopropyl-1H-pyrazolo[3,4-d]pyrimidin-3-yl)phenyl)acetonitrile (BA45). A solution of (4-Cyanomethylphenyl)boronic acid (18 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA45. ESI-MS (M+H)$^+$ m/z calcd 293.1, found 293.1.

Synthesis of 2-(3-(4-amino-1-isopropyl-1H-pyrazolo[3,4-d]pyrimidin-3-yl)phenyl)acetonitrile (BA46). A solution of (3-Cyanomethylphenyl)boronic acid (18 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA45. ESI-MS (M+H)$^+$ m/z calcd 293.1, found 293.1.

Synthesis of 1-isopropyl-3-(4-methoxyphenyl)-1H-pyrazolo[3,4-d]pyrimidin-4-amine (BA48). A solution of (4-methoxyphenylboronic acid (17 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA48 (4.5 mg, 16% yield). ESI-MS (M+H)$^+$ m/z calcd 284.1, found 284.1.

Synthesis of 1-isopropyl-3-(3-methoxyphenyl)-1H-pyrazolo[3,4-d]pyrimidin-4-amine (BA49). A solution of 3-Methoxyphenylboronic acid (17 mg, 0.11 mmol) in EtOH (3.3 mL) was added to a solution of 3-iodo-1-isopropyl-1H-pyrazolo[3,4-d]pyrimidin-4-amine (30 mg, 0.10 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA49. ESI-MS (M+H)$^+$ m/z calcd 284.1, found 284.0.

Synthesis of 1-isopropyl-3-(pyridin-3-yl)-1H-pyrazolo[3,4-d]pyrimidin-4-amine (BA52). A solution of 3-Pyridinylboronic acid (15 mg, 0.14 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (15 mg, 0.015 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O) to yield BA52. ESI-MS (M+H)$^+$ m/z calcd 255.1, found 255.0.

Synthesis of 1-isopropyl-3-(pyrimidin-5-yl)-1H-pyrazolo[3,4-d]pyrimidin-4-amine (BA53). A solution of 5-Pyrimidinylboronic acid (15 mg, 0.14 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (15 mg, 0.015 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O) to yield BA53. ESI-MS (M+H)$^+$ m/z calcd 256.1, found 256.1.

Synthesis of 3-(2,3-dihydrobenzo[b][1,4]dioxin-6-yl)-1-isopropyl-1H-pyrazolo[3,4-d]pyrimidin-4-amine (BA54). A solution of 2,3-dihydro-1,4-benzodioxin-6-ylboronic acid (26 mg, 0.14 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA54 (6 mg, 15% yield). ESI-MS (M+H)$^+$ m/z calcd 312.1, found 312.0.

Synthesis of 1-(3-(4-amino-1-isopropyl-1H-pyrazolo[3,4-d]pyrimidin-3-yl)phenyl)ethanone (BA55). A solution of 3-Acetylphenylboronic acid (23 mg, 0.14 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA55 (7 mg, 18% yield). ESI-MS (M+H)$^+$ m/z calcd 296.1, found 296.1.

Synthesis of 4-(4-amino-1-isopropyl-1H-pyrazolo[3,4-d]pyrimidin-3-yl)phenol (BA56). A solution of 4-Hydroxyphenylboronic acid (30 mg, 0.14 mmol) in EtOH (3.3 mL) was added to a solution of 3-iodo-1-isopropyl-1H-pyrazolo[3,4-d]pyrimidin-4-amine (40 mg, 0.13 mmol) in DME (12 mL). Pd(PPh$_3$)$_4$ (30 mg, 0.03 mmol) and saturated Na$_2$CO$_3$ (1.9 mL) were added and the reaction was heated to 80° C. under an argon atmosphere overnight. After cooling, the reaction was extracted with saturated NaCl and CH$_2$Cl$_2$. Organic phases were combined, concentrated in vacuo and purified by RP-HPLC (MeCN:H$_2$O:0.1% TFA) to yield BA56 (12 mg, 32% yield). ESI-MS (M+H)$^+$ m/z calcd 270.1, found 270.1.

Synthesis of PI3-K/Tyrosine Kinase Dual Inhibitors

Synthesis of 1H-pyrazolo[3,4-d]pyrimidin-4-amine (BA18). A solution of 250 ml of formamide and 3-amino-4-pyrazolecarbonitrile (25 g, 0.231 mol) was heated to 180° C. overnight under an argon atmosphere. Reaction was cooled and 400 ml of dH2O were added. The resulting solid was filtered and rinsed with cold dH2O. White solid precipitate was collected and dried in vacuo overnight to yield BA18 (39 g, 100% yield). ESI-MS (M+H)+ m/z calcd 136.1, found 136.1.

Synthesis of 3-iodo-1H-pyrazolo[3,4-d]pyrimidin-4-amine (BA19). A solution of 3H-pyrazolo[3,4-d]pyrimidin-4-amine (10 g, 0.074 mol) and n-iodo-succinamide (25 g, 0.111 mol) in DMF (80 ml) was heated to 80° C. overnight under an argon atmosphere. The resulting solid was filtered and rinsed with cold EtOH. Product was dried in vacuo overnight to yield BA19 (24 g, 100% yield). ESI-MS (M+H)+ m/z calcd 262.0, found 262.0

Synthesis of 3-iodo-1-isopropyl-1H-pyrazolo[3,4-d]pyrimidin-4-amine (BA12). A solution of 3-iodo-1H-pyrazolo[3,4-d]pyrimidin-4-amine (2 g, 0.0077 mol) and K2CO3 (4.2 g, 0.031 mol) in DMF (50 ml) was brought to 80° C. under an argon atomosphere. Isopropylbromide (1.0 g, 0.0084 mol) was added with a syringe. Reaction was refluxed under argon atmosphere for 2 hours. Solid K2CO3 was removed by filtration. Solvent was partially removed in vacuo. Sodium citrate (50 ml) was added and reaction was extracted with EtOAc. Organic phases concentrated in vacuo and purified using silica gel column chromatography [MeOH—$CH_2Cl_2$, 5:95] yielding BA12 (1.68 g, 72% yield). ESI-MS (M+H)+ m/z calcd 304.0, found 304.1.

Synthesis of 4-(4-Amino-1-isopropyl-1H-pyrazolo[3,4-d]pyrimidin-3-yl)benzenesulfonamide (BA14). A solution of benzenesulfonamide-4-boronic acid pinacol ester (23 mg, 0.08 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA14 (2.2 mg, 10% yield). ESI-MS (M+H)+ m/z calcd 333.1, found 333.1.

Synthesis of 1-isopropyl-3-(3-methoxy-4-methylphenyl)-1H-pyrazolo[3,4-d]pyrimidin-4-amine (BA15). A solution of 2 methoxy-4-(4,4,5,5-tetramethyl-1,3-2-dioxaborolan-2-yl) phenol (19 mg, 0.08 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA15 (4.3 mg, 20% yield). ESI-MS (M+H)+ m/z calcd 300.1, found 300.2.

Synthesis of 6-(4-amino-1-isopropyl-1H-pyrazolo[3,4-d]pyrimidin-3-yl)naphthalen-2-ol (BA17). A solution of 6-hydroxynaphthalen-2-yl-2-boronic acid (15 mg, 0.08 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA15 (4.8 mg, 23% yield). ESI-MS (M+H)+ m/z calcd 320.1, found 320.1.

Synthesis of tert-butyl 4-(4-amino-1-isopropyl-1H-pyrazolo[3,4-d]pyrimidin-3-yl)-2-methoxyphenylcarbamate (BA20). A solution of 4 4-N-Boc-amino-3-methoxy-benzeneboronic acid (48 mg, 0.18 mmol) in EtOH (3.3 ml) was added to a solution of 3-iodo-1-isopropyl-1H-pyrazolo[3,4-d]pyrimidin-4-amine (50 mg, 0.18 mmol) in DME (12 ml). Pd(PPh3)4 (40 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA20. ESI-MS (M+H)+ m/z calcd 399.2, found 399.1.

Synthesis of 3-(4-amino-3-methoxyphenyl)-1-isopropyl-1H-pyrazolo[3,4-d]pyrimidin-4-amine (BA20d). A solution of tert-butyl 4-(4-amino-1-isopropyl-1H-pyrazolo[3,4-d]pyrimidin-3-yl)-2-methoxyphenylcarbamate (BA20) (20 mg, 0.05 mmol) in CH2Cl2, TFA, S(CH2)2, H2O (45:45:5:5) (1 ml) was stirred at room temperature for 15 minutes. NaHCO3 (2 ml) was added till reaction was alkaline. Reaction was extracted with $H_2O$ and $CH_2Cl_2$. Organic phases were combined, concentrated in vacuo and purified by RP-HPLC (MeCN:H2O:0.1% TFA) to yield BA20d.

Synthesis of 2-amino-5-(4-amino-1-isopropyl-1H-pyrazolo[3,4-d]pyrimidin-3-yl)phenol (BA20dd). BA20 (tert-butyl 4-(4-amino-1-isopropyl-1H-pyrazolo[3,4-d]pyrimidin-3-yl)-2-methoxyphenylcarbamate, 7 mg, 0.018 mmol) was dissolved in CH2Cl2 (2.5 ml) and stirred under an argon atmosphere at room temperature. BBr3 (0.500 ml) was added slowly with a syringe. The reaction mixture was stirred overnight, under argon at room temperature. BBr3 was removed in vacuo and the remaining solid was purified by RP-HPLC (MeCN:H2O:0.1% TFA) to yield BA20dd.

Synthesis of 5-(4-amino-1-isopropyl-1H-pyrazolo[3,4-d]pyrimidin-3-yl)pyridine-2-carbonitrile (BA21). A solution of 2-cyanopyridine 5-boronic acid pinocol ester (18 mg, 0.08 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA21 (2.5 mg, 14% yield). ESI-MS (M+H)+ m/z calcd 280.1, found 280.1.

Synthesis of 3-(3-(benzyloxy)-5-fluorophenyl)-1-isopropyl-1H-pyrazolo[3,4-d]pyrimidin-4-amine. A solution of (3-Benzyloxy-5-fluorophenyl)boronic acid (29 mg, 5.80 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA22 (15.6 mg, 60% yield). ESI-MS (M+H)+ m/z calcd 378.1, found 378.0.

Synthesis of 3-(4-amino-1-isopropyl-1H-pyrazolo[3,4-d]pyrimidin-3-yl)-5-fluorophenol (BA22). A solution of -(3-(benzyloxy)-5-fluorophenyl)-1-isopropyl-1H-pyrazolo[3,4-d]pyrimidin-4-amine (15 mg, 0.04 mmol) in MeOH (0.9 ml) was flushed with argon. Pd on activated carbon (10 ml) was carefully added while keeping reaction under an argon atmosphere. Reaction was flushed with H2 gas and left under H2 atmosphere overnight at room temperature. The reaction was filtered through celite and rinsed with MeOH to yield BA22 (15 mg, 100% yield). ESI-MS (M+H)+ m/z calcd 288.1, found 288.1.

Synthesis of 1-isopropyl-3-(3,4-dimethoxyphenyl)-1H-pyrazolo[3,4-d]pyrimidin-4-amine (BA23). A solution of 3,4-Dimethoxyphenylboronic acid (24 mg, 0.13 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA23 (13.1 mg, 60% yield). ESI-MS (M+H)+ m/z calcd 314.0, found 314.1.

Synthesis of tert-butyl 2-(4-amino-1-isopropyl-1H-pyrazolo[3,4-d]pyrimidin-3-yl)-5-(benzyloxy)-1H-indole-1-carboxylate (BA24). A solution of 5-Benzyloxy-1-BOC-indole-2-boronic acid (303 mg, 0.83 mmol) in EtOH (3.3 ml) was added to a solution of 3-iodo-1-isopropyl-1H-pyrazolo[3,4-d]pyrimidin-4-amine (100 mg, 0.33 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by silica gel column chromatography [EtOAc-hexanes, 5:95] to yield BA24. ESI-MS (M+H)+ m/z calcd 499.2, found 499.2.

Synthesis of 2-(4-amino-1-isopropyl-1H-pyrazolo[3,4-d]pyrimidin-3-yl)-1H-indol-5-ol (BA24dd). BA24 (3-(4-fluoro-3-methoxyphenyl)-1-isopropyl-1H-pyrazolo[3,4-d]pyrimidin-4-amine, 30 mg, 0.10 mmol) was dissolved in a solution of formic acid (4.5 ml, 10 equivalents) and HCl (0.45 ml, 1 equivalent). The reaction was heated and stirred for one hour under an argon atmosphere. The reaction was then concentrated in vacuo and purified by RP-HPLC (MeCN:H2O:0.1% TFA) to yield BA24dd. ESI-MS (M+H)+ m/z calcd 309.1, found 309.1.

Synthesis of (3-(4-amino-1-isopropyl-1H-pyrazolo[3,4-d]pyrimidin-3-yl)phenyl)methanol (BA26). A solution of (3-Hydroxymethylphenyl)boronic acid (24 mg, 0.13 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA26 (8.4 mg, 42% yield). ESI-MS (M+H)+ m/z calcd 283.1, found 284.2.

Synthesis of 3-(4-amino-1-isopropyl-1H-pyrazolo[3,4-d]pyrimidin-3-yl)-N-(4,5-dihydrothiazol-2-yl)benzamide (BA30). A solution of [3-((4,5-dihydrothiazol-2-yl)carbamoyl)phenyl]boronic acid (19 mg, 0.08 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA30 (17.8 mg, 67% yield).

Synthesis of 1-(4-(4-amino-1-isopropyl-1H-pyrazolo[3,4-d]pyrimidin-3-yl)phenyl)ethanone (BA31). A solution of 4-Acetylphenylboronic acid (12.7 mg, 0.08 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na$_2$CO$_3$ (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA31 (12.9 mg, 62% yield).

Synthesis of (3-(4-amino-1-isopropyl-1H-pyrazolo[3,4-d]pyrimidin-3-yl)phenyl)methanol (BA32). A solution of (4-Aminocarbonyl-3-chlorophenyl)boronic acid (16 mg, 0.08 mmol) in EtOH (3.3 ml) was added to a solution of 3-iodo-1-isopropyl-1H-pyrazolo[3,4-d]pyrimidin-4-amine (20 mg, 0.07 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA32 (9.7 mg, 42% yield). ESI-MS (M+H)+ m/z calcd 331.1, found 331.1.

Synthesis of 5-(4-amino-1-isopropyl-1H-pyrazolo[3,4-d]pyrimidin-3-yl)-3-methylthiophene-2-carbaldehyde (BA34). A solution of 5-Formyl-3-methylthiophene-2-boronic acid (26 mg, 0.14 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA34 (14.7 mg, 38% yield). ESI-MS (M+H)+ m/z calcd 302.1, found 302.0.

Synthesis of 5-(4-amino-1-isopropyl-1H-pyrazolo[3,4-d]pyrimidin-3-yl)furan-3-carbaldehyde (BA35). A solution of 4-Formylfuran-2-boronic acid (20 mg, 0.14 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA35 (13.5 mg, 39% yield). ESI-MS (M+H)+ m/z calcd 272.1, found 272.1.

Synthesis of N-[3-(4-Amino-1-isopropyl-1H-pyrazolo[3,4-d]pyrimidin-3-yl)-phenyl]methanesulfonamide (BA38). A solution of 3-Methanesulfonylaminophenylboronic acid (32 mg, 0.15 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (16 mg, 0.014 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA38 (24.3 mg, 54% yield). ESI-MS (M+H)+ m/z calcd 347.1, found 347.0.

Synthesis of 3-(4-amino-1-isopropyl-1H-pyrazolo[3,4-d]pyrimidin-3-yl)benzonitrile (BA39). A solution of 3-Cyanophenylboronic acid (23 mg, 0.15 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA39 (14.9 mg, 41% yield). ESI-MS (M+H)+ m/z calcd 279.1, found 279.0.

Synthesis of N-[4-(4-Amino-1-isopropyl-1H-pyrazolo[3,4-d]pyrimidin-3-yl)-phenyl]methanesulfonamide (BA40). A solution of 4-Methanesulfonylaminophenylboronic acid (24 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA40 (0.9 mg, 3% yield). ESI-MS (M+H)+ m/z calcd 347.1, found 347.0.

Synthesis of 3-(4-Amino-1-isopropyl-1H-pyrazolo[3,4-d]pyrimidin-3-yl)benzenesulfonamide (BA41). A solution of Benzenesulfonamide-3-boronic acid pinacol ester (31 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA41 (9.2 mg, 28% yield). ESI-MS (M+H)+ m/z calcd 333.1, found 333.0.

Synthesis of 2-(4-amino-1-isopropyl-1H-pyrazolo[3,4-d]pyrimidin-3-yl)benzo[b]thiophene-5-carbaldehyde (BA42). A solution of 5-Formylbenzo[b]thiophene-2-boronic acid pinacol ester (31 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA42 (15.2 mg, 45% yield). ESI-MS (M+H)+ m/z calcd 338.1, found 338.0.

Synthesis of 5-(4-amino-1-isopropyl-1H-pyrazolo[3,4-d]pyrimidin-3-yl)-1H-indole-3-carbaldehyde (BA43). A solution of N-Boc-3-formyl-5-indoleboronic acid pinacol ester (40 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA). The TFA from purification hydrolyzed the Boc to yield BA43. ESI-MS (M+H)+ m/z calcd 321.1, found 321.0.

Synthesis of 3-(benzo[c][1,2,5]oxadiazol-6-yl)-1-isopropyl-1H-pyrazolo[3,4-d]pyrimidin-4-amine (BA44). A solution of Benzo[c][1,2,5]oxadiazole-5-boronic acid (18 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA44. ESI-MS (M+H)+ m/z calcd 296.1, found 296.1.

Synthesis of 2-(4-(4-amino-1-isopropyl-1H-pyrazolo[3,4-d]pyrimidin-3-yl)phenyl)acetonitrile (BA45). A solution of (4-Cyanomethylphenyl)boronic acid (18 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA45. ESI-MS (M+H)+ m/z calcd 293.1, found 293.1.

Synthesis of 2-(3-(4-amino-1-isopropyl-1H-pyrazolo[3,4-d]pyrimidin-3-yl)phenyl)acetonitrile (BA46). A solution of (3-Cyanomethylphenyl)boronic acid (18 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA45. ESI-MS (M+H)+ m/z calcd 293.1, found 293.1.

Synthesis of 1-isopropyl-3-(4-methoxyphenyl)-1H-pyrazolo[3,4-d]pyrimidin-4-amine (BA48). A solution of (4-Methoxyphenylboronic acid (17 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA48 (4.5 mg, 16% yield). ESI-MS (M+H)+ m/z calcd 284.1, found 284.1.

Synthesis of 1-isopropyl-3-(3-methoxyphenyl)-1H-pyrazolo[3,4-d]pyrimidin-4-amine (BA49). A solution of 3-Methoxyphenylboronic acid (17 mg, 0.11 mmol) in EtOH (3.3 ml) was added to a solution of 3-iodo-1-isopropyl-1H-pyrazolo[3,4-d]pyrimidin-4-amine (30 mg, 0.10 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA49. ESI-MS (M+H)+ m/z calcd 284.1, found 284.0.

Synthesis of 1-isopropyl-3-(pyridin-3-yl)-1H-pyrazolo[3,4-d]pyrimidin-4-amine (BA52). A solution of 3-Pyridinylboronic acid (15 mg, 0.14 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (15 mg, 0.015 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O) to yield BA52. ESI-MS (M+H)+ m/z calcd 255.1, found 255.0.

Synthesis of 1-isopropyl-3-(pyrimidin-5-yl)-1H-pyrazolo[3,4-d]pyrimidin-4-amine (BA53). A solution of 5-Pyrimidinylboronic acid (15 mg, 0.14 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (15 mg, 0.015 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O) to yield BA53. ESI-MS (M+H)+ m/z calcd 256.1, found 256.1.

Synthesis of 3-(2,3-dihydrobenzo[b][1,4]dioxin-6-yl)-1-isopropyl-1H-pyrazolo[3,4-d]pyrimidin-4-amine (BA54). A solution of 2,3-dihydro-1,4-benzodioxin-6-ylboronic acid (26 mg, 0.14 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA54 (6 mg, 15% yield). ESI-MS (M+H)+ m/z calcd 312.1, found 312.0.

Synthesis of 1-(3-(4-amino-1-isopropyl-1H-pyrazolo[3,4-d]pyrimidin-3-yl)phenyl)ethanone (BA55). A solution of 3-Acetylphenylboronic acid (23 mg, 0.14 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA55 (7 mg, 18% yield). ESI-MS (M+H)+ m/z calcd 296.1, found 296.1.

Synthesis of 4-(4-amino-1-isopropyl-1H-pyrazolo[3,4-d]pyrimidin-3-yl)phenol (BA56). A solution of 4-Hydroxyphenylboronic acid (30 mg, 0.14 mmol) in EtOH (3.3 ml) was added to a solution of 3-iodo-1-isopropyl-1H-pyrazolo[3,4-d]pyrimidin-4-amine (40 mg, 0.13 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA56 (12 mg, 32% yield). ESI-MS (M+H)+ m/z calcd 270.1, found 270.1.

Synthesis of 4-(4-amino-1-isopropyl-1H-pyrazolo[3,4-d]pyrimidin-3-yl)-2-fluorophenol (BA59). A solution of 3-fluoro-4-hydroxyphenylboronic acid (103 mg, 0.66 mmol) in EtOH (3.3 ml) was added to a solution of 3-iodo-1-isopropyl-1H-pyrazolo[3,4-d]pyrimidin-4-amine (100 mg, 0.33 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP using silica gel column chromatography [MeOH—CH2Cl2, 2:98] to yield BA59 (26 mg, 27% yield). ESI-MS (M+H)+ m/z calcd 288, found 288.

Synthesis of 4-(4-amino-1-isopropyl-1H-pyrazolo[3,4-d]pyrimidin-3-yl)-3-methylphenol (BA60). A solution of 4-hydroxy-2-methylphenylboronic acid (110 mg, 0.66 mmol) in EtOH (3.3 ml) was added to a solution of 3-iodo-1-isopropyl-1H-pyrazolo[3,4-d]pyrimidin-4-amine (100 mg, 0.33 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by silica gel column chromatography [MeOH—CH2Cl2, 2:98] to yield BA60 (42 mg, 22% yield). ESI-MS (M+H)+ m/z calcd 284, found 284.

Synthesis of 3-(4-fluoro-3-methoxyphenyl)-1-isopropyl-1H-pyrazolo[3,4-d]pyrimidin-4-amine (BA62). A solution of 4-fluoro-3-methoxyphenylboronic acid (61 mg, 0.36 mmol) in EtOH (3.3 ml) was added to a solution of 3-iodo-1-isopropyl-1H-pyrazolo[3,4-d]pyrimidin-4-amine (90 mg, 0.30 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by silica gel column chromatography [MeOH—CH2Cl2, 2:98] to yield BA62 (40 mg, 44% yield). ESI-MS (M+H)+ m/z calcd 302, found 302.

Synthesis of 5-(4-amino-1-isopropyl-1H-pyrazolo[3,4-d]pyrimidin-3-yl)-2-fluorophenol (BA62d). A solution of BA62 (3-(4-fluoro-3-methoxyphenyl)-1-isopropyl-1H-pyrazolo[3,4-d]pyrimidin-4-amine, 30 mg, 0.10 mmol) was dissolved in CH2Cl2 (5 ml) and stirred under an argon atmosphere. BBr3 (500 uL, 0.5 mol) was added slowly with a syringe, while stirring. The reaction was stirred at room temperature for 3 hours then concentrated in vacuo and purified using silica gel column chromatography [MeOH—CH2Cl2, 2:98] to yield BA62d (23 mg, 44% yield). ESI-MS (M+H)+ m/z calcd 288.1, found 288.1.

Synthesis of 3-(2,5-difluoro-4-methoxyphenyl)-1-isopropyl-1H-pyrazolo[3,4-d]pyrimidin-4-amine (BA63). A solution of 2,5-difluoro-4-methoxyphenylboronic acid (84 mg, 0.45 mmol) in EtOH (3.3 ml) was added to a solution of 3-iodo-1-isopropyl-1H-pyrazolo[3,4-d]pyrimidin-4-amine (54 mg, 0.18 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by silica gel column chromatography [MeOH—CH2Cl2, 2:98] to yield BA63 (50 mg, 17% yield). ESI-MS (M+H)+ m/z calcd 320.1, found 320.0.

Synthesis of 4-(4-amino-1-isopropyl-1H-pyrazolo[3,4-d]pyrimidin-3-yl)-2,5-difluorophenol (BA93). 3-(2,5-difluoro-4-methoxyphenyl)-1-isopropyl-1H-pyrazolo[3,4-d]pyrimidin-4-amine (BA63) (20 mg, 0.06 mmol) was dissolved in CH2Cl2 (2 ml) and BBr3 (0.630 mL, 0.63 mmol) was added slowly with a syringe, while stirring. The reaction was stirred at room temperature for overnight then concentrated in vacuo and purified using by RP-HPLC (MeCN:H2O:0.1% TFA) to yield BA93 (6.7 mg, 35% yield). ESI-MS (M+H)+ m/z calcd 306.1, found 306.0.

Synthesis of 1-isopropyl-3-(3,4,5-trimethoxyphenyl)-1H-pyrazolo[3,4-d]pyrimidin-4-amine (BA64). A solution of 3,4,5-trimethoxyphenylboronic acid (123 mg, 0.58 mmol) in EtOH (3.3 ml) was added to a solution of 3-iodo-1-isopropyl-1H-pyrazolo[3,4-d]pyrimidin-4-amine (70 mg, 0.23 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by silica gel column chromatography [MeOH—CH2Cl2, 2:98] to yield BA64 (70 mg, 89% yield). ESI-MS (M+H)+ m/z calcd 344.1, found 344.0.

Synthesis of 1-isopropyl-3-(2,3-dimethoxyphenyl)-1H-pyrazolo[3,4-d]pyrimidin-4-amine (BA65). A solution 2,3-dimethoxyphenylboronic acid (105 mg, 0.58 mmol) in EtOH (3.3 ml) was added to a solution of 3-iodo-1-isopropyl-1H-pyrazolo[3,4-d]pyrimidin-4-amine (70 mg, 0.23 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by silica gel column chromatography [MeOH—CH2Cl2, 2:98] to yield BA65 (63 mg, 88% yield). ESI-MS (M+H)+ m/z calcd 314.1, found 314.1.

Synthesis of 1-isopropyl-3-(2,4-dimethoxypyrimidin-5-yl)-1H-pyrazolo[3,4-d]pyrimidin-4-amine (BA66). A solution 2,4-dimethoxypyrimidin-5-yl-5-boronic acid (106 mg, 0.58 mmol) in EtOH (3.3 ml) was added to a solution of 3-iodo-1-isopropyl-1H-pyrazolo[3,4-d]pyrimidin-4-amine (70 mg, 0.23 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by silica gel column chromatography [MeOH—CH2Cl2, 2:98] to yield BA66. ESI-MS (M+H)+ m/z calcd 316.1, found 316.0.

Synthesis of 1-cyclopentyl-3-(3-fluoro-5-methoxyphenyl)-1H-pyrazolo[3,4-d]pyrimidin-4-amine (BA79). 3-fluoro-5-methoxybenzoic acid (5 g, 0.029 mol) was stirred in CH2Cl2 (50 ml) at 0° C. under an argon atmosphere. DMF (9 drops, catalytic) was added, followed by oxalyl chloride (12.7 ml, 0.147 mol). Reaction was warmed to room temperature then stirred under argon for one hour. Reaction was concentrated in vacuo to yield 3-fluoro-5-methoxybenzoyl chloride (BA67).

A solution of malononitrile (2.87 g, 0.044 mol) in dry THF (50 ml) was stirred at 0° C. under an argon atmosphere. NaH in paraffin oil (4.64 g, 0.116 mol) was added piece-wise to solution. 3-fluoro-5-methoxybenzoyl chloride (BA67, 0.029 mol) was dissolved in 50 ml dry THF and added slowly to reaction. Reaction was warmed to room temperature and stirred under argon for 24 hours. 1N HCl (200 ml) was slowly added, then reaction mixture was extracted with EtOAc. Organic phases were combined, dried with magnesium sulfate, then concentrated in vacuo to yield 2-((3-fluoro-5-methoxyphenyl)(methoxy)methylene)malononitrile (BA69).

2-((3-fluoro-5-methoxyphenyl)(methoxy)methylene)malononitrile (BA69, 0.029 mol) stirred in EtOH (20 ml) at room temperature under an argon atmosphere. Hydrazine (1.4 ml, 29 mmol) was added and reaction was left stirring for 90 minutes. Reaction mixture was concentrated in vacuo and dried on vacuum pump overnight to yield intermediate 5-amino-3-(3-fluoro-5-methoxyphenyl)-1H-pyrazole-4-carbonitrile (BA73). Formamide (20 ml) was added and reaction was heated to 180° C. under an argon atmosphere overnight. Reaction was cooled and dH2O was added (40 ml) forcing a white precipitate out of solution. Precipitate was collected and washed with dH2O. Solid was dried and purified by silica gel column chromatography [MeOH—CH2Cl2, 10:90] to yield 3-(3-fluoro-5-methoxyphenyl)-1H-pyrazolo[3,4-d]pyrimidin-4-amine (BA75).

3-(3-fluoro-5-methoxyphenyl)-1H-pyrazolo[3,4-d]pyrimidin-4-amine (BA75, 100 mg, 0.386 mmol) was dissolved in DMF (10 ml). K2CO3 (250 mg, 1.54 mmol) was added and reaction was stirred at room temperature under an argon atmosphere. Iodocyclopentane (0.134 ml, 1.16 mmol) was added with a syringe and reaction was stirred for 2 hours. Solid K2CO3 was removed by filtration. Solvent was partially removed in vacuo. Sodium citrate (50 ml) was added and reaction was extracted with EtOAc. Organic phases concentrated in vacuo and purified using by RP-HPLC (MeCN:H2O:0.1% TFA) to yield BA79.

Synthesis of 1-cyclopentyl-3-(3-fluoro-5-methoxyphenyl)-1H-pyrazolo[3,4-d]pyrimidin-4-amine (BA79d). 1-cyclopentyl-3-(3-fluoro-5-methoxyphenyl)-1H-pyrazolo[3,4-d]pyrimidin-4-amine (BA79, 0.386 mmol) was dissolved in CH2Cl2 (2 ml). BBr3 (4 mL, 4 mol) was added slowly with a syringe, while stirring. The reaction was stirred at room temperature for 2 hours then concentrated in vacuo and purified using by RP-HPLC (MeCN:H2O:0.1% TFA) to yield BA79 (69 mg, 57% yield).

Synthesis of 1-cyclopentyl-3-iodo-1H-pyrazolo[3,4-d]pyrimidin-4-amine (BA80). A solution of 3-iodo-1H-pyrazolo[3,4-d]pyrimidin-4-amine (400 mg, 1.53 mmol) and K2CO3 (1 g, 6 mmol) in DMF (5 ml) was stirred at room temperature under an argon atomosphere. Iodocyclopentane (1.0 g, 0.0084 mol) was added with a syringe. Reaction was refluxed under argon atmosphere for 2 hours. Solid K2CO3 was removed by filtration. Solvent was partially removed in vacuo. Sodium citrate (50 ml) was added and reaction was extracted with EtOAc. Organic phases concentrated in vacuo and purified using silica gel column chromatography [MeOH—CH2Cl2, 5:95] yielding BA80 (300 mg, 60% yield). ESI-MS (M+H)+ m/z calcd 330.0, found 330.0.

Synthesis of 1-(3-(4-amino-1-isopropyl-1H-pyrazolo[3,4-d]pyrimidin-3-yl)phenyl)ethanone (BA81, BA81d & BA81dd). A solution of tert-butyl 2-methoxy-4-(4,4,5,5-tetramethyl-1,3,2-dioxaborolan-2-yl)phenylcarbamate (200 mg, 0.76 mmol) in EtOH (3.3 ml) was added to a solution of 1-cyclopentyl-3-iodo-1H-pyrazolo[3,4-d]pyrimidin-4-amine (BA80, 100 mg, 0.30 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified using silica gel column chromatography [MeOH—CH2Cl2, 5:95] yielding BA81. BA81 was dissolved in 50:50 CH2Cl2:TFA and stirred for one hour at room temperature. The reaction mixture was concentrated in vacuo and purified using by RP-HPLC (MeCN:H2O:0.1% TFA) to yield BA81d. BA81d was dissolved in CH2Cl2 (2 ml) and BBr3 (4 mL, 4 mol) was added slowly with a syringe, while stirring. The reaction was stirred at room temperature for 2 hours then concentrated in vacuo and purified using by RP-HPLC (MeCN:H2O:0.1% TFA) to yield BA81dd.

Synthesis of 3-(3-bromo-5-methoxyphenyl)-1-isopropyl-1H-pyrazolo[3,4-d]pyrimidin-4-amine (BA85). A solution of 2-(3-bromo-5-methoxyphenyl)-4,4,5,5-tetramethyl-1,3,2-dioxaborolane (137 mg, 0.43 mmol) in EtOH (3.3 ml) was added to a solution of 3-iodo-1-isopropyl-1H-pyrazolo[3,4-d]pyrimidin-4-amine (65 mg, 0.216 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA85 (28 mg, 36% yield). ESI-MS (M+H)+ m/z calcd 362.1, found 362.0.

Synthesis of 3-(4-amino-1-isopropyl-1H-pyrazolo[3,4-d]pyrimidin-3-yl)-5-bromophenol (BA87). 3-(3-bromo-5-methoxyphenyl)-1-isopropyl-1H-pyrazolo[3,4-d]pyrimidin-4-amine (BA85, 0.1 mmol) was dissolved in CH2Cl2 (1 ml) and BBr3 (1 mL, 1 mol) was added slowly with a syringe, while stirring. The reaction was stirred at room temperature for 35 minutes then concentrated in vacuo and purified using by RP-HPLC (MeCN:H2O:0.1% TFA) to yield BA87 (10.7 mg, 31% yield). ESI-MS (M+H)+ m/z calcd 348.0, found 348.0.

Synthesis of tert-butyl 5-(4-amino-1-isopropyl-1H-pyrazolo[3,4-d]pyrimidin-3-yl)-1H-indole-1-carboxylate (BA86). A solution of tert-butyl 5-(4,4,5,5-tetramethyl-1,3,2-dioxaborolan-2-yl)-1H-indole-1-carboxylate (212 mg, 0.61 mmol) in EtOH (3.3 ml) was added to a solution of 3-iodo-1-isopropyl-1H-pyrazolo[3,4-d]pyrimidin-4-amine (75 mg, 0.25 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O) to yield BA86 (9.3 mg, 9% yield). ESI-MS (M+H)+ m/z calcd 362.1, found 362.0.

Synthesis of 3-(1H-indol-5-yl)-1-isopropyl-1H-pyrazolo[3,4-d]pyrimidin-4-amine (BA89). Tert-butyl 5-(4-amino-1-isopropyl-1H-pyrazolo[3,4-d]pyrimidin-3-yl)-1H-indole-1-carboxylate (BA86, 9 mg, 0.022 mmol) was dissolved in 50:50 CH2Cl2:TFA and stirred for one hour at room temperature. The reaction mixture was concentrated in vacuo and purified using by RP-HPLC (MeCN:H2O:0.1% TFA) to yield BA89 (4.8 mg, 75% yield). ESI-MS (M+H)+ m/z calcd 293.1, found 293.0.

Synthesis of tert-butyl 5-(4-amino-1-cyclopentyl-1H-pyrazolo[3,4-d]pyrimidin-3-yl)-1H-indole-1-carboxylate (BA88). A solution of tert-butyl 5-(4,4,5,5-tetramethyl-1,3,2-dioxaborolan-2-yl)-1H-indole-1-carboxylate (130 mg, 0.38 mmol) in EtOH (3.3 ml) was added to a solution of 3-iodo-1-isopropyl-1H-pyrazolo[3,4-d]pyrimidin-4-amine (50 mg, 0.15 mmol) in DME (12 ml). Pd(PPh3)4 (30 mg, 0.03 mmol) and saturated Na2CO3 (1.9 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O) to yield BA88. ESI-MS (M+H)+ m/z calcd 419.2, found 419.1.

Synthesis of 3-(1H-indol-5-yl)-1-isopropyl-1H-pyrazolo[3,4-d]pyrimidin-4-amine (BA94). Tert-butyl 5-(4-amino-1-cyclopentyl-1H-pyrazolo[3,4-d]pyrimidin-3-yl)-1H-indole-1-carboxylate (BA88) was dissolved in 50:50 CH2Cl2:TFA and stirred for one hour at room temperature. The reaction mixture was concentrated in vacuo and purified using by RP-HPLC (MeCN:H2O:0.1% TFA) to yield BA89 (6.3 mg). ESI-MS (M+H)+ m/z calcd 319.1, found 319.2.

Synthesis of 1-cyclopentyl-3-(3,4-dimethoxyphenyl)-1H-pyrazolo[3,4-d]pyrimidin-4-amine (BA90). A solution of 3,4-dimethoxyphenylboronic acid (41 mg, 0.23 mmol) in EtOH (1.65 ml) was added to a solution of 3-iodo-1-isopropyl-1H-pyrazolo[3,4-d]pyrimidin-4-amine (30 mg, 0.09 mmol) in DME (6 ml). Pd(PPh3)4 (30 mg, 0.03 mmol) and saturated Na2CO3 (0.95 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O) to yield BA90 (8.4 mg, 28% yield). ESI-MS (M+H)+ m/z calcd 340.2, found 340.1.

Synthesis of 3-(1H-indol-4-yl)-1-isopropyl-1H-pyrazolo[3,4-d]pyrimidin-4-amine (BA91). A solution of 1H-indol-4-yl-4-boronic acid (40 mg, 0.25 mmol) in EtOH (1.65 ml) was added to a solution of 3-iodo-1-isopropyl-1H-pyrazolo[3,4-d]pyrimidin-4-amine (30 mg, 0.1 mmol) in DME (6 ml). Pd(PPh3)4 (30 mg, 0.03 mmol) and saturated Na2CO3 (0.95 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA91 (14.6 mg, 50% yield). ESI-MS (M+H)+ m/z calcd 293.1, found 293.1.

Synthesis of 1-cyclopentyl-3-(1H-indol-4-yl)-1H-pyrazolo[3,4-d]pyrimidin-4-amine (BA92). A solution of 1H-indol-4-yl-4-boronic acid (30 mg, 0.19 mmol) in EtOH (1.65 ml) was added to a solution of 3-iodo-1-isopropyl-1H-pyrazolo[3,4-d]pyrimidin-4-amine (25 mg, 0.076 mmol) in DME (6 ml). Pd(PPh3)4 (30 mg, 0.03 mmol) and saturated Na2CO3 (0.95 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA92 (23 mg, 95% yield). ESI-MS (M+H)+ m/z calcd 319.2, found 319.1.

Synthesis of 3-(2,3-dihydrobenzofuran-5-yl)-1-isopropyl-1H-pyrazolo[3,4-d]pyrimidin-4-amine (BA95). A solution of 2,3-dihydro-1-benzofuran-5-ylboronic acid (38 mg, 0.23 mmol) in EtOH (1.65 ml) was added to a solution of 3-iodo-1-isopropyl-1H-pyrazolo[3,4-d]pyrimidin-4-amine (30 mg, 0.1 mmol) in DME (6 ml). Pd(PPh3)4 (30 mg, 0.03 mmol) and saturated Na2CO3 (0.95 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA95 (15.7 mg, 59% yield). ESI-MS (M+H)+ m/z calcd 296.1, found 296.1.

Synthesis of 3-(benzofuran-5-yl)-1-isopropyl-1H-pyrazolo[3,4-d]pyrimidin-4-amine (BA96). A solution of 5-(4,4,5,5-tetramethyl-1,3,2-dioxaborolan-2-yl)-1-benzofuran (56 mg, 0.23 mmol) in EtOH (1.65 ml) was added to a solution of 3-iodo-1-isopropyl-1H-pyrazolo[3,4-d]pyrimidin-4-amine (30 mg, 0.1 mmol) in DME (6 ml). Pd(PPh3)4 (30 mg, 0.03 mmol) and saturated Na2CO3 (0.95 ml) were added and the reaction was heated to 80° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield BA96 (19 mg, 72% yield). ESI-MS (M+H)+ m/z calcd 296.1, found 296.1.

Synthesis of 5-(4-amino-1-cyclopentyl-1H-pyrazolo[3,4-d]pyrimidin-3-yl)-2-ethoxyphenol (BA98). 1-cyclopentyl-3-(4-ethoxy-3-methoxyphenyl)-1H-pyrazolo[3,4-d]pyrimidin-4-amine (ZK359, 25 mg, 0.071 mmol) was dissolved in CH2Cl2 (5 ml) and stirred at −10° C. under an argon atmosphere. After 30 minutes, reaction was brought to 0° C. and stirred for 2.5 hours. Reaction was stirred for additional 4 hours at room temperature, then concentrated in vacuo and purified by RP-HPLC (MeCN:H2O:0.1% TFA) to yield BA98 (3 mg, 13% yield). ESI-MS (M+H)+ m/z calcd 340.1, found 340.1.

Synthesis of 2-(4-(4-amino-1-isopropyl-1H-pyrazolo[3,4-d]pyrimidin-3-yl)-2-methoxyphenylamino)propan-1-ol (BA99). 3-(4-amino-3-methoxyphenyl)-1-isopropyl-1H-pyrazolo[3,4-d]pyrimidin-4-amine (BA20d) (30 mg, 0.10 mmol) was dissolved in DMF (0.400 ml). K2CO3 (55 mg, 0.4 mmol) was added and reaction was stirred at 70° C. 3-bromo-1-propanol (0.050 ml, 0.6 mmol) was added and reaction was stirred overnight. Solid K2CO3 was removed by filtration. Solvent was partially removed in vacuo. Sodium citrate (50 ml) was added and reaction was extracted with saturated NaCl and CH2Cl2. Organic phases concentrated in vacuo and purified by RP-HPLC (MeCN:H2O:0.1% TFA) to yield BA99 (8.4 mg, 24% yield). ESI-MS (M+H)+ m/z calcd 357.2, found 357.1.

Synthesis of 3-iodo-1-methyl-1H-pyrazolo[3,4-d]pyrimidin-4-amine (BA109). A solution of 3-iodo-1H-pyrazolo[3,4-d]pyrimidin-4-amine (2 g, 7.69 mmol) and K2CO3 (4.25 g, 30.8 mmol) in DMF (5 ml) was stirred at room temperature under an argon atmosphere. Iodomethane (1.17 ml, 7.69 mmol) was added with a syringe. Reaction was stirred under an argon atmosphere at room temperature for 2 hours. Solid K2CO3 was removed by filtration. Solvent was partially removed in vacuo. Sodium citrate (50 ml) was added and reaction was extracted with EtOAc. Organic phases concentrated in vacuo and purified using silica gel column chromatography [MeOH—CH2Cl2, 5:95] yielding BA109 (212 mg, 10% yield). ESI-MS (M+H)+ m/z calcd 275.9, found 275.9

General synthetic scheme for BA102, BA105-108, BA10, BA118, BA128-BA135, BA137, BA139-140, BA143, BA147, BA149-BA152, BA156, BA158, BA160-BA162. A solution of boronic acid (2.5 equivalents) in EtOH (1.65 ml) was added to a solution of 3-iodo-1-isopropyl-1H-pyrazolo[3,4-d]pyrimidin-4-amine (BA12, 1 equivalent) in DME (6 ml). Pd(PPh3)4 (15 mg, 0.15 mmol) and saturated Na2CO3 (0.95 ml) were added and the reaction was heated to 90° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield desired products. Products were analyzed by LC-MS.

General synthetic scheme for BA112, BA115, BA121, BA122, BA124, BA136, BA138. BA141, and BA144. A solution of boronic acid (2.5 equivalents) in EtOH (1.65 ml) was added to a solution of 1-cyclopentyl-3-iodo-1H-pyrazolo[3,4-d]pyrimidin-4-amine (BA80, 1 equivalent) in DME (6 ml). Pd(PPh3)4 (15 mg, 0.15 mmol) and saturated Na2CO3 (0.95 ml) were added and the reaction was heated to 90° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield desired products. Products were analyzed by LC-MS.

General synthetic scheme for BA111, BA114, BA116, BA117, BA119, and BA120. A solution of boronic acid (2.5 equivalents) in EtOH (1.65 ml) was added to a solution of 3-iodo-1-methyl-1H-pyrazolo[3,4-d]pyrimidin-4-amine (BA109, 1 equivalent) in DME (6 ml). Pd(PPh3)4 (15 mg, 0.15 mmol) and saturated Na2CO3 (0.95 ml) were added and the reaction was heated to 90° C. under an argon atmosphere overnight. After cooling, the reaction was extracted with saturated NaCl and CH2Cl2. Organic phases were combined, concentrated in vacuo and purified by RP-HPLC (MeCN:H2O:0.1% TFA) to yield desired products. Products were analyzed by LC-MS.

Synthesis of 6-(4-amino-1-isopropyl-1H-pyrazolo[3,4-d]pyrimidin-3-yl)quinolin-2-amine (BA146). 3-(2-chloroquinolin-6-yl)-1-isopropyl-1H-pyrazolo[3,4-d]pyrimidin-4-amine (BA130, 50 mg, 0.15 mmol), acetamide (174 mg, 3.0 mmol) and K2CO3 (104 mg, 0.75 mmol) were combined and heated to 200° C. under an argon atmosphere for one hour. Reaction was cooled, then extracted with H2O and CH2Cl2. Organic phases were combined, concentrated in vacuo and purified by RP-HPLC (MeCN:H2O:0.1% TFA) to yield BA146 (22 mg, 46% yield). ESI-MS (M+H)+ m/z calcd 320.2, found 320.4.

Synthesis of 3-(3-amino-1H-indazol-6-yl)-1-isopropyl-1H-pyrazolo[3,4-d]pyrimidin-4-amine (BA154). 4-(4-amino-1-isopropyl-1H-pyrazolo[3,4-d]pyrimidin-3-yl)-2-fluorobenzonitrile (BA150, 20 mg, 0.07 mmol) was dissolved in n-BuOH (2 ml). Hydrazine monohydrate (0.400 ml) was added and the reaction was heated to 110° C. under an argon atomosphere and left stirring over night. Reaction mixture was concentrated in vacuo and purified by RP-HPLC (MeCN:H2O:0.1% TFA) to yield BA154 (15 mg, 70% yield). ESI-MS (M+H)+ m/z calcd 309.2, found 309.4.

Synthesis of 4-(4-amino-1-isopropyl-1H-pyrazolo[3,4-d]pyrimidin-3-yl)-2-hydroxybenzonitrile (BA155_2). 4-(4-amino-1-isopropyl-1H-pyrazolo[3,4-d]pyrimidin-3-yl)-2-fluorobenzonitrile (BA150, 25 mg, 0.1 mmol) was dissolved in DMF (1 ml). t-BuOK (24 mg, 0.21 mmol) was added and the reaction was stirred at room temperature overnight. Reaction was then heated to 150° C. for 24 hours. The reaction was then concentrated in vacuo and purified by RP-HPLC (MeCN:H2O:0.1% TFA) to yield BA155_2 (21 mg, 89% yield). ESI-MS (M+H)+ m/z calcd 295.1, found 295.4.

Synthesis of 3-(3-aminobenzo[d]isoxazol-5-yl)-1-isopropyl-1H-pyrazolo[3,4-d]pyrimidin-4-amine (BA 157_2) & 5-(4-amino-1-isopropyl-1H-pyrazolo[3,4-d]pyrimidin-3-yl)-2-hydroxybenzonitrile (BA157_3). 5-(4-amino-1-isopropyl-1H-pyrazolo[3,4-d]pyrimidin-3-yl)-2-fluorobenzonitrile (BA151, 20 mg, 0.07 mmol) was dissolved in DMF (1 ml). t-BuOK (24 mg, 0.21 mmol) was added and the reaction was stirred at room temperature overnight. Reaction was then heated to 150° C. for 24 hours. The reaction was then concentrated in vacuo and purified by RP-HPLC (MeCN:H2O:0.1% TFA) to yield BA157_2 (7 mg), ESI-MS (M+H)+ m/z calcd 295.1, found 295.4 and BA157_3 (8 mg), ESI-MS (M+H)+ m/z calcd 310.1, found 310.4.

Synthesis of 3-(3-amino-1H-indazol-6-yl)-1-isopropyl-1H-pyrazolo[3,4-d]pyrimidin-4-amine (BA159). 4-(4-amino-1-isopropyl-1H-pyrazolo[3,4-d]pyrimidin-3-yl)-2,6-difluorobenzaldehyde (BA149, 20 mg, 0.063 mmol) was dissolved in n-BuOH (1 ml). Hydrazine monohydrate (0.400 ml) was added and the reaction was heated to 100° C. under an argon atomosphere and left stirring for 2.5 hours. Reaction mixture was concentrated in vacuo and purified by RP-HPLC (MeCN:H2O:0.1% TFA) to yield BA159 (15 mg, 77% yield). ESI-MS (M+H)+ m/z calcd 312.1, found 312.4.

Synthesis of 4-chloro-7-methyl-5-(naphthalen-2-yl)-7H-pyrrolo[2,3-d]pyrimidine (ZK102). A solution of 4-chloro-5-iodo-7-methyl-7H-pyrrolo[2,3-d]pyrimidine (19 mg, 0.065 mmol), naphthalen-2-yl-2-boronic acid (12.2 mg, 0.071 mmol), $Na_2CO_3$ (68.9 mg, 0.65 mmol) and $PdCl_2(dppf)$ (26.5 mg, 0.00325 mmol) in THF (3 mL) was heated to reflux overnight under an argon atmosphere. Reaction was concentrated in vacuo and purified by RP-HPLC (MeCN:$H_2O$:0.1% TFA) to yield ZK102 (5 mg, 26% yield). ESI-MS (M+H)$^+$ m/z calcd 294.1, found 294.3.

Synthesis of 4-chloro-7-methyl-5-(3-biphenyl)-7H-pyrrolo[2,3-d]pyrimidine (ZK103). A solution of 4-chloro-5-iodo-7-methyl-7H-pyrrolo[2,3-d]pyrimidine (10 mg, 0.034 mmol), 3-biphenyl-boronic acid (7.4 mg, 0.038 mmol), $Na_2CO_3$ (36.1 mg, 0.34 mmol) and $PdCl_2(dppf)$ (1.4 mg, 0.0017 mmol) in THF (10 mL) was heated to reflux overnight under an argon atmosphere. Reaction was concentrated in vacuo and purified by RP-HPLC (MeCN:$H_2O$:0.1% TFA) to yield ZK103 (3 mg, 28% yield). ESI-MS (M+H)$^+$ m/z calcd 320.1, found 320.0.

Synthesis of 3-(4-tert-butylphenyl)-1H-pyrazolo[3,4-d]pyrimidin-4-amine (ZK125). 1-tert-butyl-3-(4-tert-butylphenyl)-1H-pyrazolo[3,4-d]pyrimidin-4-amine was dissolved in a solution of formic acid (1 mL) and conc. HCl (0.1 mL) and heated to reflux for 2 hours. Reaction was concentrated in vacuo and purified by RP-HPLC (MeCN:H$_2$O:0.1% TFA) to yield ZK125 (quant.). ESI-MS (M+H)$^+$ m/z calcd 268.2, found 268.4.

Synthesis of 3-(3-phenoxyphenyl)-1H-pyrazolo[3,4-d]pyrimidin-4-amine (ZK126). 1-tert-butyl-3-(3-phenoxyphenyl)-1H-pyrazolo[3,4-d]pyrimidin-4-amine (50 mg, 0.16 mmol) was dissolved in a solution of formic acid (5 mL) and conc. HCl (0.1 mL) and heated to reflux for 2.5 hours. Reaction was concentrated in vacuo and purified by RP-HPLC (MeCN:H$_2$O:0.1% TFA). ESI-MS (M+H)$^+$ m/z calcd 304.1, found 304.3.

Synthesis of 3-m-tolyl-1H-pyrazolo[3,4-d]pyrimidin-4-amine (ZK127). 1-tert-butyl-3-m-tolyl-1H-pyrazolo[3,4-d]pyrimidin-4-amine (23 mg, 0.1 mmol) was dissolved in a solution of formic acid (1 mL) and conc. HCl (0.3 mL) and heated to reflux for 2.5 hours. Reaction was concentrated in vacuo and purified by RP-HPLC (MeCN:H$_2$O:0.1% TFA). ESI-MS (M+H)$^+$ m/z calcd 226.1, found 226.3.

Synthesis of 3-(3-nitrophenyl)-1H-pyrazolo[3,4-d]pyrimidin-4-amine (ZK128). 1-tert-butyl-3-(3-nitrophenyl)-1H-pyrazolo[3,4-d]pyrimidin-4-amine (23 mg, 0.055 mmol) was dissolved in a solution of formic acid (5 mL) and conc. HCl (0.1 mL) and heated to reflux for 2 hours. Reaction was concentrated in vacuo and purified by RP-HPLC (MeCN:H$_2$O:0.1% TFA). ESI-MS (M+H)$^+$ m/z calcd 257.1, found 257.3.

Synthesis of 3-(benzo[d][1,3]dioxol-6-yl)-1H-pyrazolo[3,4-d]pyrimidin-4-amine (ZK129). 1-tert-butyl-3-(benzo[d][1,3]dioxol-6-yl)-1H-pyrazolo[3,4-d]pyrimidin-4-amine (21 mg, 0.082 mmol) was dissolved in a solution of formic acid (1 mL) and conc. HCl (0.2 mL) and heated to reflux for 2 hours. Reaction was concentrated in vacuo and purified by RP-HPLC (MeCN:H$_2$O:0.1% TFA). ESI-MS (M+H)$^+$ m/z calcd 256.1, found 256.3.

Synthesis of 3-(4-nitrophenyl)-1H-pyrazolo[3,4-d]pyrimidin-4-amine (ZK130). 1-tert-butyl-3-(4-nitrophenyl)-1H-pyrazolo[3,4-d]pyrimidin-4-amine (21 mg, 0.082 mmol) was dissolved in a solution of formic acid (2 mL) and conc. HCl (0.2 mL) and heated to reflux for 30 min. Reaction was concentrated in vacuo and purified by RP-HPLC (MeCN:H$_2$O:0.1% TFA). ESI-MS (M+H)$^+$ m/z calcd 257.1, found 257.3.

Synthesis of 3-(3-(2,6-dichlorobenzyloxy)phenyl)-1H-pyrazolo[3,4-d]pyrimidin-4-amine (ZK131). 1-tert-butyl-3-(3-(2,6-dichlorobenzyloxy)phenyl)-1H-pyrazolo[3,4-d]pyrimidin-4-amine (19.5 mg, 0.05 mmol) was dissolved in a solution of formic acid (2 mL) and conc. HCl (0.2 mL) and heated to reflux for 30 min. Reaction was concentrated in vacuo and purified by RP-HPLC (MeCN:H$_2$O:0.1% TFA). ESI-MS (M+H)$^+$ m/z calcd 386.1, found 386.2.

Synthesis of 3-(2,3-dimethylphenyl)-1H-pyrazolo[3,4-d]pyrimidin-4-amine (ZK132). 1-tert-butyl-3-(2,3-dimethylphenyl)-1H-pyrazolo[3,4-d]pyrimidin-4-amine (34 mg, 0.14 mmol) was dissolved in a solution of formic acid (2 mL) and conc. HCl (0.2 mL) and heated to reflux for 30 min. Reaction was concentrated in vacuo and purified by RP-HPLC (MeCN:H$_2$O:0.1% TFA). ESI-MS (M+H)$^+$ m/z calcd 240.1, found 240.4.

Synthesis of 2-(4-amino-1H-pyrazolo[3,4-d]pyrimidin-3-yl)phenol (ZK133). 1-tert-butyl-2-(4-amino-1H-pyrazolo[3,4-d]pyrimidin-3-yl)phenol (5 mg, 0.014 mmol) was dissolved in a solution of formic acid (2 mL) and conc. HCl (0.2 mL) and heated to reflux for 30 min. Reaction was concentrated in vacuo and purified by RP-HPLC (MeCN:H$_2$O:0.1% TFA). ESI-MS (M+H)$^+$ m/z calcd 228.1, found 228.3.

Synthesis of 3-o-tolyl-1H-pyrazolo[3,4-d]pyrimidin-4-amine (ZK134). 1-tert-butyl-3-o-tolyl-1H-pyrazolo[3,4-d]pyrimidin-4-amine was dissolved in a solution of formic acid (2 mL) and conc. HCl (0.2 mL) and heated to reflux for 30 min. Reaction was concentrated in vacuo and purified by RP-HPLC (MeCN:H$_2$O:0.1% TFA). ESI-MS (M+H)$^+$ m/z calcd 226.1, found 226.3.

Synthesis of 3-(3-aminophenyl)-1H-pyrazolo[3,4-d]pyrimidin-4-amine (ZK135). 1-tert-butyl-3-(3-aminophenyl)-1H-pyrazolo[3,4-d]pyrimidin-4-amine was dissolved in a solution of formic acid (2 mL) and conc. HCl (0.2 mL) and heated to reflux for 30 min. Reaction was concentrated in vacuo and purified by RP-HPLC (MeCN:H$_2$O:0.1% TFA). ESI-MS (M+H)$^+$ m/z calcd 227.1, found 227.3.

Synthesis of 3-(3-(benzyloxy)phenyl)-1H-pyrazolo[3,4-d]pyrimidin-4-amine (ZK136). 1-tert-butyl-3-(3-(benzyloxy)phenyl)-1H-pyrazolo[3,4-d]pyrimidin-4-amine (19 mg, 0.052 mmol) was dissolved in a solution of formic acid (1 mL) and conc. HCl (0.1 mL) and heated to reflux for 30 min. Reaction yielded a mixture of ZK136 and 3-(4-amino-1H-pyrazolo[3,4-d]pyrimidin-3-yl)phenol (ZK138). Reaction was concentrated in vacuo and the products purified by RP-HPLC (MeCN:H$_2$O:0.1% TFA). ZK136: ESI-MS (M+H)$^+$ m/z calcd 318.1, found 318.3. ZK138: ESI-MS (M+H)$^+$ m/z calcd 228.1, found 228.3.

Synthesis of 3-(4-aminophenyl)-1H-pyrazolo[3,4-d]pyrimidin-4-amine (ZK137). 1-tert-butyl-3-(4-aminophenyl)-1H-pyrazolo[3,4-d]pyrimidin-4-amine (9 mg, 0.032 mmol) was dissolved in a solution of formic acid (1 mL) and conc. HCl (0.2 mL) and heated to reflux. The reaction was allowed to proceed 30 min., then concentrated in vacuo and the products purified by RP-HPLC (MeCN:H$_2$O:0.1% TFA). ESI-MS (M+H)$^+$ m/z calcd 227.1, found 227.3.

Synthesis of 3-(1,2,3,4-tetrahydronaphthalen-2-yl)-1H-pyrazolo[3,4-d]pyrimidin-4-amine (ZK139). 1-tert-butyl-3-(1,2,3,4-tetrahydronaphthalen-2-yl)-1H-pyrazolo[3,4-d]pyrimidin-4-amine (9 mg, 0.029 mmol) was dissolved in a solution of formic acid (1 mL) and conc. HCl (0.1 mL) and heated to reflux. The reaction was allowed to proceed 30 min., then concentrated in vacuo and the products purified by RP-HPLC (MeCN:H$_2$O:0.1% TFA). ESI-MS (M+H)$^+$ m/z calcd 266.1, found 266.4.

Synthesis of 5-iodo-7-methyl-7H-pyrrolo[2,3-d]pyrimidin-4-amine (ZK140). 4-chloro-5-iodo-7-methyl-7H-pyrrolo[2,3-d]pyrimidine (90 mg, 0.31 mmol) was taken up in 7N NH$_3$/MeOH and heated in a sealed tube at 110° C. overnight. Reaction was concentrated in vacuo to give a brown/off-white solid.

Synthesis of 3-p-tolyl-1H-pyrazolo[3,4-d]pyrimidin-4-amine (ZK141). 1-tert-butyl-3-p-tolyl-1H-pyrazolo[3,4-d]pyrimidin-4-amine was dissolved in a solution of formic acid (1 mL) and conc. HCl (0.1 mL) and heated to reflux. The reaction was allowed to proceed 30 min., then concentrated in vacuo and the products purified by RP-HPLC (MeCN:H$_2$O:0.1% TFA). ESI-MS (M+H)$^+$ m/z calcd 226.1, found 226.3.

Synthesis of 3-(4-biphenyl)-1H-pyrazolo[3,4-d]pyrimidin-4-amine (ZK142). 1-tert-butyl-3-(4-biphenyl)-1H-pyrazolo[3,4-d]pyrimidin-4-amine (22 mg, 0.066 mmol) was dissolved in a solution of formic acid (1 mL) and conc. HCl (0.1 mL) and heated to reflux. The reaction was allowed to proceed 30 min., then concentrated in vacuo and the products purified by RP-HPLC (MeCN:H$_2$O:0.1% TFA). ESI-MS (M+H)$^+$ m/z calcd 288.1, found 288.3.

Synthesis of 3-(4-phenoxyphenyl)-1H-pyrazolo[3,4-d]pyrimidin-4-amine (ZK143). 1-tert-butyl-3-(4-phenoxyphenyl)-1H-pyrazolo[3,4-d]pyrimidin-4-amine (19 mg, 54.1 mmol) was dissolved in a solution of formic acid (1 mL) and conc. HCl (0.1 mL) and heated to reflux. The reaction was allowed to proceed 30 min., then concentrated in vacuo and the products purified by RP-HPLC (MeCN:H$_2$O:0.1% TFA). ESI-MS (M+H)$^+$ m/z calcd 304.1, found 304.3.

Synthesis of 1-benzyl-3-(naphthalen-2-yl)-1H-pyrazolo[3,4-d]pyrimidin-4-amine (ZK147). 3-(naphthalen-2-yl)-1H-pyrazolo[3,4-d]pyrimidin-4-amine (110 mg, 0.42 mmol) was dissolved in DMF (2 mL) and K$_2$CO$_3$ (220 mg, 1.6 mmol) and benzyl bromide (71.8 mg, 0.42 mmol) were added. The reaction was heated to 60° C. overnight, then cooled to RT and poured into water (30 mL). The precipitate was collected by filtration and then purified further by silica gel chromatography (5% MeOH/CH$_2$Cl$_2$) to yield a white solid.

Synthesis of 5-(4-(benzyloxy)phenyl)-7-methyl-7H-pyrrolo[2,3-d]pyrimidin-4-amine (ZK150). A solution of 5-iodo-7-methyl-7H-pyrrolo[2,3-d]pyrimidin-4-amine (5 mg, 0.018 mmol), 4-(benzyloxy)phenylboronic acid (21 mg, 0.091 mmol), K$_3$PO$_4$ (19.3 mg, 0.091 mmol) and Pd(PPh$_3$)$_4$ (12.5 mg, 0.011 mmol) in DMF (3 mL) was heated to 60° C. under an argon atmosphere. Reaction was concentrated in vacuo and purified by RP-HPLC (MeCN:H$_2$O:0.1% TFA). ESI-MS (M+H)$^+$ m/z calcd 331.1, found 331.3.

Synthesis of 5-(3-biphenyl)-7-methyl-7H-pyrrolo[2,3-d]pyrimidin-4-amine (ZK151). A solution of 5-iodo-7-methyl-7H-pyrrolo[2,3-d]pyrimidin-4-amine (5 mg, 0.018 mmol), 3-biphenylboronic acid (18 mg, 0.091 mmol), K$_3$PO$_4$ (19.3 mg, 0.091 mmol) and Pd(PPh$_3$)$_4$ (12.5 mg, 0.011 mmol) in DMF (3 mL) was heated to 60° C. under an argon atmosphere. Reaction was concentrated in vacuo and purified by RP-HPLC (MeCN:H$_2$O:0.1% TFA). ESI-MS (M+H)$^+$ m/z calcd 301.1, found 301.3.

Synthesis of 5-(benzo[b]thiophen-2-yl)-7-methyl-7H-pyrrolo[2,3-d]pyrimidin-4-amine (ZK152). A solution of 5-iodo-7-methyl-7H-pyrrolo[2,3-d]pyrimidin-4-amine (5 mg, 0.018 mmol), benzo[b]thiophen-2-yl-2-boronic acid (16 mg, 0.091 mmol), K$_3$PO$_4$ (19.3 mg, 0.091 mmol) and Pd(PPh$_3$)$_4$ (12.5 mg, 0.011 mmol) in DMF (3 mL) was heated to 60° C. under an argon atmosphere. Reaction was concentrated in vacuo and purified by RP-HPLC (MeCN:H$_2$O:0.1% TFA). ESI-MS (M+H)$^+$ m/z calcd 281.1, found 281.3.

Synthesis of 3-(naphthalen-2-yl)-1-phenethyl-1H-pyrazolo[3,4-d]pyrimidin-4-amine (ZK155). 2-(methoxy(naphthalen-6-yl)methylene)malononitrile (100 mg, 0.43 mmol) and phenethylhydrazine hydrogen chloride (58.5 mg, 0.43 mmol) were dissolved in EtOH (3 mL) and TEA (60 µL, 0.43 mmol) and heat to reflux for one hour. The product was extracted with diethylether and concentrated in vacuo. This concentrate was then dissolved in formamide (10 mL) and heated to 160-180° C. overnight. The following day the reaction was cooled, poured into water, and the precipitated product collected by filtration. ESI-MS (M+H)$^+$ m/z calcd 366.2, found 366.2.

Synthesis of 1-isopropyl-3-(naphthalen-2-yl)-1H-pyrazolo[3,4-d]pyrimidin-4-amine (ZK156). 2-(methoxy(naphthalen-6-yl)methylene)malononitrile (100 mg, 0.43 mmol) and isopropylhydrazine hydrogen chloride (47.3 mg, 0.43 mmol) were dissolved in EtOH (3 mL) and TEA (1 eq.) and heat to reflux for one hour. The product was extracted with diethylether and concentrated in vacuo. This concentrate was then dissolved in formamide (10 mL) and heated to 160-180° C. overnight. The following day the reaction was cooled, poured into water, and the precipitated product collected by filtration. ESI-MS (M+H)$^+$ m/z calcd 304.2, found 304.2.

Synthesis of 1-ethyl-3-(naphthalen-2-yl)-1H-pyrazolo[3,4-d]pyrimidin-4-amine (ZK157). 3-(naphthalen-2-yl)-1H-pyrazolo[3,4-d]pyrimidin-4-amine (100 mg, 0.42 mmol) was dissolved in DMF (3 mL) and K$_2$CO$_3$ (220 mg, 1.6 mmol) and ethyl iodide (37 µL, 0.46 mmol) were added. The reaction was heated to 60° C. overnight, then cooled to RT and poured into water (30 mL). The precipitate was collected by filtration. ESI-MS (M+H)$^+$ m/z calcd 290.1, found 290.2.

Synthesis of 1-cyclopentyl-3-(naphthalen-2-yl)-1H-pyrazolo[3,4-d]pyrimidin-4-amine (ZK158). 3-(naphthalen-2-yl)-1H-pyrazolo[3,4-d]pyrimidin-4-amine (100 mg, 0.42 mmol) was dissolved in DMF (3 mL) and K$_2$CO$_3$ (220 mg, 1.6 mmol) and cyclopentyl bromide (49.5 µL, 0.46 mmol) were added. The reaction was heated to 60° C. overnight, then cooled to RT and poured into water (30 mL). The precipitate was collected by filtration. ESI-MS (M+H)$^-$ m/z calcd 330.2, found 330.2.

Synthesis of 1-allyl-3-(naphthalen-2-yl)-1H-pyrazolo[3,4-d]pyrimidin-4-amine (ZK159). 3-(naphthalen-2-yl)-1H-pyrazolo[3,4-d]pyrimidin-4-amine (50 mg, 0.21 mmol) was dissolved in DMF (1.5 mL) and K$_2$CO$_3$ (110 mg, 0.8 mmol) and allyl iodide (23 µL, 0.25 mmol) were added. The reaction was heated to 60° C. overnight, then cooled to RT and poured into water (30 mL). The precipitate was collected by filtration. ESI-MS (M+H)$^+$ m/z calcd 302.1, found 302.2.

Synthesis of 2-(4-amino-3-(naphthalen-2-yl)-1H-pyrazolo[3,4-d]pyrimidin-1-yl)acetamide (ZK162). 3-(naphthalen-2-yl)-1H-pyrazolo[3,4-d]pyrimidin-4-amine (50 mg, 0.21 mmol) was dissolved in DMF (1.5 mL) and K$_2$CO$_3$ (110 mg, 0.8 mmol) and iodoacetamide (46 mg, 0.25 mmol) were added. The reaction was heated to 60° C. overnight, then cooled to RT and poured into water (30 mL). The precipitate was collected by filtration. ESI-MS (M+H)$^-$ m/z calcd 319.1, found 319.2.

Synthesis of 1-(cyclopropylmethyl)-3-(naphthalen-2-yl)-1H-pyrazolo[3,4-d]pyrimidin-4-amine (ZK165). 3-(naphthalen-2-yl)-1H-pyrazolo[3,4-d]pyrimidin-4-amine (50 mg, 0.21 mmol) was dissolved in DMF (1.5 mL) and K$_2$CO$_3$ (110 mg, 0.8 mmol) and cyclopropyl methyl bromide (22 µL, 0.25 mmol) were added. The reaction was heated to 60° C. overnight, then cooled to RT and poured into water (30 mL). The precipitate was collected by filtration. ESI-MS (M+H)$^+$ m/z calcd 316.2, found 316.2.

Synthesis of 1-isopentyl-3-(naphthalen-2-yl)-1H-pyrazolo[3,4-d]pyrimidin-4-amine (ZK161). 3-(naphthalen-2-yl)-1H-pyrazolo[3,4-d]pyrimidin-4-amine (50 mg, 0.21 mmol) was dissolved in DMF (1.5 mL) and K$_2$CO$_3$ (110 mg, 0.8 mmol) and isobutyl bromide were added. The reaction was heated to 60° C. overnight, then cooled to RT and poured into water (30 mL). The precipitate was collected by filtration. ESI-MS (M+H)$^+$ m/z calcd 332.2, found 332.3.

Synthesis of 3-(naphthalen-2-yl)-1-((E)-3-phenylprop-1-enyl)-1H-pyrazolo[3,4-d]pyrimidin-4-amine (ZK167). 3-(naphthalen-2-yl)-1H-pyrazolo[3,4-d]pyrimidin-4-amine (50 mg, 0.21 mmol) was dissolved in DMF (1.5 mL) and K$_2$CO$_3$ (110 mg, 0.8 mmol) and 1-((E)-3-bromoprop-1-enyl)benzene were added. The reaction was heated to 60° C. overnight, then cooled to RT and poured into water (30 mL). The precipitate was collected by filtration. ESI-MS (M+H)$^+$ m/z calcd 378.2, found 378.2.

Synthesis of 3-(naphthalen-2-yl)-1-(prop-2-ynyl)-1H-pyrazolo[3,4-d]pyrimidin-4-amine (ZK168). 3-(naphthalen-2-yl)-1H-pyrazolo[3,4-d]pyrimidin-4-amine (50 mg, 0.21 mmol) was dissolved in DMF (1.5 mL) and K$_2$CO$_3$ (110 mg, 0.8 mmol) and propargylbromide were added. The reaction was heated to 60° C. overnight, then cooled to RT and poured into water (30 mL). The precipitate was collected by filtration. ESI-MS (M+H)$^+$ m/z calcd 300.1, found 300.2

Synthesis of 3-ethoxy-4-methoxybenzoyl chloride (ZK299). 3-ethoxy-4-methoxybenzoic acid (5 g, 25.5 mmol) was added to a solution of CH$_2$Cl$_2$ (40 mL) and benzene (20 mL) in a flame-dried 150 mL round bottom flask. Anhydrous DMF (9 drops) was added and the solution was cooled on ice. Oxalyl chloride (11 mL, 128 mmol) was added dropwise, and the reaction was then allowed to warm to RT. The reaction was stirred at RT for 90 minutes, then concentrated in vacuo yield an off-white solid. The solid was placed on a high-vacuum line for 2 hours, and then taken onto the next step without further characterization.

Synthesis of 2-((3-ethoxy-4-methoxyphenyl)(hydroxy)methylene)malononitrile (ZK301). NaH (2.2 g, 56 mmol, 60% dispersion in paraffin oil) was added to a solution of malononitrile (1.85 g, 28 mmol) in THF (30 mL) on ice. 3-ethoxy-4-methoxybenzoyl chloride (25.5 mmol) was dissolved in THF (50 mL) and added the first solution dropwise by syringe at 0° C. The ice was then removed and the reaction was allowed to proceed at RT for 60 min. 1N HCl (100 mL) was added and the solution was extracted three times with EtOAc. The organic phase was dried with $MgSO_4$, filtered, and concentrated in vacuo to give an orange solid that was taken onto the next step without further characterization.

Synthesis of 2-((3-ethoxy-4-methoxyphenyl)(methoxy)methylene)malononitrile (ZK302). 2-((3-ethoxy-4-methoxyphenyl)(hydroxy)methylene)malononitrile (25.5 mmol) and sodium bicarbonate (17 g, 204 mmol) were combined in a solution of 1,4-dioxane (48 mL) and water (8 mL). Dimethylsulphate (17 mL, 178 mmol) was slowly added and the reaction was heated to 80-90° C. for 2 hours. The reaction was cooled to RT, water was added, and the aqueous phase extracted three times with EtOAc (200 mL). The organic phases were combined, dried with $MgSO_4$, and filtered to give a red oil. The oil was purified by silica gel chromatography (10% EtOAc/Hexanes, $R_f$~0.1) to give a white solid (3.59 g, 54.5% yield over three steps). ESI-MS $(M+H)^+$ m/z calcd 259.1, found 259.0.

Synthesis of 5-amino-3-(3-ethoxy-4-methoxyphenyl)-1-isopropyl-1H-pyrazole-4-carbonitrile (ZK303). 2-((3-ethoxy-4-methoxyphenyl)(methoxy)methylene)malononitrile (200 mg, 0.78 mmol), isopropylhydrazine hydrogen chloride (86 mg, 0.78 mmol), and triethylamine (0.10 mL, 0.78 mmol) were combined in ethanol (5 mL) and heated to reflux for 90 minutes. The reaction was then cooled to RT, water was added and the aqueous phase was extracted three times with EtOAc. The organic phase was concentrated and carried onto the next step without further characterization. ESI-MS $(M+H)^+$ m/z calcd 301.1, found 301.0

Synthesis of 3-(3-ethoxy-4-methoxyphenyl)-1-isopropyl-1H-pyrazolo[3,4-d]pyrimidin-4-amine (ZK305). 5-amino-3-(3-ethoxy-4-methoxyphenyl)-1-isopropyl-1H-pyrazole-4-carbonitrile was dissolved in formamide (20 mL) and heated to 180° C. overnight. The next day the reaction was cooled to RT, water was added, and the precipitate was collected by filtration. The precipitate was then dissolved in $CH_2Cl_2$/MeOH and passed through a silica plug. The product was then lyophilized from benzene to yield an off-white solid (48 mg, 19% over two steps). ESI-MS $(M+H)^+$ m/z calcd 328.2, found 328.0.

Synthesis of 5-amino-3-(3-ethoxy-4-methoxyphenyl)-1-(2-hydroxyethyl)-1H-pyrazole-4-carbonitrile (ZK304). 2-((3-ethoxy-4-methoxyphenyl)(methoxy)methylene)malononitrile (200 mg, 0.78 mmol), 2-hydroxyethylhydrazine (0.056 mL, 0.78 mmol), and triethylamine (0.10 mL, 0.78 mmol) were combined in ethanol (5 mL) and heated to reflux for 90 minutes. The reaction was then cooled to RT, water was added and the aqueous phase was extracted three times with EtOAc, $CH_2Cl_2$, and $CHCl_3$. The organic phase was concentrated and carried onto the next step without further characterization. ESI-MS $(M+H)^+$ m/z calcd 303.1, found 303.0.

2-(4-amino-3-(3-ethoxy-4-methoxyphenyl)-1H-pyrazolo[3,4-d]pyrimidin-1-yl)ethanol (ZK306). 5-amino-3-(3-ethoxy-4-methoxyphenyl)-1-(2-hydroxyethyl)-1H-pyrazole-4-carbonitrile was dissolved in formamide (20 mL) and heated to 180° C. overnight. The next day the reaction was cooled to RT, water was added, and the precipitate was collected by filtration. The precipitate was then dissolved in $CH_2Cl_2$/MeOH and passed through a silica plug. The product was then lyophilized from benzene to yield a brown solid (6.4 mg, 2.5% over two steps). ESI-MS $(M+H)^+$ m/z calcd 330.1, found 330.0.

B. Structural Studies

Crystal structures of p110γ have been reported, alone and in complex with ATP or pan-specific inhibitors such as LY294002 and wortmannin (Walker et al., 2000; Walker et al., 1999). To explore how potent and selective inhibitors bind, the crystal structures of PI3-K inhibitors from three chemotypes bound to human p110γ were determined at 2.5-2.6 Å resolution: the quinazoline purine PIK-39, the imidazopyridine PIK-90 and the phenylthiazole PIK-93 (FIG. 2).

Based on these co-crystal structures and a conserved arylmorpholine pharmacophore model, structural models were generated for three additional chemotypes bound to p110γ: the pyridinylfuranopyrimidine PI-103, the morpholinochromone PIK-108, and the morpholinopyranone KU-55933 (FIG. 2). Model-building for these inhibitors was guided by the observation that each compound contains the key arylmorpholine pharmacophore found in LY294002.

PIK-39 is an isoquinoline purine that inhibits p110δ at mid-nanomolar concentrations, p110γ and p110β at concentrations~100-fold higher, and shows no activity against any other PI3-K family member, including p110α, at concentrations up to 100 μM (FIG. 5). The biochemical selectivity of this compound is achieved through an unusual binding mode revealed in its co-crystal structure with p110γ (FIG. 2C). Only the mercaptopurine moiety of PIK-39 makes contacts within the interior of the ATP binding pocket, and this ring system is rotated ~110° and twisted ~35° out of the plane relative to the adenine of the ATP. In this orientation, it satisfies hydrogen bonds to the backbone amides of Val 882 and Glu 880 (thereby recapitulating the hydrogen bonds made by N1 and N6 of adenine).

In contrast to other PI3-K inhibitor structures, PIK-39 does not access the deeper pocket in the active site interior (FIG. 2C, lightly shaded area labeled as "Affinity Pocket"). Instead, the aryl-isoquinoline moiety of PIK-39 extends out to the entrance of the ATP binding pocket (FIG. 2B). In this region, the kinase accommodates the inhibitor by undergoing a conformational rearrangement in which Met 804 shifts from an "up" position, in which it forms the ceiling of the ATP binding pocket, to a "down" position which it packs against the isoquinoline moiety. The effect of this movement, which is unique to the PIK-39 structure (FIG. 2B), is to create a novel hydrophobic pocket between Met 804 and Trp 812 at the entrance to the ATP binding site. This induced-fit pocket buries ~180 Å2 of solvent accessible inhibitor surface area, enabling PIK-39 to achieve nanomolar affinity despite limited contacts within the active site core.

Co-crystal structures of PIK-90 and PIK-93 compounds bound to p110γ were determined. PIK-90 and PIK-93 both make a hydrogen bond to the backbone amide nitrogen of Val 882 (FIG. 2D), an interaction conserved among all known PI3-K inhibitors (Walker et al., 2000). In addition to this hydrogen bond, PIK-93 makes a second hydrogen bond to the backbone carbonyl of Val 882 and a third between its sulphonamide moiety and the side chain of Asp 964. PIK-93 is one of the most polar inhibitors in our panel (clogP=1.69) and these extended polar interactions may compensate for its limited hydrophobic surface area.

Figure 4:
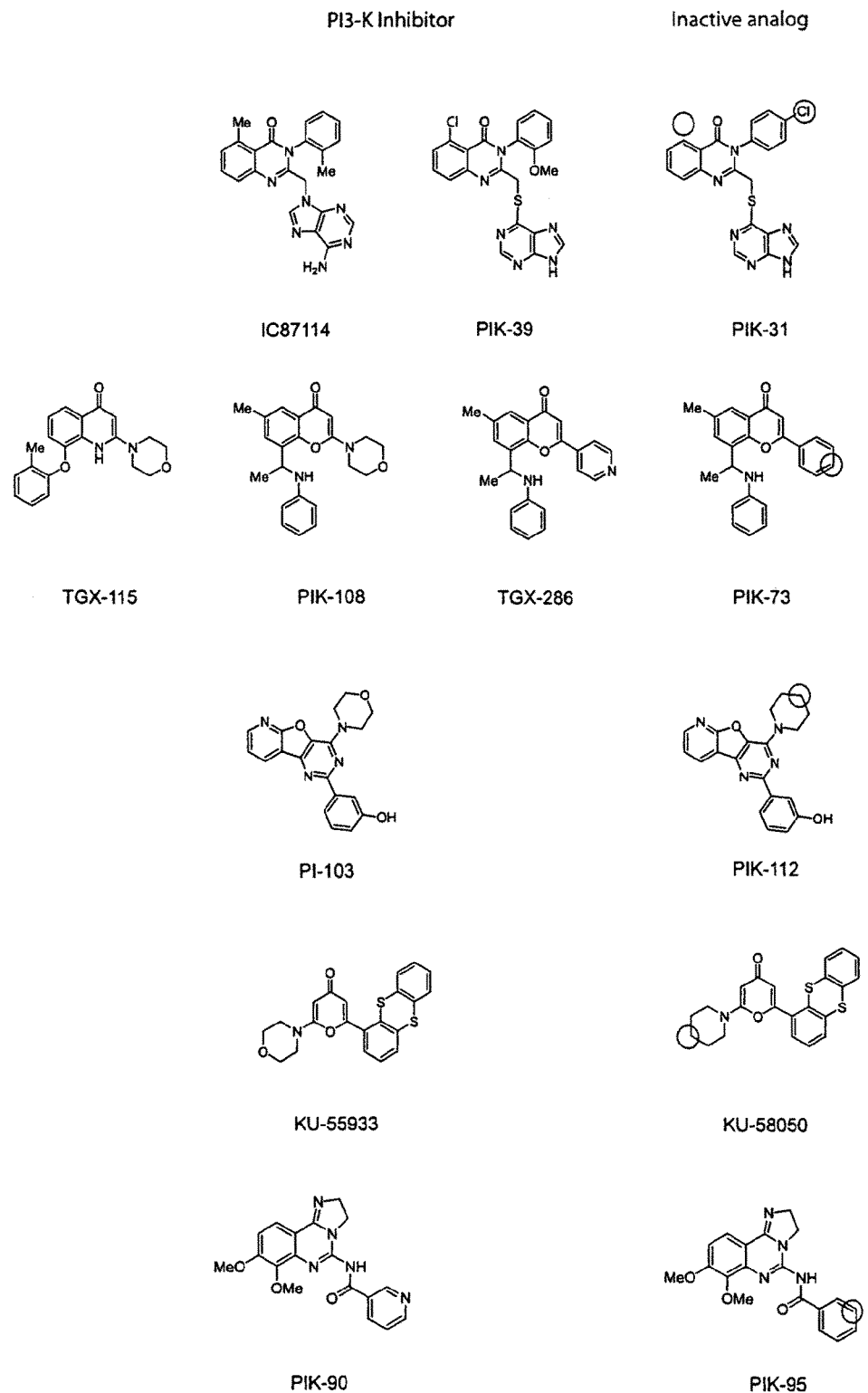
FIG. 4. Structures of additional PI3-K inhibitors and inactive analogs.

PIK-90 binds in a mode similar to PIK-93, although this larger compound makes more extensive hydrophobic interactions, burying 327 Å$^2$ of solvent accessible surface area. To achieve this, PIK-90 projects its pyridine ring into a deeper cavity that is partially accessed by PIK-93 but not occupied by ATP (FIG. 2D, lightly shaded circle). In this region, the pyridine ring of PIK-90 is poised to make a hydrogen bond to Lys 833, and we find that replacement of this pyridine nitrogen with carbon results in a 100-fold loss in affinity (PIK-95, FIG. 4). PI-103, a third multi-targeted PI3K inhibitor, projects a phenol into the same pocket based on an arylmorpholine pharmacophore model (FIG. 2D).

Two structural features distinguish these potent, multi-targeted inhibitors from the more selective compounds in our panel. First, these compounds adopt a flat conformation in the ATP binding pocket, whereas highly selective inhibitors project out of the plane occupied by ATP (FIG. 2). Second, the most potent inhibitors project into a deeper binding pocket that is not accessed by ATP (FIG. 2A). Much of the surface of this affinity pocket is contributed by the side-chain of Ile 879.

The mercaptopurine in the PIK-39 structure was replaced with adenine to yield a model of IC87114 (FIG. 3A). This substitution provided the adenine of IC87114 in the correct orientation to make the same hydrogen bonds as the mercaptopurine of PIK-39, even though these two ring systems are rotated by 110° with respect to each other.

Unlike other inhibitor chemotypes, PIK-39 does not exploit the PI3-kinase affinity pocket (FIG. 2C). The pyrazolopyrimidine analog of IC87114 (PIK-293) as well as a novel analog containing an m-phenol (PIK-294, FIG. 3A) were then tested for inhibition of the class I PI3-Ks. PIK-294 was up to 60-fold more potent than PIK-293 (FIG. 3A).

Figure 3B:
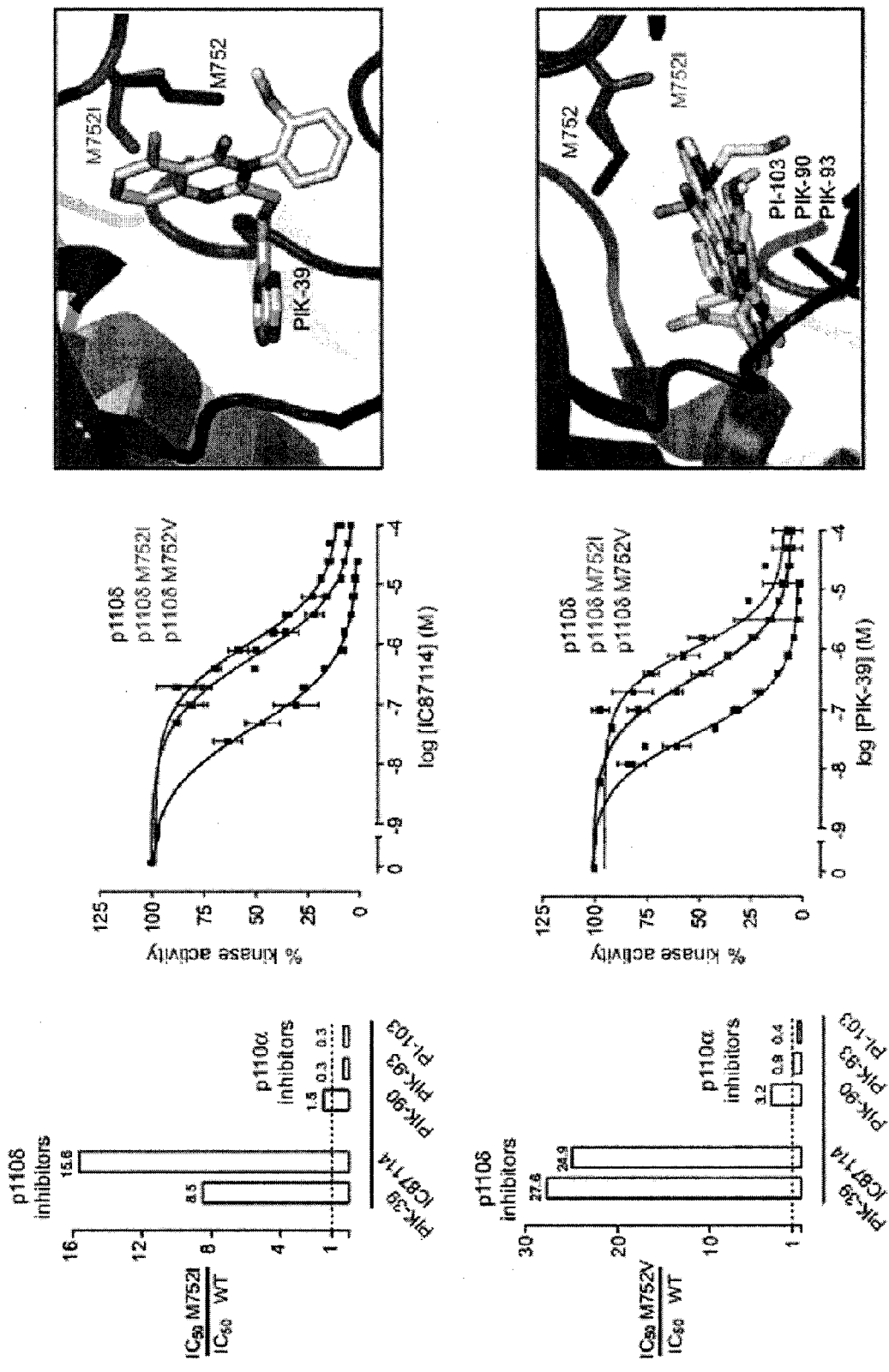

The structure of PIK-39 bound to p110γ reveals a conformational rearrangement of Met 804 that creates an induced pocket, and we have hypothesized that this conformational rearrangement underlies the selectivity of PIK-39 for p110δ. A prediction of this model is that mutation of Met 804 should perturb the binding of p110δ-selective inhibitors (which access the induced pocket), but not affect other classes of inhibitors (which do not access this pocket). Modeling suggests that mutation of Met 804 to a β-branched amino acid (such as valine or isoleucine) should restrict the pocket formed by rearrangement of that residue (FIG. 3B, right). Therefore, we mutated the corresponding residue in p110δ (Met 752) to valine or isoleucine, expressed and purified these kinases, and tested them for sensitivity to PI3-K inhibitors (FIG. 3B). We find that M7521 and M752V p110δ are resistant to the p110δ-selective inhibitors PIK-39 and IC87114, but retain sensitivity to the p110α/multi-targeted inhibitors PIK-90, PIK-93, and PI-103. This chemotype-specific resistance supports the unique role of Met 752 in gating an inducible selectivity pocket.

Antagonist modeling was performed using the PyMOL Molecular Graphics System. All p110γ crystal structures (PDB codes in parentheses), including the Apo (1E8Y), ATP (1E8X), Wortmannin (1E7U), LY294002 (1E7V), Quercetin (1E8W), Myricetin (1E90), and Staurosporine (1E8Z), PIK-90, PIK-93, and PIK-39 bound forms were structurally aligned using PyMOL's align function. Models for the inhibitors PIK-108, KU-55933, and PI-103 were built on top of the LY294002 arylmorpholine scaffold (IE7V) using PyMOL's fragment building function. A model for the inhibitor IC87114 was similarly built on top of the PIK-39 aryl-isoquinoline scaffold.

The model for PI-103 was built into the protein structure of p110γ bound to PIK-90, because the PIK-90 structure contains the enlarged affinity pocket that is necessary to accommodate PIK-103's phenolic moiety (the PIK-90 p110γ structure otherwise does not exhibit any conformational differences in the arymorpholine-binding region in comparison to the LY294002-bound p110γ structure). The models for PIK-108, KU-55933, and IC87114 were built into the protein structure of p110γ bound to PIK-39 because these inhibitors possess bulky groups that project out of the adenine plane and are likely to exploit the unique "Met 804 down" induced-fit pocket. In all inhibitor models, the choice of protein structure and inhibitor binding mode is based on extensive biochemical SAR as well as inhibitor geometry. The protein structures and inhibitor models have not been minimized to optimize binding energy, but care was taken to prevent any gross steric clashes and to satisfy key hydrogen bonds.

C. p110α/p85α, p110β/p85α, p110δ/p85α, and p110γ Assay

The class I PI3-Ks were either purchased (p110α/p85α, p110β/p85α, p110δ/p85α from Upstate, and p110γ from Sigma) or expressed as previously described (Knight et al., 2004). IC50 values were measured using either a standard TLC assay for lipid kinase activity (described below) or a high-throughput membrane capture assay. Kinase reactions were performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions were initiated by the addition of ATP containing 10 μCi of γ-32P-ATP to a final concentration 10 or 100 μM, as indicated in FIG. 5, and allowed to proceed for 5 minutes at room temperature. For TLC analysis, reactions were then terminated by the addition of 105 μl 1 N HCl followed by 160 μl CHCl3:MeOH (1:1). The biphasic mixture was vortexed, briefly centrifuged, and the organic phase transferred to a new tube using a gel loading pipette tip precoated with CHCl$_3$. This extract was spotted on TLC plates and developed for 3-4 hours in a 65:35 solution of n-propanol:1M acetic acid. The TLC plates were then dried, exposed to a phosphorimager screen (Storm, Amersham), and quantitated. For each compound, kinase activity was measured at 10-12 inhibitor concentrations representing two-fold dilutions from the highest concentration tested (typically, 200 μM). For compounds showing significant activity, IC50 determinations were repeated two to four times, and the reported value is the average of these independent measurements.

Results are set forth below in Table 2.

D. Abl Assay

Inhibitors (final concentration: 10 μM) were assayed in triplicate against recombinant full-length Abl or Abl (T3151) (Upstate) in an assay containing 25 mM HEPES, pH 7.4, 10 mM MgCl2, 200 μM ATP (2.5 μCi of γ-32P-ATP), and 0.5 mg/mL BSA. The optimized Abl peptide substrate EAIYAAPFAKKK (SEQ ID NO:1) was used as phosphoacceptor (200 μM). Reactions were terminated by spotting onto phosphocellulose sheets, which were washed with 0.5% phosphoric acid (approximately 6 times, 5-10 minutes each). Sheets were dried and the transferred radioactivity quantitated by phosphorimaging.

Results are set forth below in Table 3.

E. Hck Assay

Hck: Inhibitors (final concentration: 10 μM) were assayed in triplicate against recombinant full-length Hck in an assay containing 25 mM HEPES, pH 7.4, 10 mM MgCl2, 200 μM ATP (2.5 μCi of γ-32P-ATP), and 0.5 mg/mL BSA. The optimized Src family kinase peptide substrate EIYGEFKKK (SEQ ID NO:2) was used as phosphoacceptor (200 μM). Reactions were terminated by spotting onto phosphocellulose sheets, which were washed with 0.5% phosphoric acid (approximately 6 times, 5-10 minutes each). Sheets were dried and the transferred radioactivity quantitated by phosphorimaging.

Results are set forth below in Table 3.

F. Insulin Receptor (IR) Assay

Inhibitors (final concentration: 10 μM) were assayed in triplicate against recombinant insulin receptor kinase domain (Upstate) in an assay containing 25 mM HEPES, pH 7.4, 10 mM MgCl2, 10 mM MnCl2, 200 μM ATP (2.5 μCi of γ-32P-ATP), and 0.5 mg/mL BSA. Poly E-Y (Sigma; 2 mg/mL) was used as a substrate. Reactions were terminated by spotting onto nitrocellulose, which was washed with 1M NaCl/1% phosphoric acid (approximately 6 times, 5-10 minutes each). Sheets were dried and the transferred radioactivity quantitated by phosphorimaging.

Results are set forth below in Table 4.

G. Src Assay

Src, Src (T338I): Inhibitors (final concentration: 10 μM) were assayed in triplicate against recombinant full-length Src or Src (T338I) in an assay containing 25 mM HEPES, pH 7.4, 10 mM MgCl2, 200 μM ATP (2.5 μCi of γ-32P-ATP), and 0.5 mg/mL BSA. The optimized Src family kinase peptide substrate EIYGEFKKK (SEQ ID NO:2) was used as phosphoacceptor (200 μM). Reactions were terminated by spotting onto phosphocellulose sheets, which were washed with 0.5% phosphoric acid (approximately 6 times, 5-10 minutes each). Sheets were dried and the transferred radioactivity quantitated by phosphorimaging.

Results are set forth below in Table 3.

H. DNA-PK (DNAK) Assay

DNA-PK was purchased from Promega and assayed using the DNA-PK Assay System (Promega) according to the manufacturer's instructions.

Results are shown in Table 2.

I. mTOR Assay

Inhibitors (final concentrations 50 μM-0.003 μM) were tested against recombinant mTOR (Invitrogen) in an assay containing 50 mM HEPES, pH 7.5, 1 mM EGTA, 10 mM MgCl2, 2.5 mM, 0.01% Tween, 10 μM ATP (2.5 μCi of μ-32P-ATP), and 3 μg/mL BSA. Rat recombinant PHAS-1/4EBP1 (Calbiochem; 2 mg/mL) was used as a substrate. Reactions were terminated by spotting onto nitrocellulose, which was washed with 1M NaCl/1% phosphoric acid (approximately 6 times, 5-10 minutes each). Sheets were dried and the transferred radioactivity quantitated by phosphorimaging.

Results are set forth in Table 4 below.

J. Vascular Endothelial Growth Receptor

Vascular endothelial growth receptor 2(KDR): Inhibitors (final concentrations 50 μM-0.003 μM) were tested against recombinant KDR receptor kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) was used as a substrate. Reactions were terminated by spotting onto nitrocellulose, which was washed with 1M NaCl/1% phosphoric acid (approximately 6 times, 5-10 minutes each). Sheets were dried and the transferred radioactivity quantitated by phosphorimaging.

Results are set forth in Table 3 below.

K. Ephrin Receptor B4 (EphB4) Assay

Inhibitors (final concentrations 50 μM-0.003 μM) were tested against recombinant Ephrin receptor B4 kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) was used as a substrate. Reactions were terminated by spotting onto nitrocellulose, which was washed with 1M NaCl/1% phosphoric acid (approximately 6 times, 5-10 minutes each). Sheets were dried and the transferred radioactivity quantitated by phosphorimaging.

Results are set forth in Table 3 below.

L. Epidermal Growth Factor Receptor (EGFR) Assay

Inhibitors (final concentrations 50 μM-0.003 μM) were tested against recombinant EGF receptor kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) was used as a substrate. Reactions were terminated by spotting onto nitrocellulose, which was washed with 1M NaCl/1% phosphoric acid (approximately 6 times, 5-10 minutes each). Sheets were dried and the transferred radioactivity quantitated by phosphorimaging.

Results are set forth in Table 3 below.

M. KIT Assay

Inhibitors (final concentrations 50 μM-0.003 μM) were tested against recombinant KIT kinase domain (Invitrogen) in an assay containing 25 mM HEPES, pH 7.4, 10 mM MgCl2, 1 mM DTT, 10 mM MnCl2, 10 μM ATP (2.5 μCi of μ-32P-ATP), and 3 μg/mL BSA. Poly E-Y (Sigma; 2 mg/mL) was used as a substrate. Reactions were terminated by spotting onto nitrocellulose, which was washed with 1M NaCl/1% phosphoric acid (approximately 6 times, 5-10 minutes each). Sheets were dried and the transferred radioactivity quantitated by phosphorimaging.

Results are set forth in Table 4 below.

N. RET Assay

Inhibitors (final concentrations 50 μM-0.003 μM) were tested against recombinant RET kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAPFAKKK (SEQ ID NO:1) was used as phosphoacceptor (200 μM). Reactions were terminated by spotting onto phosphocellulose sheets, which were washed with 0.5% phosphoric acid (approximately 6 times, 5-10 minutes each). Sheets were dried and the transferred radioactivity quantitated by phosphorimaging.

Results are set forth in Table 4 below.

O. Platelet Derived Growth Factor Receptor (PDGFR) Assay

Inhibitors (final concentrations 50 μM-0.003 μM) were tested against recombinant PDG receptor kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAPFAKKK (SEQ ID NO:1) was used as phosphoacceptor (200 μM). Reactions were terminated by spotting onto phosphocellulose sheets, which were washed with 0.5% phosphoric acid (approximately 6 times, 5-10 minutes each). Sheets were dried and the transferred radioactivity quantitated by phosphorimaging.

Results are set forth in Table 4 below.

P. FMS-Related Tyrosine Kinase 3 (FLT-3) Assay

Inhibitors (final concentrations 50 μM-0.003 μM) were tested against recombinant FLT-3 kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAPFAKKK (SEQ ID NO:1) was used as phosphoacceptor (200 μM). Reactions were terminated by spotting onto phosphocellulose sheets, which were washed with 0.5% phosphoric acid (approximately 6 times, 5-10 minutes each). Sheets were dried and the transferred radioactivity quantitated by phosphorimaging.

Results are set forth in Table 4 below.

Q. TEK Receptor Tyrosine Kinase (TIE2) Assay

Inhibitors (final concentrations 50 μM-0.003 μM) were tested against recombinant TIE2 kinase domain (Invitrogen) in an assay containing 25 mM HEPES, pH 7.4, 10 mM MgCl2, 2 mM DTT, 10 mM MnCl2, 10 μM ATP (2.5 μCi of μ-32P-ATP), and 3 μg/mL BSA. Poly E-Y (Sigma; 2 mg/mL) was used as a substrate. Reactions were terminated by spotting onto nitrocellulose, which was washed with 1M NaCl/ 1% phosphoric acid (approximately 6 times, 5-10 minutes each). Sheets were dried and the transferred radioactivity quantitated by phosphorimaging.

Results are set forth in Table 4 below.

R. Results

In Table 1, the compounds have the formula:

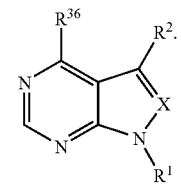

(I)

$R^1$ and $R^2$ are as defined in Table 1. X is =N- except where indicated. $R^{36}$ is —NH$_2$ except where indicated.

TABLE 1

| Cpd | $R^1$ | $R^2$ |
|---|---|---|
| KS167 | —H | phenyl |
| ZK141 | —H | 4-methylphenyl |
| KS84 | tert-butyl | 4-methylphenyl |
| ZK127 | —H | 3-methylphenyl |
| ZK134 | —H | 2-methylphenyl |
| ZK132 | —H | 2,3-dimethylphenyl |

TABLE 1-continued
| Cpd | R¹ | R² |
|---|---|---|
| ZK125 | —H | 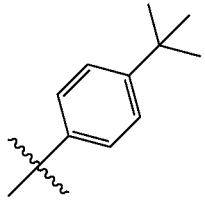 [SMILES: *c1ccc(C(C)(C)C)cc1] |
| BA46 | 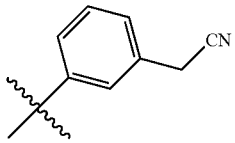 [SMILES: *c1cccc(CC#N)c1] | 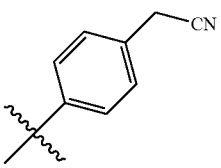 [SMILES: *c1ccc(CC#N)cc1] |
| BA45 |  |  |
| BA39 |  |  |
| BA150 |  | 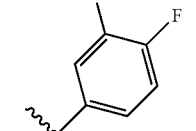 |
| BA151 |  | 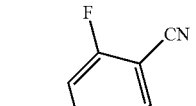 |
| BA21 |  | 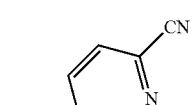 |
| BA52 |  | 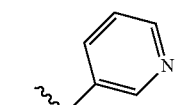 |

TABLE 1-continued

| Cpd | R¹ | R² |
|---|---|---|
| BA56 | isopropyl | 4-hydroxyphenyl |
| ZK138 | —H | 3-hydroxyphenyl |
| KS287 | isopropyl, X = CH | 3-hydroxyphenyl |
| KS288 | isopropyl, R³⁶ is N-Methyl | 3-hydroxyphenyl |
| KS284 | isopropyl | 3-hydroxyphenyl |
| BA60 | isopropyl | 4-hydroxy-3-methylphenyl |
| ZK318 | —H | 4-methyl-3-benzyloxyphenyl |
| ZK320 | —H | 4-methyl-3-hydroxyphenyl |
| ZK333 | -Me | 4-methyl-3-hydroxyphenyl |

TABLE 1-continued

| Cpd | R¹ | R² |
|---|---|---|
| ZK323 | isopropyl | 4-methyl-3-hydroxyphenyl |
| ZK327 | sec-butyl | 4-methyl-3-hydroxyphenyl |
| BA53 | isopropyl | pyrimidin-5-yl |
| BA31 | isopropyl | 4-acetylphenyl |
| BA152 | isopropyl | 3-fluoro-4-formylphenyl |
| BA149 | isopropyl | 3,5-difluoro-4-formylphenyl |
| BA32 | isopropyl | 3-chloro-4-carbamoylphenyl |
| BA55 | isopropyl | 3-acetylphenyl |

TABLE 1-continued

| Cpd | R¹ | R² |
|---|---|---|
| BA35 | isopropyl | furan-3-carbaldehyde (5-yl) |
| BA34 | isopropyl | 3-methyl-5-yl-thiophene-2-carbaldehyde |
| BA38 | isopropyl | 3-(methylsulfonamido)phenyl |
| BA40 | isopropyl | 4-(methylsulfonamido)phenyl |
| BA41 | isopropyl | 3-sulfamoylphenyl |
| BA77d | isopropyl | 2-fluoro-3-hydroxyphenyl |
| BA78d | cyclopentyl | 2-fluoro-3-hydroxyphenyl |
| BA22 | isopropyl | 3-fluoro-5-hydroxyphenyl |

TABLE 1-continued

| Cpd | R¹ | R² |
|---|---|---|
| BA79d | cyclopentyl | 3-fluoro-5-hydroxyphenyl |
| BA85 | isopropyl | 3-bromo-5-methoxyphenyl |
| BA87 | isopropyl | 3-bromo-5-hydroxyphenyl |
| ZK502 | isopropyl | 4-bromo-3-(methoxymethoxy)phenyl |
| ZK489 | -Me | 4-bromo-3-hydroxyphenyl |
| ZK487 | isopropyl | 4-bromo-3-hydroxyphenyl |
| Zk491 | cyclobutyl | 4-bromo-3-hydroxyphenyl |
| BA14 | isopropyl | 4-sulfamoylphenyl |

TABLE 1-continued

| Cpd | R¹ | R² |
|---|---|---|
| BA12 | (isopropyl-CH group) | —I |
| BA30 | (isopropyl-CH group) | 3-(thiazol-5-ylcarbamoyl)phenyl |
| ZK149 | —H | 4-([1,1'-biphenyl]-4-ylcarboxamido)phenyl |
| ZK126 | —H | 4-phenoxyphenyl |
| ZK143 | —H | 3-phenoxyphenyl |
| ZK150 | -Me<br>X═CH | 4-(benzyloxy)phenyl |
| ZK136 | —H | 3-(benzyloxy)phenyl |
| ZK131 | —H | 3-((2,6-dichlorobenzyl)oxy)phenyl |

TABLE 1-continued
| Cpd | R¹ | R² |
|---|---|---|
| ZK151 | -Me, X=CH | 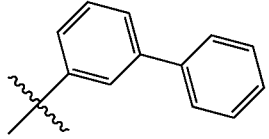 [SMILES: *c1cccc(-c2ccccc2)c1] |
| Zk493 | 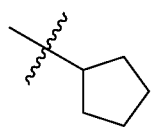 | 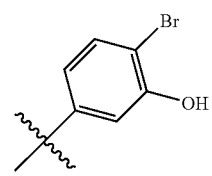 [SMILES: *c1ccc(Br)c(O)c1] |
| BA62d |  | 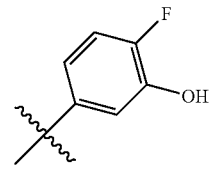 [SMILES: *c1ccc(F)c(O)c1] |
| ZK450 | 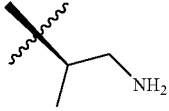 | 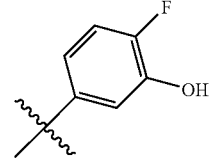 [SMILES: *c1ccc(F)c(O)c1] |
| ZK454 | 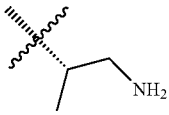 | 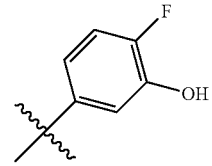 [SMILES: *c1ccc(F)c(O)c1] |
| ZK469 |  | 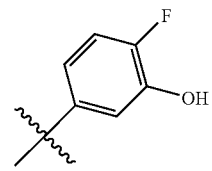 [SMILES: *c1ccc(F)c(O)c1] |
| ZK471 |  | 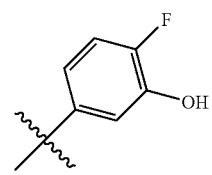 [SMILES: *c1ccc(F)c(O)c1] |
| ZK461 | 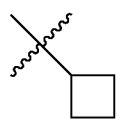 | 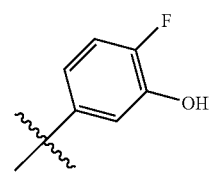 [SMILES: *c1ccc(F)c(O)c1] |

TABLE 1-continued
| Cpd | R¹ | R² |
|---|---|---|
| ZK413 | 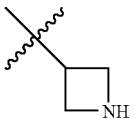 | 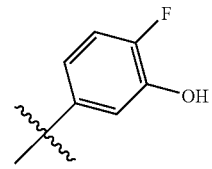 [SMILES: *c1ccc(F)c(O)c1] |
| ZK379 | 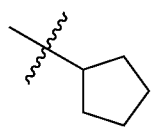 | 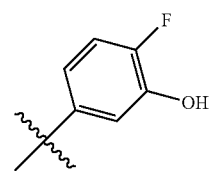 [SMILES: *c1ccc(F)c(O)c1] |
| ZK421 | 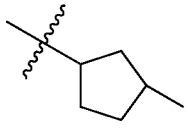 [SMILES: *C1CCC(C)C1] | 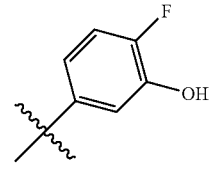 [SMILES: *c1ccc(F)c(O)c1] |
| ZK403 | 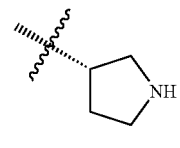 | 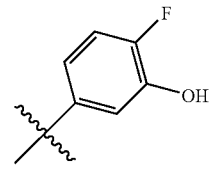 [SMILES: *c1ccc(F)c(O)c1] |
| ZK142 | —H | 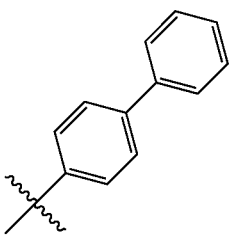 [SMILES: *c1ccc(-c2ccccc2)cc1] |
| ZK139 | —H | 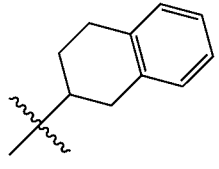 [SMILES: *C1CCc2ccccc2C1] |
| KS207 | —H | 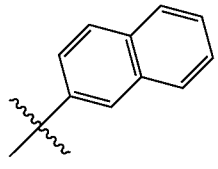 [SMILES: *c1ccc2ccccc2c1] |
| KS208 | -Me | 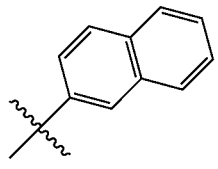 [SMILES: *c1ccc2ccccc2c1] |

TABLE 1-continued
| Cpd | R¹ | R² |
|---|---|---|
| ZK102 | -Me (R³⁶ is Cl) | 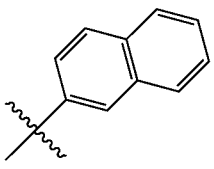 |
| ZK157 |  | 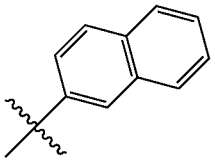 |
| ZK159 | 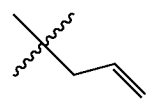 [SMILES: *CC=C] | 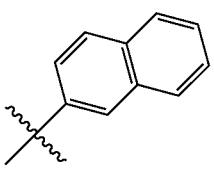 [SMILES: *c1ccc2ccccc2c1] |
| ZK156 |  | 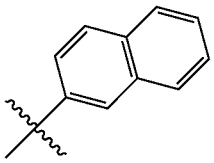 |
| KS63 | 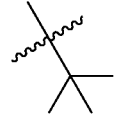 [SMILES: *C(C)(C)C] | 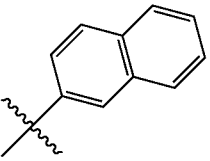 |
| ZK158 | 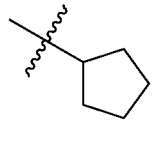 [SMILES: *C1CCCC1] | 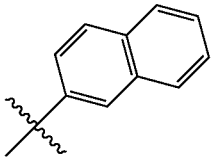 |
| ZK147 | 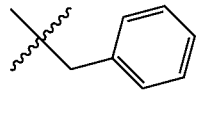 [SMILES: *Cc1ccccc1] | 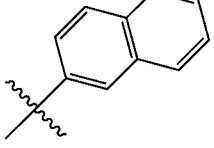 |
| ZK405 | 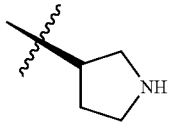 | 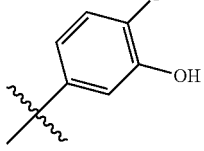 |
| ZK432 | 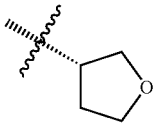 | 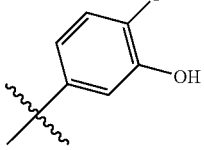 |

TABLE 1-continued

| Cpd | R¹ | R² |
|---|---|---|
| ZK434 | (S)-3-methyl-tetrahydrofuran-3-yl | 4-fluoro-3-hydroxyphenyl |
| ZK465 | 1-methyl-cycloheptyl | 4-fluoro-3-hydroxyphenyl |
| ZK377 | 2-(piperidin-4-yl)propan-2-yl | 4-fluoro-3-hydroxyphenyl |
| ZK399 | 2-(4-methyl-2-phenyl-2H-1,2,3-triazol-5-yl)propan-2-yl | 4-fluoro-3-hydroxyphenyl |
| ZK401 | 2-(4-phenyloxazol-5-yl)propan-2-yl | 4-fluoro-3-hydroxyphenyl |
| BA62 | 2,3-dimethylbutan-2-yl | 4-fluoro-3-methoxyphenyl |
| ZK358 | 2,3-dimethylbutan-2-yl | 4-chloro-3-hydroxyphenyl |
| ZK452 | (R)-1-amino-2-methylpropan-2-yl | 4-chloro-3-hydroxyphenyl |

TABLE 1-continued

| Cpd | R¹ | R² |
|---|---|---|
| ZK456 | (branched alkyl with NH₂) | 4-chloro-3-hydroxyphenyl |
| ZK463 | cyclobutyl-C(CH₃)₂- | 4-chloro-3-hydroxyphenyl |
| ZK155 | -CH₂CH₂-phenyl | 2-naphthyl |
| ZK162 | -CH₂C(O)NH₂ | 2-naphthyl |
| ZK165 | -CH₂-cyclopropyl | 2-naphthyl |
| ZK161 | -CH₂CH₂CH(CH₃)₂ | 2-naphthyl |
| ZK167 | -CH₂-CH=CH-phenyl | 2-naphthyl |
| ZK168 | -CH₂-C≡CH | 2-naphthyl |
| BA116 | -Me | 6-ethoxy-2-naphthyl |

TABLE 1-continued
| Cpd | R¹ | R² |
|---|---|---|
| BA17 | 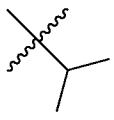 [SMILES: *C(C)C] | 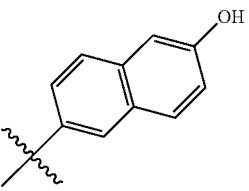 [SMILES: *c1ccc2cc(O)ccc2c1] |
| BA134 | 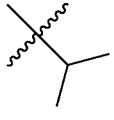 | 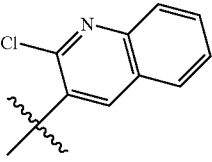 [SMILES: *c1cc2ccccc2nc1Cl] |
| BA105 | 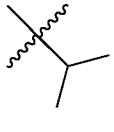 [SMILES: *C(C)C] | 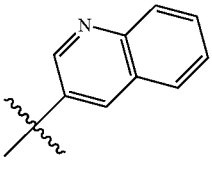 [SMILES: *c1cnc2ccccc2c1] |
| BA122 | 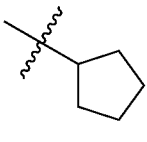 [SMILES: *C1CCCC1] | 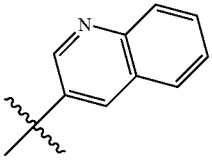 |
| BA111 | -Me | 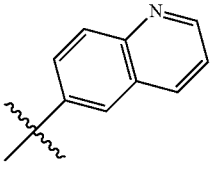 [SMILES: *c1ccc2ncccc2c1] |
| ZK371 | 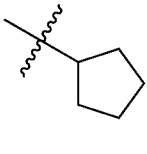 [SMILES: *C1CCCC1] | 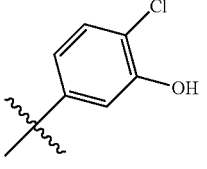 |
| ZK409 | 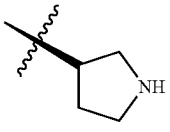 | 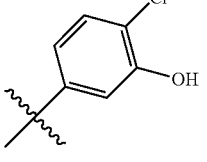 |
| ZK428 | 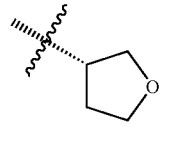 | 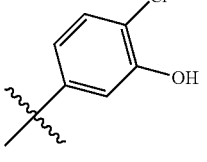 |

TABLE 1-continued
| Cpd | R¹ | R² |
|---|---|---|
| ZK430 | 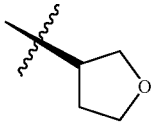 | 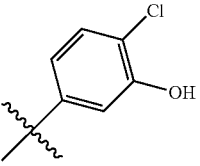 |
| ZK387 | 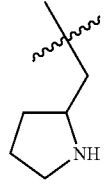 [SMILES: *CC1CCCN1] | 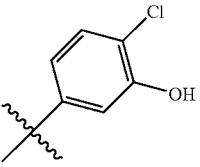 [SMILES: *c1ccc(Cl)c(O)c1] |
| ZK389 | 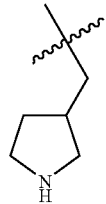 [SMILES: *CC1CCNC1] | 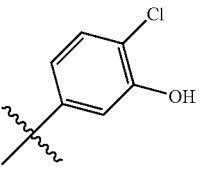 [SMILES: *c1ccc(Cl)c(O)c1] |
| ZK369 | 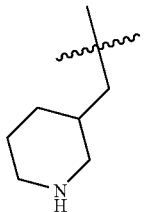 [SMILES: *CC1CCCNC1] | 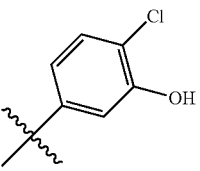 |
| ZK385 | 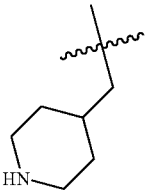 [SMILES: *CC1CCNCC1] | 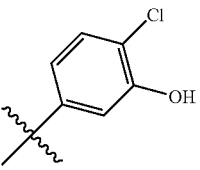 |
| ZK391 |  | 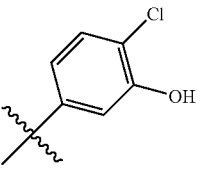 [SMILES: *c1ccc(Cl)c(O)c1] |
| BA102 | 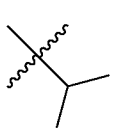 | 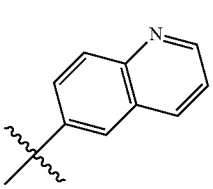 |

TABLE 1-continued

| Cpd | R¹ | R² |
|---|---|---|
| BA112 | cyclopentyl-methyl | quinolin-6-yl |
| BA118 | isopropyl-methyl | 2-methylquinolin-6-yl |
| BA130 | isopropyl-methyl | 2-chloroquinolin-6-yl |
| BA132 | isopropyl-methyl | quinoxalin-6-yl |
| BA139 | isopropyl-methyl | pyrido[2,3-b]pyrazin-7-yl |
| BA158 | isopropyl-methyl | 4-oxo-3,4-dihydroquinazolin-6-yl |
| BA140 | isopropyl-methyl | 2-oxo-1,2-dihydroquinolin-6-yl |
| BA141 | cyclopentyl-methyl | 2-oxo-1,2-dihydroquinolin-6-yl |

TABLE 1-continued

| Cpd | R¹ | R² |
|---|---|---|
| BA155_2 | isopropyl (wavy bond) | 4-chloro-3-hydroxyphenyl |
| BA157_2 | isopropyl (wavy bond) | 4-hydroxy-3-cyanophenyl |
| BA59 | isopropyl (wavy bond) | 4-hydroxy-3-fluorophenyl |
| BA63 | isopropyl (wavy bond) | 4-methoxy-2,5-difluorophenyl |
| BA93 | isopropyl (wavy bond) | 4-hydroxy-2,5-difluorophenyl |
| BA49 | isopropyl (wavy bond) | 3-methoxyphenyl |
| BA15 | isopropyl (wavy bond) | 4-hydroxy-3-methoxyphenyl |
| ZK321 | —H | 4-methoxy-3-hydroxyphenyl |
| ZK337 | -Me | 4-methoxy-3-hydroxyphenyl |

TABLE 1-continued

| Cpd | R¹ | R² |
|---|---|---|
| ZK347 | sec-butyl | 4-methoxy-3-hydroxyphenyl |
| BA146 | isopropyl-methyl (3-methylbut-2-yl) | 2-aminoquinolin-6-yl |
| BA142 | isopropyl-methyl (3-methylbut-2-yl) | 2-hydrazinylquinolin-6-yl (1H-tautomer) |
| BA145 | isopropyl-methyl (3-methylbut-2-yl) | 4-(Boc-amino)quinolin-6-yl |
| BA147 | isopropyl-methyl | 4-aminoquinolin-6-yl |
| BA148 | -Me | 4-oxo-4H-chromen-6-yl |
| BA143 | isopropyl-methyl (3-methylbut-2-yl) | 4-oxo-4H-chromen-6-yl |
| BA144 | cyclopentyl-methyl | 4-oxo-4H-chromen-6-yl |

TABLE 1-continued

| Cpd | R¹ | R² |
|---|---|---|
| BA129 | isopropyl | isoquinolin-6-yl |
| BA131 | isopropyl | isoquinolin-7-yl |
| BA133 | isopropyl | 2-methylquinolin-7-yl |
| ZK325 | isopropyl | 4-methoxy-3-hydroxyphenyl |
| ZK349 | cyclopentyl | 4-methoxy-3-hydroxyphenyl |
| ZK423 | 3-methylcyclopentyl | 4-methoxy-3-hydroxyphenyl |
| ZK411 | azetidin-3-yl | 4-methoxy-3-hydroxyphenyl |
| ZK407 | pyrrolidin-3-yl | 4-methoxy-3-hydroxyphenyl |

TABLE 1-continued

| Cpd | R¹ | R² |
|---|---|---|
| BA98 | cyclopentyl | 4-ethoxy-3-hydroxyphenyl |
| BA23 | isopropyl | 3,4-dimethoxyphenyl |
| ZK485 | tert-butyl | 3,4-dimethoxyphenyl |
| ZK495 | (S)-2-methyl-3-hydroxypropyl | 3,4-dimethoxyphenyl |
| ZK496 | (R)-2-methyl-3-hydroxypropyl | 3,4-dimethoxyphenyl |
| ZK494 | cyclobutyl | 3,4-dimethoxyphenyl |
| BA120 | -Me | 1H-pyrrolo[2,3-b]pyridin-5-yl |
| BA108 | isopropyl | 1H-pyrrolo[2,3-b]pyridin-5-yl |

TABLE 1-continued

| Cpd | R¹ | R² |
|---|---|---|
| BA121 | cyclopentyl-CH | 1H-pyrrolo[2,3-b]pyridin-5-yl |
| BA89 | isopropyl-CH | 1H-indol-5-yl |
| BA94 | cyclopentyl-CH | 1H-indol-5-yl |
| BA135 | isopropyl-CH | 1-methyl-1H-indol-5-yl |
| BA137 | isopropyl-CH | 1H-indazol-5-yl |
| BA138 | cyclopentyl-CH | 1H-indazol-5-yl |
| BA160 | isopropyl-CH | 3-amino-1H-indazol-5-yl |
| BA157_3 | isopropyl-CH | 3-aminobenzo[d]isoxazol-5-yl |

TABLE 1-continued

| Cpd | R¹ | R² |
|---|---|---|
| BA154 | isopropyl | 3-amino-1H-indazol-6-yl |
| BA90 | cyclopentyl | 3,4-dimethoxyphenyl |
| ZK341 | —H | 4-ethoxy-3-methoxyphenyl |
| ZK343 | isopropyl | 4-ethoxy-3-methoxyphenyl |
| ZK361 | allyl | 4-ethoxy-3-methoxyphenyl |
| ZK359 | cyclopentyl | 4-ethoxy-3-methoxyphenyl |
| ZK362 | cyclohexyl | 4-ethoxy-3-methoxyphenyl |
| BA64 | isopropyl | 3,4,5-trimethoxyphenyl |

TABLE 1-continued

| Cpd | R¹ | R² |
|---|---|---|
| BA65 | isopropyl | 2,3-dimethoxyphenyl (OMe, OMe) |
| ZK305 | isopropyl | 4-methoxy-3-ethoxyphenyl (OMe, OEt) |
| ZK306 | 2-methyl-2-(hydroxymethyl) / CH₂CH₂OH branched | 4-methoxy-3-ethoxyphenyl (OMe, OEt) |
| BA66 | isopropyl | 2,4-dimethoxypyrimidin-5-yl (OMe, OMe) |
| BA110 | isopropyl | 1H-indazol-6-yl |
| BA115 | cyclopentyl | 1H-indazol-6-yl |
| BA159 | isopropyl | 4-fluoro-1H-indazol-6-yl |
| BA119 | -Me | 1H-indol-6-yl |
| BA107 | isopropyl | 1H-indol-6-yl |

TABLE 1-continued

| Cpd | R¹ | R² |
|---|---|---|
| BA124 | cyclopentyl | 6-indolyl (1H-indol-6-yl) |
| BA161 | isopropyl | imidazo[1,2-a]pyridin-7-yl |
| BA162 | cyclopentyl | imidazo[1,2-a]pyridin-7-yl |
| BA24dd | isopropyl | 5-hydroxy-1H-indol-2-yl |
| BA43 | isopropyl | 3-formyl-1H-indol-6-yl |
| BA91 | isopropyl | 1H-indol-4-yl |
| BA48 | isopropyl | 4-methoxyphenyl |
| ZK133 | —H | 2-hydroxyphenyl |

TABLE 1-continued

| Cpd | R¹ | R² |
|---|---|---|
| BA20dd | isopropyl | 4-amino-3-hydroxyphenyl |
| BA20d | isopropyl | 4-amino-3-methoxyphenyl |
| BA20 | isopropyl | 4-(Boc-amino)-3-methoxyphenyl |
| BA99 | isopropyl | 4-[(1-hydroxypropan-2-yl)amino]-3-methoxyphenyl |
| BA81dd | cyclopentyl | 4-amino-3-hydroxyphenyl |
| BA81d | cyclopentyl | 4-amino-3-methoxyphenyl |
| ZK137 | —H | 4-aminophenyl |
| ZK135 | —H | 3-aminophenyl |

TABLE 1-continued
| Cpd | R¹ | R² |
|---|---|---|
| ZK130 | —H | 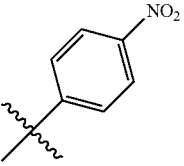 [SMILES: *c1ccc([N+](=O)[O-])cc1] |
| BA92 | 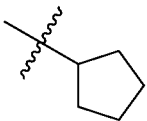 [SMILES: *C1CCCC1] | 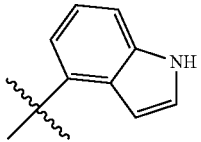 [SMILES: *c1cccc2[nH]ccc12] |
| BA86 | 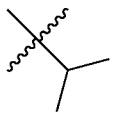 | 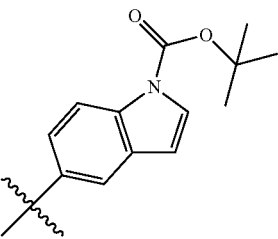 [SMILES: *c1ccc2c(ccn2C(=O)OC(C)(C)C)c1] |
| BA88 | 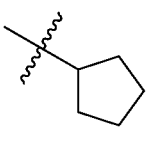 [SMILES: *C1CCCC1] | 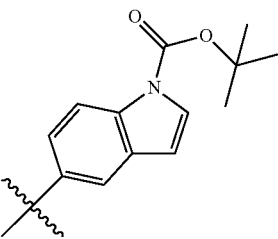 [SMILES: *c1ccc2c(ccn2C(=O)OC(C)(C)C)c1] |
| BA96 | 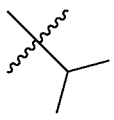 | 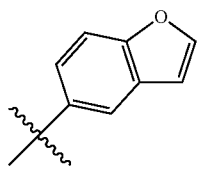 [SMILES: *c1ccc2occc2c1] |
| BA97 | 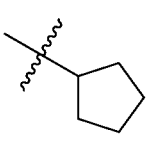 [SMILES: *C1CCCC1] | 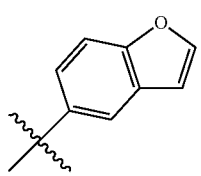 [SMILES: *c1ccc2occc2c1] |
| BA44 | 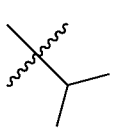 [SMILES: *C(C)C] | 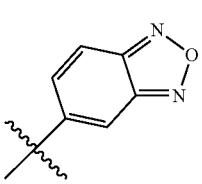 [SMILES: *c1ccc2nonc2c1] |
| BA156 | 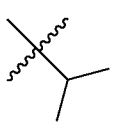 [SMILES: *C(C)C] | 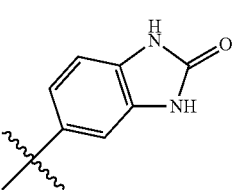 [SMILES: *c1ccc2[nH]c(=O)[nH]c2c1] |

TABLE 1-continued

| Cpd | R¹ | R² |
|---|---|---|
| BA95 | isopropyl | 2,3-dihydrobenzofuran-5-yl |
| ZK129 | -Me, X=CH | benzo[1,3]dioxol-5-yl |
| BA54 | isopropyl | 2,3-dihydro-1,4-benzodioxin-6-yl |
| ZK152 | -Me, X=CH | benzo[b]thiophen-2-yl |
| ZK128 | —H | 3-nitrophenyl |
| BA26 | sec-butyl | 3-(hydroxymethyl)phenyl |
| BA42 | sec-butyl | 5-formylbenzo[b]thiophen-2-yl |

TABLE 2

| Cpd | 110 | 110 | 110 | 110 | DPK | Cpd | 110 | 110 | 110 | 110 | DPK |
|---|---|---|---|---|---|---|---|---|---|---|---|
| KS167 | ++ | + | ++ | ++ | ++ | BA46 | ++ | ++ | +++ | ++ | +++ |
| ZK141 | ++ | ++ | ++ | ++ | +++ | BA45 | ++ | + | ++ | ++ | ++ |
| KS84 | ++ | + | ++ | + | +++ | BA39 | ++ | | +++ | ++ | ++ |
| ZK127 | ++ | ++ | ++ | ++ | +++ | BA150 | ++ | + | ++ | ++ | ++ |
| ZK134 | ++ | + | ++ | ++ | +++ | BA151 | ++ | + | ++ | ++ | ++ |
| ZK132 | ++ | ++ | ++ | ++ | +++ | BA21 | ++ | ++ | ++ | | ++ |
| ZK125 | ++ | + | ++ | ++ | +++ | BA52 | ++ | | ++ | ++ | ++ |
| BA56 | +++ | +++ | +++ | +++ | +++ | BA53 | ++ | + | + | + | ++ |
| ZK138 | ++ | ++ | ++ | ++ | +++ | BA31 | ++ | ++ | +++ | +++ | ++ |
| KS287 | ++ | ++ | ++ | ++ | ++ | BA152 | ++ | ++ | +++ | ++ | +++ |
| KS288 | | + | + | + | +++ | BA149 | ++ | ++ | ++ | ++ | + |

TABLE 2-continued

| Cpd | 110 | 110 | 110 | 110 | DPK | Cpd | 110 | 110 | 110 | 110 | DPK |
|---|---|---|---|---|---|---|---|---|---|---|---|
| KS284 | +++ | ++ | +++ | ++ | +++ | BA32 | ++ | ++ | +++ | | +++ |
| BA60 | ++ | ++ | +++ | ++ | +++ | BA55 | ++ | ++ | +++ | ++ | ++ |
| ZK318 | ++ | + | ++ | ++ | ++ | BA35 | ++ | | +++ | +++ | +++ |
| ZK320 | ++ | ++ | +++ | +++ | ++ | BA34 | ++ | ++ | +++ | ++ | +++ |
| ZK333 | +++ | ++ | +++ | +++ | +++ | BA38 | ++ | | +++ | +++ | +++ |
| ZK323 | +++ | ++ | +++ | +++ | +++ | BA40 | ++ | | ++ | ++ | +++ |
| ZK327 | +++ | ++ | +++ | +++ | +++ | BA41 | ++ | ++ | +++ | +++ | +++ |
| BA77d | ++ | ++ | +++ | ++ | ++ | BA14 | ++ | ++ | +++ | ++ | +++ |
| BA78d | ++ | ++ | +++ | ++ | +++ | BA12 | ++ | ++ | +++ | ++ | ++ |
| BA22 | +++ | +++ | +++ | +++ | +++ | BA30 | ++ | ++ | +++ | +++ | +++ |
| BA79d | +++ | ++ | +++ | ++ | +++ | ZK149 | + | ++ | ++ | ++ | + |
| BA85 | ++ | ++ | ++ | ++ | +++ | ZK126 | ++ | + | ++ | + | ++ |
| BA87 | +++ | +++ | +++ | +++ | +++ | ZK143 | + | + | + | + | + |
| ZK502 | ++ | ++ | +++ | ++ | +++ | ZK150 | ++ | + | + | + | ++ |
| ZK489 | +++ | +++ | +++ | +++ | +++ | ZK136 | ++ | + | + | ++ | +++ |
| ZK487 | +++ | +++ | +++ | +++ | +++ | ZK131 | + | + | + | + | + |
| Zk491 | +++ | +++ | +++ | +++ | ++ | ZK151 | + | + | + | + | +++ |
| Zk493 | +++ | +++ | +++ | +++ | +++ | ZK142 | + | + | + | + | + |
| BA62d | +++ | +++ | +++ | ++ | +++ | ZK139 | + | + | + | ++ | ++ |
| ZK450 | ++ | ++ | ++ | +++ | + | KS207 | ++ | + | +++ | +++ | +++ |
| ZK454 | ++ | ++ | ++ | +++ | +++ | KS208 | ++ | ++ | ++ | +++ | +++ |
| ZK469 | +++ | +++ | ++ | +++ | +++ | ZK102 | + | + | + | + | +++ |
| ZK471 | +++ | +++ | +++ | +++ | ++ | ZK157 | | | +++ | | +++ |
| ZK461 | +++ | ++ | +++ | ++ | ++ | ZK159 | ++ | ++ | ++ | ++ | +++ |
| ZK413 | ++ | +++ | +++ | +++ | +++ | ZK156 | ++ | ++ | ++ | ++ | +++ |
| ZK379 | +++ | ++ | +++ | +++ | +++ | KS63 | + | + | + | + | +++ |
| ZK421 | +++ | ++ | +++ | ++ | +++ | ZK158 | ++ | ++ | ++ | ++ | +++ |
| ZK403 | ++ | +++ | +++ | +++ | ++ | ZK147 | + | ++ | ++ | ++ | ++ |
| ZK405 | ++ | ++ | +++ | ++ | +++ | ZK155 | ++ | ++ | ++ | ++ | +++ |
| ZK432 | +++ | ++ | +++ | +++ | +++ | ZK162 | ++ | + | ++ | ++ | +++ |
| ZK434 | +++ | +++ | +++ | +++ | +++ | ZK165 | ++ | + | ++ | ++ | +++ |
| ZK465 | +++ | + | +++ | +++ | +++ | ZK161 | ++ | + | ++ | ++ | ++ |
| ZK377 | ++ | ++ | ++ | ++ | +++ | ZK167 | | | ++ | | ++ |
| ZK399 | ++ | ++ | +++ | ++ | +++ | ZK168 | | | ++ | | +++ |
| ZK401 | ++ | + | ++ | + | +++ | BA116 | + | ++ | ++ | ++ | +++ |
| BA62 | +++ | ++ | +++ | +++ | +++ | BA17 | +++ | ++ | +++ | +++ | +++ |
| ZK358 | +++ | ++ | +++ | +++ | +++ | BA134 | ++ | + | ++ | + | ++ |
| ZK452 | ++ | ++ | ++ | +++ | +++ | BA105 | ++ | ++ | +++ | ++ | +++ |
| ZK456 | +++ | ++ | ++ | +++ | +++ | BA122 | ++ | ++ | +++ | ++ | +++ |
| ZK463 | +++ | ++ | +++ | +++ | +++ | BA111 | +++ | +++ | +++ | +++ | +++ |
| ZK371 | +++ | +++ | +++ | +++ | +++ | BA102 | +++ | +++ | +++ | +++ | +++ |
| ZK409 | +++ | +++ | +++ | +++ | +++ | BA112 | +++ | ++ | +++ | +++ | +++ |
| ZK428 | +++ | +++ | +++ | +++ | +++ | BA118 | +++ | ++ | +++ | +++ | +++ |
| ZK430 | +++ | ++ | +++ | +++ | +++ | BA130 | ++ | ++ | +++ | ++ | +++ |
| ZK387 | ++ | ++ | ++ | ++ | +++ | BA132 | +++ | +++ | +++ | +++ | +++ |
| ZK389 | ++ | +++ | +++ | ++ | +++ | BA139 | ++ | ++ | +++ | + | ++ |
| ZK369 | ++ | + | ++ | ++ | ++ | BA158 | +++ | +++ | +++ | +++ | +++ |
| ZK385 | ++ | ++ | +++ | ++ | +++ | BA140 | + | ++ | + | + | ++ |
| ZK391 | ++ | ++ | +++ | ++ | +++ | BA141 | + | + | + | + | + |
| BA155_2 | +++ | +++ | +++ | +++ | +++ | BA146 | +++ | +++ | +++ | +++ | +++ |
| BA157_2 | +++ | +++ | +++ | +++ | +++ | BA142 | +++ | ++ | ++ | +++ | +++ |
| BA59 | +++ | +++ | +++ | +++ | +++ | BA145 | ++ | ++ | ++ | ++ | ++ |
| BA63 | | ++ | +++ | +++ | +++ | BA147 | ++ | ++ | ++ | ++ | ++ |
| BA93 | +++ | ++ | +++ | +++ | +++ | BA148 | ++ | ++ | ++ | ++ | +++ |
| BA49 | ++ | + | ++ | ++ | ++ | BA143 | ++ | ++ | ++ | ++ | +++ |
| BA15 | +++ | ++ | +++ | +++ | +++ | BA144 | +++ | ++ | +++ | +++ | +++ |
| ZK321 | +++ | ++ | +++ | +++ | +++ | BA129 | ++ | + | ++ | + | ++ |
| ZK337 | +++ | +++ | +++ | +++ | +++ | BA131 | +++ | ++ | +++ | +++ | +++ |
| ZK347 | +++ | +++ | +++ | +++ | +++ | BA133 | +++ | +++ | +++ | +++ | +++ |
| ZK325 | +++ | +++ | +++ | +++ | +++ | BA120 | +++ | ++ | +++ | +++ | +++ |
| ZK349 | +++ | +++ | +++ | +++ | +++ | BA108 | ++ | ++ | +++ | ++ | +++ |
| ZK423 | +++ | +++ | +++ | +++ | +++ | BA121 | +++ | ++ | +++ | ++ | +++ |
| ZK411 | ++ | +++ | +++ | +++ | +++ | BA89 | +++ | ++ | +++ | +++ | +++ |
| ZK407 | ++ | +++ | +++ | ++ | ++ | BA94 | +++ | ++ | +++ | +++ | +++ |
| BA98 | +++ | +++ | +++ | +++ | +++ | BA135 | +++ | ++ | +++ | +++ | +++ |
| S1 | ++ | + | ++ | + | + | BA136 | +++ | ++ | +++ | ++ | +++ |
| BA23 | +++ | +++ | +++ | +++ | +++ | BA137 | +++ | +++ | +++ | +++ | +++ |
| ZK485 | +++ | +++ | +++ | ++ | ++ | BA138 | +++ | ++ | +++ | +++ | +++ |
| ZK495 | ++ | ++ | +++ | ++ | +++ | BA160 | ++ | ++ | +++ | ++ | +++ |
| ZK496 | ++ | ++ | +++ | ++ | +++ | BA157_3 | +++ | ++ | +++ | +++ | +++ |
| ZK494 | +++ | +++ | +++ | +++ | +++ | BA154 | +++ | +++ | +++ | +++ | +++ |
| BA90 | +++ | +++ | +++ | +++ | +++ | BA110 | +++ | ++ | +++ | +++ | +++ |
| ZK341 | ++ | ++ | +++ | ++ | +++ | BA115 | +++ | ++ | +++ | +++ | +++ |
| ZK343 | +++ | ++ | +++ | ++ | +++ | BA159 | +++ | +++ | +++ | +++ | ++ |
| ZK361 | ++ | ++ | +++ | +++ | +++ | BA119 | ++ | ++ | +++ | ++ | +++ |
| ZK359 | +++ | +++ | +++ | +++ | +++ | BA107 | ++ | ++ | +++ | ++ | +++ |
| ZK362 | +++ | +++ | +++ | +++ | ++ | BA124 | ++ | ++ | +++ | ++ | +++ |
| BA64 | + | + | ++ | ++ | ++ | BA161 | + | + | + | + | +++ |

TABLE 2-continued

| Cpd | 110 | 110 | 110 | 110 | DPK | Cpd | 110 | 110 | 110 | 110 | DPK |
|---|---|---|---|---|---|---|---|---|---|---|---|
| BA65 | + | + | ++ | + | ++ | BA162 | ++ | ++ | ++ | ++ | +++ |
| ZK305 | +++ | +++ | +++ | +++ | +++ | BA24dd | ++ | ++ | +++ | ++ | +++ |
| ZK306 | ++ | + | ++ | ++ | ++ | BA43 | +++ | | +++ | +++ | +++ |
| BA66 | ++ | ++ | +++ | ++ | +++ | BA91 | ++ | ++ | +++ | ++ | +++ |
| BA48 | ++ | ++ | +++ | ++ | +++ | BA92 | ++ | ++ | +++ | ++ | +++ |
| ZK133 | + | + | + | ++ | ++ | BA86 | ++ | ++ | ++ | +++ | +++ |
| BA20dd | ++ | ++ | ++ | ++ | +++ | BA88 | + | + | ++ | +++ | +++ |
| BA20d | ++ | ++ | +++ | +++ | +++ | BA96 | ++ | + | +++ | +++ | +++ |
| BA20 | ++ | | ++ | ++ | ++ | BA97 | ++ | ++ | +++ | +++ | +++ |
| BA99 | ++ | + | ++ | + | ++ | BA44 | ++ | +++ | ++ | ++ | ++ |
| BA81dd | +++ | ++ | +++ | +++ | + | BA156 | ++ | ++ | ++ | ++ | +++ |
| BA81d | +++ | ++ | +++ | +++ | +++ | BA95 | ++ | ++ | +++ | +++ | +++ |
| ZK137 | ++ | + | ++ | ++ | +++ | ZK129 | ++ | ++ | ++ | ++ | +++ |
| ZK135 | ++ | + | + | ++ | ++ | BA54 | ++ | ++ | ++ | ++ | +++ |
| ZK130 | + | + | + | + | + | ZK152 | ++ | ++ | ++ | ++ | +++ |
| ZK128 | ++ | + | ++ | ++ | ++ | BA42 | ++ | ++ | ++ | ++ | +++ |
| BA26 | ++ | ++ | +++ | +++ | ++ | PIK294 | ++ | +++ | +++ | +++ | ++ |
| SU11248 | ++ | + | ++ | ++ | + | Iressa | + | + | + | + | + |
| BAY43-9006 | ++ | + | + | + | + | PIK103 | +++ | +++ | +++ | +++ | +++ |
| Dasatinib | ++ | + | ++ | ++ | ++ | PIK90 | +++ | +++ | +++ | +++ | +++ |

TABLE 3

| Cpd | Abl | Hck | Src | Src (T/I) | VEGFR | EGFR | EphB4 | Cpd | Abl | Hck | Src | Src (T/I) | VEGFR | EGFR | EphB4 |
|---|---|---|---|---|---|---|---|---|---|---|---|---|---|---|---|
| KS84 | +++ | +++ | +++ | ++ | +++ | +++ | +++ | ZK385 | ++ | +++ | +++ | + | ++ | + | ++ |
| BA56 | ++ | +++ | +++ | ++ | ++ | +++ | ++ | ZK391 | ++ | +++ | +++ | + | ++ | ++ | ++ |
| KS284 | +++ | +++ | +++ | ++ | +++ | +++ | +++ | BA155_2 | ++ | +++ | +++ | ++ | ++ | ++ | ++ |
| BA60 | ++ | +++ | +++ | +++ | ++ | + | ++ | BA157_2 | ++ | ++ | ++ | ++ | ++ | ++ | ++ |
| ZK318 | ++ | ++ | +++ | ++ | + | | ++ | BA59 | +++ | +++ | +++ | +++ | ++ | ++ | +++ |
| ZK320 | +++ | +++ | +++ | ++ | +++ | ++ | ++ | BA63 | ++ | +++ | +++ | ++ | ++ | ++ | ++ |
| ZK333 | +++ | +++ | +++ | ++ | +++ | ++ | ++ | BA93 | ++ | +++ | +++ | ++ | ++ | ++ | ++ |
| ZK323 | +++ | +++ | +++ | +++ | +++ | +++ | ++ | BA49 | ++ | +++ | +++ | ++ | + | ++ | +++ |
| ZK327 | +++ | +++ | +++ | ++ | +++ | ++ | ++ | BA15 | ++ | +++ | +++ | ++ | + | +++ | ++ |
| BA77d | +++ | +++ | +++ | ++ | ++ | ++ | +++ | ZK321 | +++ | +++ | +++ | ++ | ++ | + | ++ |
| BA78d | +++ | +++ | +++ | ++ | +++ | ++ | ++ | ZK337 | +++ | +++ | +++ | | | + | ++ |
| BA22 | +++ | +++ | +++ | ++ | +++ | +++ | +++ | ZK347 | +++ | +++ | +++ | ++ | +++ | ++ | ++ |
| BA79d | +++ | +++ | +++ | ++ | +++ | +++ | ++ | ZK325 | +++ | +++ | +++ | ++ | +++ | +++ | +++ |
| BA85 | ++ | +++ | +++ | ++ | ++ | ++ | ++ | ZK349 | +++ | +++ | +++ | +++ | +++ | +++ | +++ |
| BA87 | +++ | +++ | +++ | +++ | +++ | +++ | +++ | ZK423 | +++ | +++ | +++ | ++ | +++ | +++ | +++ |
| ZK502 | +++ | +++ | +++ | ++ | ++ | ++ | + | ZK411 | ++ | ++ | +++ | + | ++ | ++ | ++ |
| ZK489 | +++ | +++ | +++ | + | ++ | + | ++ | ZK407 | ++ | +++ | +++ | + | +++ | ++ | + |
| ZK487 | +++ | +++ | +++ | ++ | +++ | +++ | +++ | BA98 | +++ | +++ | +++ | ++ | +++ | +++ | ++ |
| Zk491 | +++ | +++ | +++ | ++ | +++ | +++ | +++ | S1 | +++ | + | ++ | + | + | + | + |
| Zk493 | +++ | +++ | +++ | ++ | +++ | +++ | +++ | BA23 | ++ | ++ | +++ | ++ | + | ++ | ++ |
| BA62d | +++ | +++ | +++ | +++ | +++ | ++ | +++ | ZK485 | ++ | +++ | +++ | + | + | ++ | ++ |
| ZK450 | +++ | +++ | +++ | + | ++ | + | ++ | ZK495 | ++ | ++ | ++ | ++ | ++ | ++ | ++ |
| ZK454 | +++ | ++ | +++ | + | ++ | ++ | + | ZK496 | ++ | ++ | ++ | ++ | ++ | ++ | ++ |
| ZK469 | +++ | +++ | +++ | + | ++ | ++ | ++ | ZK494 | +++ | +++ | +++ | ++ | ++ | ++ | ++ |
| ZK471 | +++ | +++ | +++ | + | ++ | ++ | + | BA90 | ++ | +++ | +++ | ++ | ++ | ++ | ++ |
| ZK461 | +++ | +++ | +++ | + | +++ | ++ | ++ | ZK341 | ++ | ++ | + | + | + | + | + |
| ZK413 | +++ | +++ | +++ | + | ++ | ++ | | ZK343 | ++ | +++ | +++ | + | ++ | ++ | ++ |
| ZK379 | +++ | +++ | +++ | ++ | +++ | +++ | +++ | ZK361 | ++ | ++ | ++ | + | + | ++ | + |
| ZK421 | +++ | +++ | +++ | +++ | +++ | +++ | +++ | ZK359 | +++ | +++ | +++ | ++ | ++ | ++ | +++ |
| ZK403 | +++ | +++ | +++ | ++ | +++ | ++ | +++ | ZK362 | ++ | +++ | +++ | + | + | ++ | + |
| ZK405 | +++ | +++ | +++ | ++ | ++ | ++ | + | BA64 | +++ | +++ | +++ | ++ | + | ++ | +++ |
| ZK432 | +++ | +++ | +++ | ++ | +++ | ++ | +++ | BA65 | ++ | +++ | +++ | ++ | ++ | ++ | ++ |
| ZK434 | +++ | +++ | +++ | ++ | +++ | ++ | +++ | ZK305 | ++ | ++ | ++ | ++ | + | ++ | ++ |
| ZK465 | +++ | +++ | +++ | + | +++ | +++ | +++ | ZK306 | + | ++ | ++ | ++ | ++ | + | + |
| ZK377 | ++ | ++ | +++ | + | ++ | + | + | BA66 | ++ | ++ | ++ | + | ++ | + | ++ |
| ZK399 | +++ | +++ | +++ | + | + | + | ++ | BA48 | ++ | +++ | +++ | ++ | ++ | ++ | ++ |
| ZK401 | +++ | +++ | +++ | + | + | + | + | BA20dd | +++ | +++ | +++ | ++ | ++ | ++ | ++ |
| BA62 | +++ | +++ | +++ | + | + | ++ | + | BA20d | +++ | +++ | +++ | ++ | ++ | ++ | ++ |
| ZK358 | +++ | +++ | +++ | ++ | +++ | +++ | +++ | BA20 | +++ | +++ | +++ | +++ | ++ | ++ | + |
| ZK452 | +++ | +++ | +++ | ++ | +++ | ++ | ++ | BA99 | ++ | +++ | +++ | ++ | +++ | ++ | ++ |
| ZK456 | +++ | +++ | +++ | + | ++ | ++ | ++ | BA81dd | +++ | +++ | +++ | ++ | +++ | +++ | +++ |
| ZK463 | +++ | +++ | +++ | ++ | +++ | ++ | ++ | BA81d | +++ | +++ | +++ | ++ | +++ | +++ | +++ |
| ZK371 | +++ | +++ | +++ | ++ | +++ | +++ | +++ | BA26 | ++ | ++ | +++ | + | + | + | + |
| ZK409 | +++ | +++ | +++ | ++ | +++ | +++ | +++ | BA46 | ++ | +++ | +++ | ++ | ++ | ++ | ++ |
| ZK428 | +++ | +++ | +++ | ++ | +++ | +++ | +++ | BA45 | ++ | +++ | +++ | ++ | ++ | ++ | + |
| ZK430 | +++ | +++ | +++ | ++ | +++ | +++ | +++ | BA39 | ++ | ++ | ++ | ++ | ++ | + | ++ |
| ZK387 | +++ | +++ | +++ | + | ++ | ++ | ++ | BA150 | ++ | ++ | ++ | + | ++ | + | ++ |
| ZK389 | +++ | +++ | +++ | ++ | ++ | ++ | +++ | BA151 | ++ | ++ | ++ | + | + | + | ++ |
| ZK369 | ++ | ++ | +++ | + | ++ | ++ | + | BA21 | ++ | ++ | ++ | + | + | + | + |

TABLE 3-continued

| Cpd | Abl | Hck | Src | Src (T/I) | VEGFR | EGFR | EphB4 |
|---|---|---|---|---|---|---|---|
| BA52 | ++ | ++ | ++ | + | + | + | + |
| BA53 | ++ | ++ | ++ | + | + | + | + |
| BA31 | ++ | ++ | ++ | + | + | ++ | + |
| BA152 | +++ | +++ | +++ | + | ++ | ++ | ++ |
| BA149 | ++ | +++ | +++ | ++ | ++ | ++ | ++ |
| BA32 | ++ | ++ | ++ | + | + | + | ++ |
| BA55 | ++ | ++ | ++ | + | + | ++ | ++ |
| BA35 | ++ | ++ | ++ | ++ | ++ | ++ | ++ |
| BA34 | ++ | ++ | ++ | ++ | ++ | ++ | ++ |
| BA38 | ++ | ++ | ++ | ++ | + | + | + |
| BA40 | ++ | ++ | ++ | ++ | ++ | ++ | + |
| BA41 | ++ | ++ | ++ | ++ | ++ | + | ++ |
| BA14 | ++ | ++ | ++ | ++ | + | + | ++ |
| BA12 | ++ | ++ | ++ | ++ | ++ | ++ | ++ |
| BA30 | ++ | ++ | ++ | ++ | ++ | +++ | ++ |
| KS208 | ++ | +++ | ++ | ++ | ++ | +++ | ++ |
| BA116 | ++ | +++ | ++ |  | +++ | ++ | ++ |
| BA17 | +++ | +++ | +++ | +++ | +++ | +++ | +++ |
| BA134 | ++ | ++ | ++ | ++ | + | + | ++ |
| BA105 | ++ | +++ | ++ | ++ | ++ | ++ | ++ |
| BA122 | +++ | +++ | +++ | ++ | ++ | +++ | +++ |
| BA111 | + | + | ++ | ++ | ++ | ++ | ++ |
| BA102 | +++ | +++ | +++ | ++ | +++ | +++ | +++ |
| BA112 | ++ | +++ | +++ | ++ | ++ | ++ | ++ |
| BA118 | ++ | ++ | + | ++ | ++ | + | ++ |
| BA130 | ++ | +++ | ++ | ++ | +++ | + | ++ |
| BA132 | ++ | +++ | ++ | + | ++ | ++ | ++ |
| BA139 | ++ | ++ | ++ | + | ++ | ++ | + |
| BA158 | +++ | +++ | +++ | ++ | ++ | ++ | ++ |
| BA140 | ++ | ++ | ++ | ++ | + | ++ | ++ |
| BA141 | + | ++ | + | + | + | ++ | + |
| BA146 | ++ | ++ | ++ | + | ++ | ++ | ++ |
| BA142 | ++ | ++ | +++ | + | ++ | ++ | ++ |
| BA145 | + | ++ | ++ | + | + | + | ++ |
| BA147 | ++ | ++ | ++ | + | ++ | + | ++ |
| BA148 | + | ++ | ++ | + | + | ++ | + |
| BA143 | ++ | ++ | ++ | ++ | + | ++ | ++ |
| BA144 | ++ | ++ | +++ | + | ++ | + | ++ |
| BA129 | ++ | + | +++ | + | ++ | ++ | ++ |
| BA131 | ++ | ++ | 11 | + | ++ | ++ | ++ |
| BA133 | ++ | ++ | +++ | + | + | ++ | ++ |
| BA120 | +++ | +++ | +++ | ++ | +++ | ++ | ++ |
| BA108 | +++ | +++ | +++ | +++ | +++ | +++ | +++ |
| BA121 | +++ | +++ | +++ | +++ | +++ | +++ | +++ |
| BA89 | +++ | +++ | +++ | +++ | +++ | +++ | +++ |
| BA94 | +++ | +++ | +++ | +++ | +++ | +++ | +++ |
| BA135 | +++ | +++ | +++ | ++ | +++ | +++ | + |
| BA136 | +++ | +++ | +++ | ++ | +++ |  | ++ |
| BA137 | +++ | +++ | +++ | +++ | +++ | ++ | ++ |
| BA138 | +++ | +++ | +++ | +++ | +++ | +++ | ++ |
| BA160 | +++ | +++ | +++ | ++ | ++ | +++ | ++ |
| BA157_3 | ++ | +++ | +++ | ++ | + | ++ | ++ |
| BA154 | +++ | +++ | +++ | ++ | ++ | ++ | ++ |
| BA110 | +++ | +++ | +++ | ++ | +++ | ++ | ++ |
| BA115 | +++ | +++ | +++ | +++ | +++ | +++ |  |
| BA159 | +++ | +++ | +++ | ++ | +++ | ++ | ++ |
| BA119 | ++ | +++ | +++ | ++ | ++ | ++ | ++ |
| BA107 | +++ | +++ | +++ | ++ | +++ | +++ | +++ |
| BA124 | +++ | +++ | +++ | +++ | +++ | +++ | +++ |
| BA161 | ++ | + | ++ | + | + | ++ | + |
| BA162 | ++ | ++ | ++ | + | + | ++ | ++ |
| BA24dd | ++ | ++ | ++ | ++ | ++ | ++ | ++ |
| BA43 | ++ | +++ | ++ | ++ | ++ | ++ | ++ |
| BA91 | ++ | ++ | +++ | ++ | ++ | ++ | ++ |
| BA92 | ++ | +++ | ++ | ++ | ++ | ++ | ++ |
| BA86 | +++ | +++ | +++ | ++ | +++ | +++ | +++ |
| BA88 | +++ | +++ | +++ | +++ | +++ | +++ | +++ |
| BA96 | +++ | +++ | +++ | ++ | ++ | +++ | +++ |
| BA97 | +++ | +++ | +++ | ++ | +++ | +++ | +++ |
| BA44 | ++ | ++ | ++ | ++ | + | ++ | + |
| BA156 | ++ | ++ | ++ | ++ | ++ | +++ | ++ |
| BA95 | ++ | +++ | ++ | + | + | ++ | ++ |
| BA54 | ++ | ++ | +++ | ++ | ++ | ++ | ++ |
| BA42 | + | ++ | ++ | ++ | ++ | + | ++ |
| SU11248 | +++ | +++ | +++ | +++ | +++ | ++ | + |
| BAY43-9006 | +++ | +++ | +++ | +++ | +++ | + | ++ |
| Dasatinib |  |  | ++ | + |  |  | +++ |

TABLE 3-continued

| Cpd | Abl | Hck | Src | Src (T/I) | VEGFR | EGFR | EphB4 |
|---|---|---|---|---|---|---|---|
| Iressa | ++ | +++ | +++ | ++ | ++ |  | ++ |
| PIK103 | + | + | + | + | + | + | + |
| PIK90 | + | + | + | + | + | + | + |
| PIK294 | ++ | + | ++ | + | + | + | + |

TABLE 4

| Cpd | cKIT | Tie2 | FLT3 | PDGFR | RET | IR | mTOR |
|---|---|---|---|---|---|---|---|
| ZK358 | +++ | ++ | +++ | +++ | +++ | ++ | +++ |
| ZK487 | +++ | +++ | +++ | +++ | +++ | + | +++ |
| ZK349 | +++ | +++ | +++ | +++ | +++ | ++ | +++ |
| ZK494 | +++ | ++ | ++ | +++ | +++ | + | +++ |
| BA102 | +++ | +++ | +++ | +++ | +++ | + | +++ |
| BA121 | +++ | +++ | +++ | +++ |  | ++ | +++ |
| KS84 | +++ | + | +++ | +++ | +++ | ++ | ++ |
| SU11248 | +++ | ++ | +++ | +++ | +++ | ++ | + |
| BAY43-9006 | +++ | +++ | + | +++ | +++ | ++ | + |
| Dasatinib | +++ | ++ | +++ | +++ | ++ | + | + |
| Iressa | + | ++ | +++ | +++ | ++ | + | + |

In Tables 2-4 above, a +++ indicates an IC50 of less than 1 µM; a ++ indicates an IC50 of from 1 µM to 50 µM; and a + indicates and IC50 of more than 50 µM.

IX. References

Alaimo, P. J., Knight, Z. A., and Shokat, K. M. (2005). Targeting the gatekeeper residue in phosphoinositide 3-kinases. Bioorg Med Chem 13, 2825-2836.

Asano, T., Kanda, A., Katagiri, H., Nawano, M., Ogihara, T., Inukai, K., Anai, M., Fukushima, Y., Yazaki, Y., Kikuchi, M., et al. (2000). p110beta is up-regulated during differentiation of 3T3-L1 cells and contributes to the highly insulin-responsive glucose transport activity. J Biol Chem 275, 17671-17676.

Bi, L., Okabe, I., Bernard, D. J., and Nussbaum, R. L. (2002). Early embryonic lethality in mice deficient in the p110beta catalytic subunit of PI 3-kinase. Mamm Genome 13, 169-172.

Bi, L., Okabe, I., Bernard, D. J., Wynshaw-Boris, A., and Nussbaum, R. L. (1999). Proliferative defect and embryonic lethality in mice homozygous for a deletion in the p110alpha subunit of phosphoinositide 3-kinase. J Biol Chem 274, 10963-10968.

Brachmann, S. M., Ueki, K., Engelman, J. A., Kahn, R. C., and Cantley, L. C. (2005). Phosphoinositide 3-kinase catalytic subunit deletion and regulatory subunit deletion have opposite effects on insulin sensitivity in mice. Mol Cell Biol 25, 1596-1607.

Camps, M., Ruckle, T., Ji, H., Ardissone, V., Rintelen, F., Shaw, J., Ferrandi, C., Chabert, C., Gillieron, C., Francon, B., et al. (2005). Blockade of PI3Kgamma suppresses joint inflammation and damage in mouse models of rheumatoid arthritis. Nat Med.

Cantley, L. C., and Neel, B. G. (1999). New insights into tumor suppression: PTEN suppresses tumor formation by restraining the phosphoinositide 3-kinase/AKT pathway. Proc Natl Acad Sci USA 96, 4240-4245.

Condliffe, A. M., Davidson, K., Anderson, K. E., Ellson, C. D., Crabbe, T., Okkenhaug, K., Vanhaesebroeck, B., Turner, M., Webb, L., Wymann, M. P., et al. (2005). Sequential activation of class IB and class IA PI3K is important for the primed respiratory burst of human but not murine neutrophils. Blood 106, 1432-1440.

Domin, J., and Waterfield, M. D. (1997). Using structure to define the function of phosphoinositide 3-kinase family members. FEBS Lett 410, 91-95.

Feng, J., Park, J., Cron, P., Hess, D., and Hemmings, B. A. (2004). Identification of a PKB/Akt hydrophobic motif Ser-473 kinase as DNA-dependent protein kinase. J Biol Chem 279, 41189-41196.

Fruman, D. A., Meyers, R. E., and Cantley, L. C. (1998). Phosphoinositide kinases. Annu Rev Biochem 67, 481-507.

Harrington, L. S., Findlay, G. M., and Lamb, R. F. (2005). Restraining PI3K: mTOR signaling goes back to the membrane. Trends Biochem Sci 30, 35-42.

Hickson, I., Zhao, Y., Richardson, C. J., Green, S. J., Martin, N. M., Orr, A. I., Reaper, P. M., Jackson, S. P., Curtin, N. J., and Smith, G. C. (2004). Identification and characterization of a novel and specific inhibitor of the ataxia-telangiectasia mutated kinase ATM. Cancer Res 64, 9152-9159.

Jackson, S. P., Schoenwaelder, S. M., Goncalves, I., Nesbitt, W. S., Yap, C. L., Wright, C. E., Kenche, V., Anderson, K. E., Dopheide, S. M., Yuan, Y., et al. (2005). PI 3-kinase p110beta: a new target for antithrombotic therapy. Nat Med 11, 507-514.

Katso, R., Okkenhaug, K., Ahmadi, K., White, S., Timms, J., and Waterfield, M. D. (2001). Cellular function of phosphoinositide 3-kinases: implications for development, homeostasis, and cancer. Annu Rev Cell Dev Biol 17, 615-675.

Knight, Z. A., Chiang, G. G., Alaimo, P. J., Kenski, D. M., Ho, C. B., Coan, K., Abraham, R. T., and Shokat, K. M. (2004). Isoform-specific phosphoinositide 3-kinase inhibitors from an arylmorpholine scaffold. Bioorg Med Chem 12, 4749-4759.

Knight, Z. A., and Shokat, K. M. (2005). Features of selective kinase inhibitors. Chem Biol 12, 621-637.

Lau, A., Swinbank, K. M., Ahmed, P. S., Taylor, D. L., Jackson, S. P., Smith, G. C., and O'Connor, M. J. (2005). Suppression of HIV-1 infection by a small molecule inhibitor of the ATM kinase. Nat Cell Biol 7, 493-500.

Luo, J., Field, S. J., Lee, J. Y., Engelman, J. A., and Cantley, L. C. (2005). The p85 regulatory subunit of phosphoinositide 3-kinase down-regulates IRS-1 signaling via the formation of a sequestration complex. J Cell Biol 170, 455-464.

Madhusudan, Trafny, E. A., Xuong, N. H., Adams, J. A., Teneyck, L. F., Taylor, S. S., and Sowadski, J. M. (1994). cAMP-Dependent Protein-Kinase—Crystallographic Insights Into Substrate Recognition and Phosphotransfer. Protein Science 3, 176-187.

Patrucco, E., Notte, A., Barberis, L., Selvetella, G., Maffei, A., Brancaccio, M., Marengo, S., Russo, G., Azzolino, O., Rybalkin, S. D., et al. (2004). PI3Kgamma modulates the cardiac response to chronic pressure overload by distinct kinase-dependent and -independent effects. Cell 118, 375-387.

Peng, Y., Woods, R. G., Beamish, H., Ye, R., Lees-Miller, S. P., Lavin, M. F., and Bedford, J. S. (2005). Deficiency in the catalytic subunit of DNA-dependent protein kinase causes down-regulation of ATM. Cancer Res 65, 1670-1677.

Ruderman, N. B., Kapeller, R., White, M. F., and Cantley, L. C. (1990). Activation of phosphatidylinositol 3-kinase by insulin. Proc Natl Acad Sci USA 87, 1411-1415.

Sadhu, C., Masinovsky, B., Dick, K., Sowell, C. G., and Staunton, D. E. (2003). Essential role of phosphoinositide 3-kinase delta in neutrophil directional movement. J Immunol 170, 2647-2654.

Samuels, Y., Wang, Z., Bardelli, A., Silliman, N., Ptak, J., Szabo, S., Yan, H., Gazdar, A., Powell, S. M., Riggins, G. J., et al. (2004). High frequency of mutations of the PIK3CA gene in human cancers. Science 304, 554.

Schindler, T., Bornmann, W., Pellicena, P., Miller, W. T., Clarkson, B., and Kuriyan, J. (2000). Structural mechanism for STI-571 inhibition of abelson tyrosine kinase. Science 289, 1938-1942.

Schindler, T., Sicheri, F., Pico, A., Gazit, A., Levitzki, A., and Kuriyan, J. (1999). Crystal structure of Hck in complex with a Src family-selective tyrosine kinase inhibitor. Mol Cell 3, 639-648.

Schmid, A. C., Byrne, R. D., Vilar, R., and Woscholski, R. (2004). Bisperoxovanadium compounds are potent PTEN inhibitors. FEBS Lett 566, 35-38.

Ueki, K., Fruman, D. A., Yballe, C. M., Fasshauer, M., Klein, J., Asano, T., Cantley, L. C., and Kahn, C. R. (2003). Positive and negative roles of p85 alpha and p85 beta regulatory subunits of phosphoinositide 3-kinase in insulin signaling. J Biol Chem 278, 48453-48466.

Ueki, K., Yballe, C. M., Brachmann, S. M., Vicent, D., Watt, J. M., Kahn, C. R., and Cantley, L. C. (2002). Increased insulin sensitivity in mice lacking p85beta subunit of phosphoinositide 3-kinase. Proc Natl Acad Sci USA 99, 419-424.

Vanhaesebroeck, B., Ali, K., Bilancio, A., Geering, B., and Foukas, L. C. (2005). Signaling by PI3K isoforms: insights from gene-targeted mice. Trends Biochem Sci 30, 194-204.

Viniegra, J. G., Martinez, N., Modirassari, P., Losa, J. H., Parada Cobo, C., Lobo, V. J., Luquero, C. I., Alvarez-Vallina, L., Ramon y Cajal, S., Rojas, J. M., and Sanchez-Prieto, R. (2005). Full activation of PKB/Akt in response to insulin or ionizing radiation is mediated through ATM. J Biol Chem 280, 4029-4036.

Walker, E. H., Pacold, M. E., Perisic, O., Stephens, L., Hawkins, P. T., Wymann, M. P., and Williams, R. L. (2000). Structural determinants of phosphoinositide 3-kinase inhibition by wortmannin, LY294002, quercetin, myricetin, and staurosporine. Mol Cell 6, 909-919.

Walker, E. H., Perisic, O., Ried, C., Stephens, L., and Williams, R. L. (1999). Structural insights into phosphoinositide 3-kinase catalysis and signaling. Nature 402, 313-320.

Ward, S., Sotsios, Y., Dowden, J., Bruce, I., and Finan, P. (2003). Therapeutic potential of phosphoinositide 3-kinase inhibitors. Chem Biol 10, 207-213.

Yart, A., Roche, S., Wetzker, R., Laffargue, M., Tonks, N., Mayeux, P., Chap, H., and Raynal, P. (2002). A function for phosphoinositide 3-kinase beta lipid products in coupling beta gamma to Ras activation in response to lysophosphatidic acid. J Biol Chem 277, 21167-21178.

Yu, J., Zhang, Y., McIlroy, J., Rordorf-Nikolic, T., Orr, G. A., and Backer, J. M. (1998). Regulation of the p85/p110 phosphatidylinositol 3'-kinase: stabilization and inhibition of the p110alpha catalytic subunit by the p85 regulatory subunit. Mol Cell Biol 18, 1379-1387.

Almirante, L., Mugnaini, A., De Toma, N., Gamba, A., and Murmann, W. (1970). Imidazole Derivatives. IV. Synthesis and Pharmacological Activity of Oxygenated Derivatives of Imidazo[1,2-a]pyridine. Journal of Medicinal Chemistry 13, 1048-1051.

Armstrong, V. W., N. H., C., and Ramage, R. (1975). A new brominating reagent: 2-carboxyethyltriphenylphosphonium perbromide. Tetrahedron Letters 6, 373-376.

Bateman, A., Birney, E., Durbin, R., Eddy, S. R., Howe, K. L., and Sonnhammer, E. L. (2000). The Pfam protein families database. Nucleic Acids Res 28, 263-266.

Jacinto, E., Loewith, R., Schmidt, A., Lin, S., Ruegg, M. A., Hall, A., and Hall, M. N. (2004). Mammalian TOR complex 2 controls the actin cytoskeleton and is rapamycin insensitive. Nat Cell Biol 6, 1122-1128.

Jolliffe, I. T. (2002). Principal component analysis, 2nd edn (New York: Springer).

Knight, Z. A., Chiang, G. G., Alaimo, P. J., Kenski, D. M., Ho, C. B., Coan, K., Abraham, R. T., and Shokat, K. M. (2004). Isoform-specific phosphoinositide 3-kinase inhibitors from an arylmorpholine scaffold. Bioorg Med Chem 12, 4749-4759.

Lakshmanan, J., Elmendorf, J. S., and Ozcan, S. (2003). Analysis of insulin-stimulated glucose uptake in differentiated 3T3-L1 adipocytes. Methods Mol Med 83, 97-103.

Lombardino, J. G. (1965). Preparation and new reactions of imidazo[1,2-a]pyridines. Journal of Organic Chemistry 30, 2403-2407.

Mathworks (2004). Statistics Toolbox: For use with MATLAB. User's Guide, Version 5. Chapter 7: Principal Component Analysis: Mathworks).

Mhaske, S. B., and Argade, N. P. (2004). Regioselective quinazolinone-directed ortho lithiation of quinazolinoylquinoline: practical synthesis of naturally occurring human DNA topoisomerase I poison luotonin a and luotonins B and E. J Org Chem 69, 4563-4566.

Morris, J., Wishka, D. G., and Fang, Y. (1994). A cyclodehydration route to 2-aminochromones. Synthetic Communications 24, 849-858.

Serunian, L. A., Auger, K. R., and Cantley, L. C. (1991). Identification and quantification of polyphosphoinositides produced in response to platelet-derived growth factor stimulation. Methods Enzymol 198, 78-87.

---

What is claimed is:

1. A method of treating cancer in a subject in need of such treatment, said method comprising administering to said subject a therapeutically effective amount of an antagonist, wherein said antagonist has the formula:

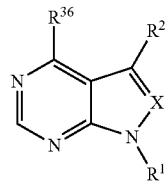

(I)

wherein

X is =N—;

$R^1$ is hydrogen, $R^3$-substituted or unsubstituted alkyl, unsubstituted cycloalkyl, unsubstituted heterocycloalkyl, or $R^3$-substituted heteroaryl; and $R^2$ is $R^4$-substituted heteroaryl;

$R^3$ is halogen, —CN, —$OR^5$, —$S(O)_nR^6$, —$NR^7R^8$, —$C(O)R^9$, —$NR^{10}$—$C(O)R^{11}$, —$NR^{12}$—$C(O)$—$OR^{13}$, —$C(O)NR^{14}R^{15}$, —$NR^{16}S(O)_2R^{17}$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl, wherein n is an integer from 0 to 2;

$R^4$ is halogen, —CN, —$OR^{20}$, —$NR^{22}R^{23}$;

$R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are independently hydrogen, $R^{35}$-substituted or unsubstituted alkyl, $R^{35}$-substituted or unsubstituted heteroalkyl, unsubstituted cycloalkyl, $R^{35}$-substituted or unsubstituted heterocycloalkyl, $R^{35}$-substituted or unsubstituted aryl, or $R^{35}$-substituted or unsubstituted heteroaryl;

$R^{19}$ and $R^{35}$ are independently hydrogen, halogen, unsubstituted alkyl, unsubstituted heteroalkyl, unsubstituted cycloalkyl, unsubstituted heterocycloalkyl, unsubstituted aryl, or unsubstituted heteroaryl;

$R^{20}$, $R^{22}$, and $R^{23}$ are hydrogen;

$R^{36}$ is —$NR^{37}R^{38}$; and $R^{37}$ and $R^{38}$ are hydrogen.

2. The method of claim 1, wherein $R^2$ has the formula:

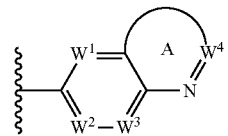

(III)

wherein $W^1$, $W^2$, $W^3$, and $W^4$ are independently =CH—, =$CR^4$—, or =N—; and ring A is a partially or fully unsaturated 6- or 7- membered ring.

3. The method of claim 1, wherein said cancer is selected from the group consisting of liver cancer, colon cancer, breast cancer, melanoma, kidney cancer, bladder cancer, endometrial cancer, and non-small-cell lung cancer.

4. The method according to claim 1, wherein $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ are independently hydrogen, unsubstituted alkyl, unsubstituted heteroalkyl, unsubstituted cycloalkyl, unsubstituted heterocycloalkyl, unsubstituted aryl, or unsubstituted heteroaryl.

5. The method according to claim 1, wherein $R^1$ is $R^3$-substituted or unsubstituted alkyl, or unsubstituted heterocycloalkyl.

6. The method according to claim 1, wherein $R^1$ is $R^3$-substituted or unsubstituted alkyl.

7. The method according to claim 1, wherein $R^1$ is $R^3$-substituted or unsubstituted $C_1$-$C_4$ alkyl.

8. The method according to claim 1, wherein $R^1$ is methyl or unsubstituted $C_3$-$C_6$ branched alkyl.

9. The method according to claim 1, wherein $R^1$ is isopropyl.

10. The method according to claim 1, wherein $R^3$ is $R^{19}$-substituted or unsubstituted alkyl, $R^{19}$-substituted or unsubstituted cycloalkyl, or $R^{19}$-substituted or unsubstituted aryl.

11. The method according to claim 1, wherein $R^3$ is $R^{19}$-substituted or unsubstituted alkyl, or $R^{19}$-substituted or unsubstituted cycloalkyl.

12. The method according to claim 1, wherein $R^{19}$ is unsubstituted alkyl or unsubstituted cycloalkyl.

13. The method according to claim 1, wherein $R^{19}$ is unsubstituted $C_1$-$C_4$ alkyl or unsubstituted cyclopentyl.

14. The method according to claim 1, wherein $R^2$ is $R^4$-substituted pyridinyl, $R^4$-substituted pyrimidinyl, $R^4$-substituted thiophenyl, $R^4$-substituted furanyl, $R^4$-substituted indolyl, $R^4$-substituted benzoxadiazolyl, $R^4$-substituted benzodioxolyl, $R^4$-substituted benzodioxanyl, $R^4$-substituted thianaphthanyl, $R^4$-substituted pyrrolopyridinyl, $R^4$-substituted indazolyl, $R^4$-substituted quinolinyl, $R^4$-substituted quinoxalinyl, $R^4$-substituted pyridopyrazinyl, $R^4$-substituted quinazolinonyl, $R^4$-substituted benzoisoxazolyl, $R^4$-substituted imidazopyridinyl, $R^4$-substituted benzofuranyl, or $R^4$-substituted benzothiophenyl.

15. The method according to claim 1, wherein $R^2$ is $R^4$-substituted indolyl.

16. The method according to claim 1, wherein $R^2$ is 5-hydroxy indol-2-yl and $R^1$ is isopropyl.

17. The method of claim 1, wherein said cancer is a carcinoma or sarcoma.

18. The method of claim 1, wherein said cancer is a lymphoma.

19. The method of claim 3, wherein said cancer is acute myelogenous leukemia or chronic myelogenous leukemia.

20. The method of claim 1, wherein said cancer is multiple myeloma.

21. The method of claim 1, wherein said cancer is macroglobulinemia.

22. The method of claim 1, wherein said cancer is leukemia.

23. The method of claim 1, wherein said cancer is selected from the group consisting of bladder cancer, endometrial cancer, kidney cancer, prostate cancer, or non-Hodgkin's lymphoma.

\* \* \* \* \*

UNITED STATES PATENT AND TRADEMARK OFFICE
CERTIFICATE OF CORRECTION

Page 1 of 1

PATENT NO. : 8,642,604 B2
APPLICATION NO. : 12/509281
DATED : February 4, 2014
INVENTOR(S) : Zachary A. Knight, Beth Apsel and Kevan M. Shokat It is certified that error appears in the above-identified patent and that said Letters Patent is hereby corrected as shown below:

In the Specification

Column 1, line 21 - 23, please delete:
"The present invention was supported by a grant from the National Institutes of Health (AI44009). The Government has certain rights to the invention."

and replace it with:
-- This invention was made with government support under grant no. AI044009 awarded by the National Institutes of Health. The government has certain rights in the invention. --

Signed and Sealed this
Eighteenth Day of November, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial
<220> FEATURE:
<223> OTHER INFORMATION: Description of Artificial Sequence: Synthetic
      peptide

<400> SEQUENCE: 1

Glu Ala Ile Tyr Ala Ala Pro Phe Ala Lys Lys Lys
1               5                   10

<210> SEQ ID NO 2
<211> LENGTH: 9
<212> TYPE: PRT
<213> ORGANISM: Artificial
<220> FEATURE:
<223> OTHER INFORMATION: Description of Artificial Sequence: Synthetic
      peptide

<400> SEQUENCE: 2

Glu Ile Tyr Gly Glu Phe Lys Lys Lys
1               5

<210> SEQ ID NO 3
<211> LENGTH: 1044
<212> TYPE: PRT
<213> ORGANISM: Homo sapiens

<400> SEQUENCE: 3

Met Pro Pro Gly Val Asp Cys Pro Met Glu Phe Trp Thr Lys Glu Glu
1               5                   10                  15

Asn Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
        35                  40                  45

Leu Trp His Arg Ala Gln Tyr Glu Pro Leu Phe His Met Leu Ser Gly
    50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110
```

-continued

```
Ile Asn Ser Gln Ile Ser Leu Leu Ile Gly Lys Gly Leu His Glu Phe
            115                 120                 125

Asp Ser Leu Cys Asp Pro Glu Val Asn Asp Phe Arg Ala Lys Met Cys
130                 135                 140

Gln Phe Cys Glu Glu Ala Ala Arg Arg Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
                180                 185                 190

Asn Val Lys Phe Glu Gly Ser Glu Glu Ser Phe Thr Phe Gln Val Ser
            195                 200                 205

Thr Lys Asp Val Pro Leu Ala Leu Met Ala Cys Ala Leu Arg Lys Lys
210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Asn Tyr Pro Leu
                245                 250                 255

Cys Gln Phe Gln Tyr Ile Cys Ser Cys Leu His Ser Gly Leu Thr Pro
                260                 265                 270

His Leu Thr Met Val His Ser Ser Ile Leu Ala Met Arg Asp Glu
            275                 280                 285

Gln Ser Asn Pro Ala Pro Gln Val Gln Lys Pro Arg Ala Lys Pro Pro
290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335

Glu Arg Met Lys Leu Val Val Gln Ala Gly Leu Phe His Gly Asn Glu
                340                 345                 350

Met Leu Cys Lys Thr Val Ser Ser Glu Val Ser Val Cys Ser Glu
            355                 360                 365

Pro Val Trp Lys Gln Arg Leu Glu Phe Asp Ile Asn Ile Cys Asp Leu
370                 375                 380

Pro Arg Met Ala Arg Leu Cys Phe Ala Leu Tyr Ala Val Ile Glu Lys
385                 390                 395                 400

Ala Lys Lys Ala Arg Ser Thr Lys Lys Ser Lys Lys Ala Asp Cys
                405                 410                 415

Pro Ile Ala Trp Ala Asn Leu Met Leu Phe Asp Tyr Lys Asp Gln Leu
                420                 425                 430

Lys Thr Gly Glu Arg Cys Leu Tyr Met Trp Pro Ser Val Pro Asp Glu
            435                 440                 445

Lys Gly Glu Leu Leu Asn Pro Thr Gly Thr Val Arg Ser Asn Pro Asn
450                 455                 460

Thr Asp Ser Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                485                 490                 495

His Ser Glu Cys Val His Val Thr Glu Glu Gln Leu Gln Leu Arg
            500                 505                 510

Glu Ile Leu Glu Arg Arg Gly Ser Gly Glu Leu Tyr Glu His Glu Lys
            515                 520                 525

Asp Leu Val Trp Lys Leu Arg His Glu Val Gln Glu His Phe Pro Glu
```

```
              530                 535                 540
Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                    565                 570                 575

Leu Ser Ala Leu Glu Leu Leu Asp Phe Ser Phe Pro Asp Cys His Val
                580                 585                 590

Gly Ser Phe Ala Ile Lys Ser Leu Arg Lys Leu Thr Asp Asp Glu Leu
            595                 600                 605

Phe Gln Tyr Leu Leu Gln Leu Val Gln Val Leu Lys Tyr Glu Ser Tyr
        610                 615                 620

Leu Asp Cys Glu Leu Thr Lys Phe Leu Leu Asp Arg Ala Leu Ala Asn
625                 630                 635                 640

Arg Lys Ile Gly His Phe Leu Phe Trp His Leu Arg Ser Glu Met His
                    645                 650                 655

Val Pro Ser Val Ala Leu Arg Phe Gly Leu Ile Leu Glu Ala Tyr Cys
                660                 665                 670

Arg Gly Ser Thr His His Met Lys Val Leu Met Lys Gln Gly Glu Ala
            675                 680                 685

Leu Ser Lys Leu Lys Ala Leu Asn Asp Phe Val Lys Leu Ser Ser Gln
        690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
                    725                 730                 735

Pro Ser Thr Leu Leu Ala Glu Val Cys Val Glu Gln Cys Thr Phe Met
                740                 745                 750

Asp Ser Lys Met Lys Pro Leu Trp Ile Met Tyr Ser Asn Glu Glu Ala
            755                 760                 765

Gly Ser Gly Gly Ser Val Gly Ile Ile Phe Lys Asn Gly Asp Asp Leu
        770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                    805                 810                 815

Pro Thr Gly Asp Arg Thr Gly Leu Ile Glu Val Val Leu Arg Ser Asp
                820                 825                 830

Thr Ile Ala Asn Ile Gln Leu Asn Lys Ser Asn Met Ala Ala Thr Ala
            835                 840                 845

Ala Phe Asn Lys Asp Ala Leu Leu Asn Trp Leu Lys Ser Lys Asn Pro
850                 855                 860

Gly Glu Ala Leu Asp Arg Ala Ile Glu Glu Phe Thr Leu Ser Cys Ala
865                 870                 875                 880

Gly Tyr Cys Val Ala Thr Tyr Val Leu Gly Ile Gly Asp Arg His Ser
                885                 890                 895

Asp Asn Ile Met Ile Arg Glu Ser Gly Gln Leu Phe His Ile Asp Phe
            900                 905                 910

Gly His Phe Leu Gly Asn Phe Lys Thr Lys Phe Gly Ile Asn Arg Glu
        915                 920                 925

Arg Val Pro Phe Ile Leu Thr Tyr Asp Phe Val His Val Ile Gln Gln
            930                 935                 940

Gly Lys Thr Asn Asn Ser Glu Lys Phe Glu Arg Phe Arg Gly Tyr Cys
945                 950                 955                 960
```

```
Glu Arg Ala Tyr Thr Ile Leu Arg Arg His Gly Leu Phe Leu His
                965                 970                 975

Leu Phe Ala Leu Met Arg Ala Ala Gly Leu Pro Glu Leu Ser Cys Ser
            980                 985                 990

Lys Asp Ile Gln Tyr Leu Lys Asp Ser Leu Ala Leu Gly Lys Thr Glu
            995                1000                1005

Glu Glu Ala Leu Lys His Phe Arg Val Lys Phe Asn Glu Ala Leu
    1010                1015                1020

Arg Glu Ser Trp Lys Thr Lys Val Asn Trp Leu Ala His Asn Val
    1025                1030                1035

Ser Lys Asp Asn Arg Gln
    1040

<210> SEQ ID NO 4
<211> LENGTH: 1102
<212> TYPE: PRT
<213> ORGANISM: Homo sapiens

<400> SEQUENCE: 4

Met Glu Leu Glu Asn Tyr Lys Gln Pro Val Val Leu Arg Glu Asp Asn
1               5                   10                  15

Cys Arg Arg Arg Arg Met Lys Pro Arg Ser Ala Ala Ser Leu
            20                  25                  30

Ser Ser Met Glu Leu Ile Pro Ile Glu Phe Val Leu Pro Thr Ser Gln
            35                  40                  45

Arg Lys Cys Lys Ser Pro Glu Thr Ala Leu Leu His Val Ala Gly His
            50                  55                  60

Gly Asn Val Glu Gln Met Lys Ala Gln Val Trp Leu Arg Ala Leu Glu
65                  70                  75                  80

Thr Ser Val Ala Ala Asp Phe Tyr His Arg Leu Gly Pro His His Phe
                85                  90                  95

Leu Leu Leu Tyr Gln Lys Lys Gly Gln Trp Tyr Glu Ile Tyr Asp Lys
                100                 105                 110

Tyr Gln Val Val Gln Thr Leu Asp Cys Leu Arg Tyr Trp Lys Ala Thr
            115                 120                 125

His Arg Ser Pro Gly Gln Ile His Leu Val Gln Arg His Pro Pro Ser
    130                 135                 140

Glu Glu Ser Gln Ala Phe Gln Arg Gln Leu Thr Ala Leu Ile Gly Tyr
145                 150                 155                 160

Asp Val Thr Asp Val Ser Asn Val His Asp Asp Glu Leu Glu Phe Thr
                165                 170                 175

Arg Arg Gly Leu Val Thr Pro Arg Met Ala Glu Val Ala Ser Arg Asp
            180                 185                 190

Pro Lys Leu Tyr Ala Met His Pro Trp Val Thr Ser Lys Pro Leu Pro
            195                 200                 205

Glu Tyr Leu Trp Lys Lys Ile Ala Asn Asn Cys Ile Phe Ile Val Ile
    210                 215                 220

His Arg Ser Thr Thr Ser Gln Thr Ile Lys Val Ser Pro Asp Thr
225                 230                 235                 240

Pro Gly Ala Ile Leu Gln Ser Phe Phe Thr Lys Met Ala Lys Lys Lys
                245                 250                 255

Ser Leu Met Asp Ile Pro Glu Ser Gln Ser Glu Gln Asp Phe Val Leu
            260                 265                 270

Arg Val Cys Gly Arg Asp Glu Tyr Leu Val Gly Glu Thr Pro Ile Lys
            275                 280                 285
```

-continued

| | | | | | | | | | | | | | | |
|---|---|---|---|---|---|---|---|---|---|---|---|---|---|---|
| Asn | Phe | Gln | Trp | Val | Arg | His | Cys | Leu | Lys | Asn | Gly | Glu | Glu | Ile | His |
| | 290 | | | | 295 | | | | 300 | | | | | |
| Val | Val | Leu | Asp | Thr | Pro | Asp | Pro | Ala | Leu | Asp | Glu | Val | Arg | Lys |
| 305 | | | | | 310 | | | | 315 | | | | | 320 |
| Glu | Glu | Trp | Pro | Leu | Val | Asp | Asp | Cys | Thr | Gly | Val | Thr | Gly | Tyr | His |
| | | | 325 | | | | | 330 | | | | | 335 | |
| Glu | Gln | Leu | Thr | Ile | His | Gly | Lys | Asp | His | Glu | Ser | Val | Phe | Thr | Val |
| | | | 340 | | | | | 345 | | | | | 350 | |
| Ser | Leu | Trp | Asp | Cys | Asp | Arg | Lys | Phe | Arg | Val | Lys | Ile | Arg | Gly | Ile |
| | | 355 | | | | | 360 | | | | | 365 | | |
| Asp | Ile | Pro | Val | Leu | Pro | Arg | Asn | Thr | Asp | Leu | Thr | Val | Phe | Val | Glu |
| | 370 | | | | | 375 | | | | | 380 | | | |
| Ala | Asn | Ile | Gln | His | Gly | Gln | Gln | Val | Leu | Cys | Gln | Arg | Arg | Thr | Ser |
| 385 | | | | | 390 | | | | | 395 | | | | | 400 |
| Pro | Lys | Pro | Phe | Thr | Glu | Val | Leu | Trp | Asn | Val | Trp | Leu | Glu | Phe |
| | | | | 405 | | | | | 410 | | | | | 415 |
| Ser | Ile | Lys | Ile | Lys | Asp | Leu | Pro | Lys | Gly | Ala | Leu | Leu | Asn | Leu | Gln |
| | | | 420 | | | | | 425 | | | | | 430 | | |
| Ile | Tyr | Cys | Gly | Lys | Ala | Pro | Ala | Leu | Ser | Ser | Lys | Ala | Ser | Ala | Glu |
| | | 435 | | | | | 440 | | | | | 445 | | | |
| Ser | Pro | Ser | Ser | Glu | Ser | Lys | Gly | Lys | Val | Gln | Leu | Leu | Tyr | Tyr | Val |
| | 450 | | | | | 455 | | | | | 460 | | | |
| Asn | Leu | Leu | Leu | Ile | Asp | His | Arg | Phe | Leu | Leu | Arg | Arg | Gly | Glu | Tyr |
| 465 | | | | | 470 | | | | | 475 | | | | | 480 |
| Val | Leu | His | Met | Trp | Gln | Ile | Ser | Gly | Lys | Gly | Glu | Asp | Gln | Gly | Ser |
| | | | | 485 | | | | | 490 | | | | | 495 | |
| Phe | Asn | Ala | Asp | Lys | Leu | Thr | Ser | Ala | Thr | Asn | Pro | Asp | Lys | Glu | Asn |
| | | | | 500 | | | | | 505 | | | | | 510 | |
| Ser | Met | Ser | Ile | Ser | Ile | Leu | Leu | Asp | Asn | Tyr | Cys | His | Pro | Ile | Ala |
| | | | 515 | | | | | 520 | | | | | 525 | | |
| Leu | Pro | Lys | His | Gln | Pro | Thr | Pro | Asp | Pro | Glu | Gly | Asp | Arg | Val | Arg |
| | | 530 | | | | | 535 | | | | | 540 | | | |
| Ala | Glu | Met | Pro | Asn | Gln | Leu | Arg | Lys | Gln | Leu | Glu | Ala | Ile | Ile | Ala |
| 545 | | | | | 550 | | | | | 555 | | | | | 560 |
| Thr | Asp | Pro | Leu | Asn | Pro | Leu | Thr | Ala | Glu | Asp | Lys | Glu | Leu | Leu | Trp |
| | | | | 565 | | | | | 570 | | | | | 575 | |
| His | Phe | Arg | Tyr | Glu | Ser | Leu | Lys | His | Pro | Lys | Ala | Tyr | Pro | Lys | Leu |
| | | | 580 | | | | | 585 | | | | | 590 | | |
| Phe | Ser | Ser | Val | Lys | Trp | Gly | Gln | Gln | Glu | Ile | Val | Ala | Lys | Thr | Tyr |
| | | 595 | | | | | 600 | | | | | 605 | | | |
| Gln | Leu | Leu | Ala | Arg | Arg | Glu | Val | Trp | Asp | Gln | Ser | Ala | Leu | Asp | Val |
| | 610 | | | | | 615 | | | | | 620 | | | | |
| Gly | Leu | Thr | Met | Gln | Leu | Leu | Asp | Cys | Asn | Phe | Ser | Asp | Glu | Asn | Val |
| 625 | | | | | 630 | | | | | 635 | | | | | 640 |
| Arg | Ala | Ile | Ala | Val | Gln | Lys | Leu | Glu | Ser | Leu | Glu | Asp | Asp | Val |
| | | | | 645 | | | | | 650 | | | | | 655 |
| Leu | His | Tyr | Leu | Leu | Gln | Leu | Val | Gln | Ala | Val | Lys | Phe | Glu | Pro | Tyr |
| | | | 660 | | | | | 665 | | | | | 670 | | |
| His | Asp | Ser | Ala | Leu | Ala | Arg | Phe | Leu | Leu | Lys | Arg | Gly | Leu | Arg | Asn |
| | | 675 | | | | | 680 | | | | | 685 | | | |
| Lys | Arg | Ile | Gly | His | Phe | Leu | Phe | Trp | Phe | Leu | Arg | Ser | Glu | Ile | Ala |
| | 690 | | | | | 695 | | | | | 700 | | | | |
| Gln | Ser | Arg | His | Tyr | Gln | Gln | Arg | Phe | Ala | Val | Ile | Leu | Glu | Ala | Tyr |
| 705 | | | | | 710 | | | | | 715 | | | | | 720 |

```
Leu Arg Gly Cys Gly Thr Ala Met Leu His Asp Phe Thr Gln Gln Val
                725                 730                 735

Gln Val Ile Glu Met Leu Gln Lys Val Thr Leu Asp Ile Lys Ser Leu
            740                 745                 750

Ser Ala Glu Lys Tyr Asp Val Ser Ser Gln Val Ile Ser Gln Leu Lys
        755                 760                 765

Gln Lys Leu Glu Asn Leu Gln Asn Ser Gln Leu Pro Glu Ser Phe Arg
    770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Pro Leu Trp Leu Glu Phe Lys
                805                 810                 815

Cys Ala Asp Pro Thr Ala Leu Ser Asn Glu Thr Ile Gly Ile Phe
                820                 825                 830

Lys His Gly Asp Asp Leu Arg Gln Asp Met Leu Ile Leu Gln Ile Leu
        835                 840                 845

Arg Ile Met Glu Ser Ile Trp Glu Thr Glu Ser Leu Asp Leu Cys Leu
    850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
                885                 890                 895

Gly Asn Thr Gly Ala Phe Lys Asp Glu Val Leu Asn His Trp Leu Lys
        900                 905                 910

Glu Lys Ser Pro Thr Glu Glu Lys Phe Gln Ala Ala Val Glu Arg Phe
    915                 920                 925

Val Tyr Ser Cys Ala Gly Tyr Cys Val Ala Thr Phe Val Leu Gly Ile
930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
            965                 970                 975

Gly Ile Asn Lys Glu Arg Val Pro Phe Val Leu Thr Pro Asp Phe Leu
        980                 985                 990

Phe Val Met Gly Thr Ser Gly Lys  Lys Thr Ser Pro His  Phe Gln Lys
            995                 1000                1005

Phe Gln  Asp Ile Cys Val Lys  Ala Tyr Leu Ala Leu  Arg His His
    1010                 1015                1020

Thr Asn  Leu Leu Ile Ile Leu  Phe Ser Met Met Leu  Met Thr Gly
    1025                 1030                1035

Met Pro  Gln Leu Thr Ser Lys  Glu Asp Ile Glu Tyr  Ile Arg Asp
    1040                 1045                1050

Ala Leu  Thr Val Gly Lys Asn  Glu Glu Asp Ala Lys  Lys Tyr Phe
    1055                 1060                1065

Leu Asp  Gln Ile Glu Val Cys  Arg Asp Lys Gly Trp  Thr Val Gln
    1070                 1075                1080

Phe Asn  Trp Phe Leu His Leu  Val Leu Gly Ile Lys  Gln Gly Glu
    1085                 1090                1095

Lys His  Ser Ala
    1100

<210> SEQ ID NO 5
<211> LENGTH: 1068
<212> TYPE: PRT
```

<213> ORGANISM: Homo sapiens

<400> SEQUENCE: 5

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys

-continued

```
               405                 410                 415
Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
            435                 440                 445

Pro His Gly Leu Glu Asp Leu Leu Asn Pro Ile Gly Val Thr Gly Ser
            450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
            515                 520                 525

Glu Gln Leu Lys Ala Ile Ser Thr Arg Asp Pro Leu Ser Glu Ile Thr
            530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
            595                 600                 605

Pro Met Val Arg Gly Phe Ala Val Arg Cys Leu Glu Lys Tyr Leu Thr
            610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
            675                 680                 685

Glu Ser Tyr Cys Arg Ala Cys Gly Met Tyr Leu Lys His Leu Asn Arg
            690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
            755                 760                 765

Cys Arg Ile Met Ser Ser Ala Lys Arg Pro Leu Trp Leu Asn Trp Glu
            770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830
```

Met Leu Pro Tyr Gly Cys Leu Ser Ile Gly Asp Cys Val Gly Leu Ile
            835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
            885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
            915                 920                 925

Leu Phe His Ile Asp Phe Gly His Phe Leu Asp His Lys Lys Lys Lys
            930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
            965                 970                 975

Phe Glu Arg Phe Gln Glu Met Cys Tyr Lys Ala Tyr Leu Ala Ile Arg
            980                 985                 990

Gln His Ala Asn Leu Phe Ile Asn Leu Phe Ser Met Met Leu Gly Ser
            995                1000                1005

Gly Met Pro Glu Leu Gln Ser Phe Asp Asp Ile Ala Tyr Ile Arg
    1010                1015                1020

Lys Thr Leu Ala Leu Asp Lys Thr Glu Gln Glu Ala Leu Glu Tyr
    1025                1030                1035

Phe Met Lys Gln Met Asn Asp Ala His His Gly Gly Trp Thr Thr
    1040                1045                1050

Lys Met Asp Trp Ile Phe His Thr Ile Lys Gln His Ala Leu Asn
    1055                1060                1065

<210> SEQ ID NO 6
<211> LENGTH: 1070
<212> TYPE: PRT
<213> ORGANISM: Homo sapiens

<400> SEQUENCE: 6

Met Cys Phe Ser Phe Ile Met Pro Pro Ala Met Ala Asp Ile Leu Asp
1               5                   10                  15

Ile Trp Ala Val Asp Ser Gln Ile Ala Ser Asp Gly Ser Ile Pro Val
            20                  25                  30

Asp Phe Leu Leu Pro Thr Gly Ile Tyr Ile Gln Leu Glu Val Pro Arg
            35                  40                  45

Glu Ala Thr Ile Ser Tyr Ile Lys Gln Met Leu Trp Lys Gln Val His
    50                  55                  60

Asn Tyr Pro Met Phe Asn Leu Leu Met Asp Ile Asp Ser Tyr Met Phe
65                  70                  75                  80

Ala Cys Val Asn Gln Thr Ala Val Tyr Glu Glu Leu Glu Asp Glu Thr
            85                  90                  95

Arg Arg Leu Cys Asp Val Arg Pro Phe Leu Pro Val Leu Lys Leu Val
            100                 105                 110

Thr Arg Ser Cys Asp Pro Gly Glu Lys Leu Asp Ser Lys Ile Gly Val
            115                 120                 125

Leu Ile Gly Lys Gly Leu His Glu Phe Asp Ser Leu Lys Asp Pro Glu
    130                 135                 140

```
Val Asn Glu Phe Arg Arg Lys Met Arg Lys Phe Ser Glu Glu Lys Ile
145                 150                 155                 160

Leu Ser Leu Val Gly Leu Ser Trp Met Asp Trp Leu Lys Gln Thr Tyr
                165                 170                 175

Pro Pro Glu His Glu Pro Ser Ile Pro Glu Asn Leu Glu Asp Lys Leu
            180                 185                 190

Tyr Gly Gly Lys Leu Ile Val Ala Val His Phe Glu Asn Cys Gln Asp
        195                 200                 205

Val Phe Ser Phe Gln Val Ser Pro Asn Met Asn Pro Ile Lys Val Asn
    210                 215                 220

Glu Leu Ala Ile Gln Lys Arg Leu Thr Ile His Gly Lys Glu Asp Glu
225                 230                 235                 240

Val Ser Pro Tyr Asp Tyr Val Leu Gln Val Ser Gly Arg Val Glu Tyr
                245                 250                 255

Val Phe Gly Asp His Pro Leu Ile Gln Phe Gln Tyr Ile Arg Asn Cys
            260                 265                 270

Val Met Asn Arg Ala Leu Pro His Phe Ile Leu Val Glu Cys Cys Lys
        275                 280                 285

Ile Lys Lys Met Tyr Glu Gln Glu Met Ile Ala Ile Glu Ala Ala Ile
    290                 295                 300

Asn Arg Asn Ser Ser Asn Leu Pro Leu Pro Leu Pro Pro Lys Lys Thr
305                 310                 315                 320

Arg Ile Ile Ser His Val Trp Glu Asn Asn Asn Pro Phe Gln Ile Val
                325                 330                 335

Leu Val Lys Gly Asn Lys Leu Asn Thr Glu Thr Val Lys Val His
            340                 345                 350

Val Arg Ala Gly Leu Phe His Gly Thr Glu Leu Leu Cys Lys Thr Ile
        355                 360                 365

Val Ser Ser Glu Val Ser Gly Lys Asn Asp His Ile Trp Asn Glu Pro
    370                 375                 380

Leu Glu Phe Asp Ile Asn Ile Cys Asp Leu Pro Arg Met Ala Arg Leu
385                 390                 395                 400

Cys Phe Ala Val Tyr Ala Val Leu Asp Lys Val Lys Thr Lys Lys Ser
                405                 410                 415

Thr Lys Thr Ile Asn Pro Ser Lys Tyr Gln Thr Ile Arg Lys Ala Gly
            420                 425                 430

Lys Val His Tyr Pro Val Ala Trp Val Asn Thr Met Val Phe Asp Phe
        435                 440                 445

Lys Gly Gln Leu Arg Thr Gly Asp Ile Ile Leu His Ser Trp Ser Ser
    450                 455                 460

Phe Pro Asp Glu Leu Glu Glu Met Leu Asn Pro Met Gly Thr Val Gln
465                 470                 475                 480

Thr Asn Pro Tyr Thr Glu Asn Ala Thr Ala Leu His Val Lys Phe Pro
                485                 490                 495

Glu Asn Lys Lys Gln Pro Tyr Tyr Pro Pro Phe Asp Lys Ile Ile
            500                 505                 510

Glu Lys Ala Ala Glu Ile Ala Ser Ser Asp Ser Ala Asn Val Ser Ser
        515                 520                 525

Arg Gly Gly Lys Lys Phe Leu Pro Val Leu Lys Glu Ile Leu Asp Arg
    530                 535                 540

Asp Pro Leu Ser Gln Leu Cys Glu Asn Glu Met Asp Leu Ile Trp Thr
545                 550                 555                 560

Leu Arg Gln Asp Cys Arg Glu Ile Phe Pro Gln Ser Leu Pro Lys Leu
                565                 570                 575
```

```
Leu Leu Ser Ile Lys Trp Asn Lys Leu Glu Asp Val Ala Gln Leu Gln
            580                 585                 590

Ala Leu Leu Gln Ile Trp Pro Lys Leu Pro Arg Glu Ala Leu Glu
        595                 600                 605

Leu Leu Asp Phe Asn Tyr Pro Asp Gln Tyr Val Arg Glu Tyr Ala Val
610                 615                 620

Gly Cys Leu Arg Gln Met Ser Asp Glu Leu Ser Gln Tyr Leu Leu
625                 630                 635                 640

Gln Leu Val Gln Val Leu Lys Tyr Glu Pro Phe Leu Asp Cys Ala Leu
                645                 650                 655

Ser Arg Phe Leu Leu Glu Arg Ala Leu Gly Asn Arg Arg Ile Gly Gln
            660                 665                 670

Phe Leu Phe Trp His Leu Arg Ser Glu Val His Ile Pro Ala Val Ser
        675                 680                 685

Val Gln Phe Gly Val Ile Leu Glu Ala Tyr Cys Arg Gly Ser Val Gly
690                 695                 700

His Met Lys Val Leu Ser Lys Gln Val Glu Ala Leu Asn Lys Leu Lys
705                 710                 715                 720

Thr Leu Asn Ser Leu Ile Lys Leu Asn Ala Val Lys Leu Asn Arg Ala
                725                 730                 735

Lys Gly Lys Glu Ala Met His Thr Cys Leu Lys Gln Ser Ala Tyr Arg
            740                 745                 750

Glu Ala Leu Ser Asp Leu Gln Ser Pro Leu Asn Pro Cys Val Ile Leu
        755                 760                 765

Ser Glu Leu Tyr Val Glu Lys Cys Lys Tyr Met Asp Ser Lys Met Lys
770                 775                 780

Pro Leu Trp Leu Val Tyr Asn Asn Lys Val Phe Gly Glu Asp Ser Val
785                 790                 795                 800

Gly Val Ile Phe Lys Asn Gly Asp Asp Leu Arg Gln Asp Met Leu Thr
                805                 810                 815

Leu Gln Met Leu Arg Leu Met Asp Leu Leu Trp Lys Glu Ala Gly Leu
            820                 825                 830

Asp Leu Arg Met Leu Pro Tyr Gly Cys Leu Ala Thr Gly Asp Arg Ser
        835                 840                 845

Gly Leu Ile Glu Val Val Ser Thr Ser Glu Thr Ile Ala Asp Ile Gln
850                 855                 860

Leu Asn Ser Ser Asn Val Ala Ala Ala Ala Phe Asn Lys Asp Ala
865                 870                 875                 880

Leu Leu Asn Trp Leu Lys Glu Tyr Asn Ser Gly Asp Asp Leu Asp Arg
                885                 890                 895

Ala Ile Glu Glu Phe Thr Leu Ser Cys Ala Gly Tyr Cys Val Ala Ser
            900                 905                 910

Tyr Val Leu Gly Ile Gly Asp Arg His Ser Asp Asn Ile Met Val Lys
        915                 920                 925

Lys Thr Gly Gln Leu Phe His Ile Asp Phe Gly His Ile Leu Gly Asn
930                 935                 940

Phe Lys Ser Lys Phe Gly Ile Lys Arg Glu Arg Val Pro Phe Ile Leu
945                 950                 955                 960

Thr Tyr Asp Phe Ile His Val Ile Gln Gln Gly Lys Thr Gly Asn Thr
                965                 970                 975

Glu Lys Phe Gly Arg Phe Arg Gln Cys Cys Glu Asp Ala Tyr Leu Ile
            980                 985                 990

Leu Arg Arg His Gly Asn Leu Phe  Ile Thr Leu Phe Ala  Leu Met Leu
```

-continued

```
                995              1000             1005
Thr Ala Gly Leu Pro Glu Leu Thr Ser Val Lys Asp Ile Gln Tyr
            1010             1015            1020

Leu Lys Asp Ser Leu Ala Leu Gly Lys Ser Glu Glu Glu Ala Leu
            1025             1030            1035

Lys Gln Phe Lys Gln Lys Phe Asp Glu Ala Leu Arg Glu Ser Trp
            1040             1045            1050

Thr Thr Lys Val Asn Trp Met Ala His Thr Val Arg Lys Asp Tyr
            1055             1060            1065

Arg Ser
    1070
```